US010865250B2

(12) United States Patent
Hinner et al.

(10) Patent No.: US 10,865,250 B2
(45) Date of Patent: Dec. 15, 2020

(54) ANTI-CANCER FUSION POLYPEPTIDE

(71) Applicant: Pieris Pharmaceuticals GmbH, Hallbergmoos (DE)

(72) Inventors: Marlon Hinner, Munich (DE); Christine Rothe, Dachau (DE); Shane Olwill, Freising (DE); Rachida Siham Bel Aiba, Munich (DE); Ulrich Moebius, Gauting (DE); Corinna Schlosser, Freising (DE); Thomas Jean Jaquin, Freising (DE)

(73) Assignee: Pieris Pharmaceuticals GmbH, Hallbergmoos (DE)

( * ) Notice: Subject to any disclaimer, the term of this patent is extended or adjusted under 35 U.S.C. 154(b) by 152 days.

(21) Appl. No.: 15/571,561

(22) PCT Filed: May 4, 2016

(86) PCT No.: PCT/EP2016/060041
§ 371 (c)(1),
(2) Date: Nov. 3, 2017

(87) PCT Pub. No.: WO2016/177802
PCT Pub. Date: Nov. 10, 2016

(65) Prior Publication Data
US 2019/0010248 A1 Jan. 10, 2019

(30) Foreign Application Priority Data

May 4, 2015 (EP) ..................................... 15166179
May 18, 2015 (EP) ..................................... 15167917
Sep. 17, 2015 (EP) ..................................... 15002702
Nov. 4, 2015 (EP) ..................................... 15192870
Jan. 11, 2016 (EP) ..................................... 16150705
Apr. 15, 2016 (EP) ..................................... 16000862

(51) Int. Cl.
*C07K 16/30* (2006.01)
*C07K 16/32* (2006.01)
*C07K 14/435* (2006.01)
*C07K 16/28* (2006.01)
*A61P 35/00* (2006.01)
*A61K 39/00* (2006.01)

(52) U.S. Cl.
CPC .............. *C07K 16/32* (2013.01); *A61P 35/00* (2018.01); *C07K 14/435* (2013.01); *C07K 16/2878* (2013.01); *A61K 2039/505* (2013.01); *C07K 2317/52* (2013.01); *C07K 2317/73* (2013.01); *C07K 2317/92* (2013.01); *C07K 2318/20* (2013.01); *C07K 2319/00* (2013.01)

(58) Field of Classification Search
None
See application file for complete search history.

(56) References Cited

U.S. PATENT DOCUMENTS

| | | |
|---|---|---|
| 4,376,110 A | 3/1983 | David et al. |
| 5,728,553 A | 3/1998 | Goodey et al. |
| 5,849,576 A | 12/1998 | Skerra et al. |
| 6,020,163 A | 2/2000 | Conklin |
| 6,099,517 A | 8/2000 | Daugherty |
| 6,103,493 A | 8/2000 | Skerra et al. |
| 6,123,936 A | 9/2000 | Platz et al. |
| 6,177,074 B1 | 1/2001 | Glue et al. |
| 6,403,564 B1 | 6/2002 | Ganguly et al. |
| 6,500,930 B2 | 12/2002 | Adamson |
| 6,566,073 B1 | 5/2003 | Rivera et al. |
| 6,620,413 B1 | 9/2003 | De Sauvage et al. |
| 6,696,245 B2 | 2/2004 | Winter et al. |
| 7,118,915 B2 | 10/2006 | Vogt et al. |
| 7,250,297 B1 | 7/2007 | Beste et al. |
| 7,252,998 B2 | 8/2007 | Skerra et al. |
| 7,723,476 B2 | 5/2010 | Skerra et al. |

(Continued)

FOREIGN PATENT DOCUMENTS

| | | |
|---|---|---|
| DE | 4417598 A1 | 12/1995 |
| DE | 19641876 A1 | 4/1998 |

(Continued)

OTHER PUBLICATIONS

Hinner et al (J Immunotherapy of Cancer, 2015, 1(supple 2): P187, published Nov 4, 2015). (Year: 2015).*

(Continued)

*Primary Examiner* — Lei Yao
(74) *Attorney, Agent, or Firm* — Choate, Hall & Stewart LLP; Brian E. Reese; Dana M. Daukss

(57) ABSTRACT

The disclosure provides a fusion polypeptide specific for both CD137 and HER2/neu, which fusion polypeptide can be useful for directing CD137 clustering and activation to HER2/neu-positive tumor cells. Such fusion polypeptide can be used in many pharmaceutical applications, for example, as anti-cancer agents and/or immune modulators for the treatment or prevention of human diseases such as a variety of tumors. The present disclosure also concerns methods of making the fusion polypeptide described herein as well as compositions comprising such fusion polypeptide. The present disclosure further relates to nucleic acid molecules encoding such fusion polypeptide and to methods for generation of such fusion polypeptide and nucleic acid molecules. In addition, the application discloses therapeutic and/or diagnostic uses of such fusion polypeptide as well as compositions comprising one or more of such fusion polypeptides.

Figure 1:
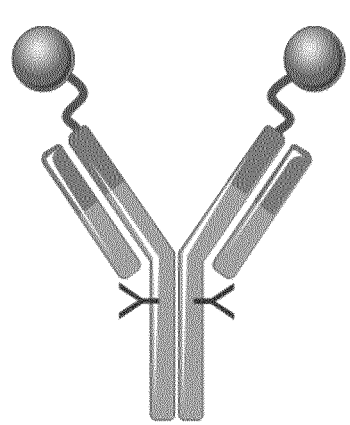
Figure 1:
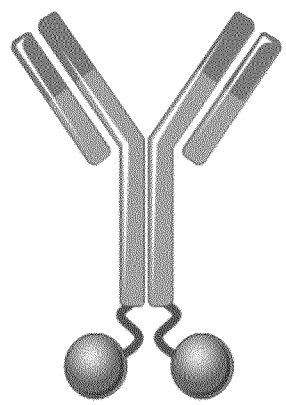
Figure 1:
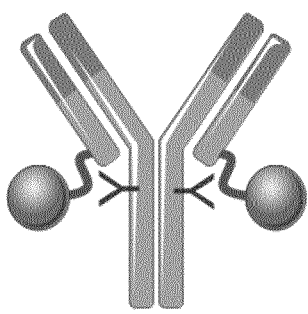
Figure 1:
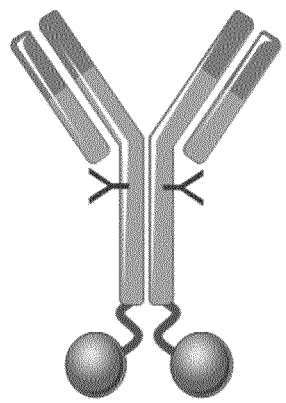
Figure 1:
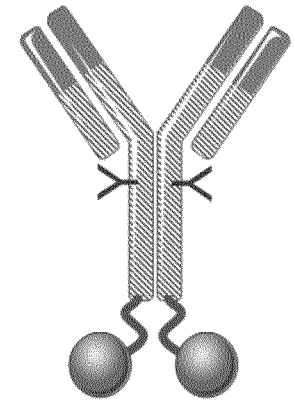

8 Claims, 23 Drawing Sheets
Specification includes a Sequence Listing.

(56) References Cited

U.S. PATENT DOCUMENTS

| | | |
|---|---|---|
| 7,892,827 B2 | 2/2011 | Matschiner et al. |
| 8,158,753 B2 | 4/2012 | Skerra et al. |
| 8,420,051 B2 | 4/2013 | Skerra et al. |
| 8,536,307 B2 | 9/2013 | Skerra et al. |
| 9,040,020 B2 | 5/2015 | Skerra et al. |
| 9,051,382 B2 | 6/2015 | Trentmann et al. |
| 9,221,885 B2 | 12/2015 | Matschiner et al. |
| 9,260,492 B2 | 2/2016 | Matschiner et al. |
| 9,549,968 B2 | 1/2017 | Skerra et al. |
| 9,884,898 B2 | 2/2018 | Corvey et al. |
| 10,273,275 B2 | 4/2019 | Hinner et al. |
| 2003/0069395 A1 | 4/2003 | Sato et al. |
| 2006/0058510 A1 | 3/2006 | Skerra et al. |
| 2006/0088908 A1 | 4/2006 | Skerra et al. |
| 2009/0042785 A1 | 2/2009 | Matschiner et al. |
| 2009/0305982 A1* | 12/2009 | Jensen .................. C07K 14/47 514/21.2 |
| 2010/0285564 A1 | 11/2010 | Skerra et al. |
| 2011/0262353 A1 | 10/2011 | Skerra et al. |
| 2012/0244596 A1 | 9/2012 | Skerra et al. |
| 2013/0079286 A1* | 3/2013 | Skerra ................ A61K 38/1709 514/17.7 |
| 2013/0316962 A1 | 11/2013 | Skerra et al. |
| 2014/0080177 A1 | 3/2014 | Skerra et al. |
| 2016/0362460 A1 | 12/2016 | Olwill et al. |
| 2017/0114109 A1 | 4/2017 | Skerra et al. |
| 2017/0166615 A1 | 6/2017 | Matschiner et al. |
| 2017/0369542 A1 | 12/2017 | Trentmann et al. |
| 2018/0016312 A1 | 1/2018 | Bel Aiba et al. |
| 2018/0021418 A1 | 1/2018 | Hinner |
| 2018/0141988 A1 | 5/2018 | Hinner et al. |
| 2018/0148484 A1 | 5/2018 | Hinner et al. |

FOREIGN PATENT DOCUMENTS

| | | |
|---|---|---|
| DE | 19742706 A1 | 4/1999 |
| DE | 19926068 C1 | 1/2001 |
| EP | 0 330 451 A2 | 8/1989 |
| EP | 0 361 991 A2 | 4/1990 |
| JP | 2005503829 A | 2/2005 |
| JP | 2007284351 A | 11/2007 |
| WO | WO-96/23879 A1 | 8/1996 |
| WO | WO-98/16873 A1 | 4/1998 |
| WO | WO-98/33914 A1 | 8/1998 |
| WO | WO-99/16873 A1 | 4/1999 |
| WO | WO-99/064016 A1 | 12/1999 |
| WO | WO-00/075308 A1 | 12/2000 |
| WO | WO-03/029462 A1 | 4/2003 |
| WO | WO-03/029463 A2 | 4/2003 |
| WO | WO-03/029471 A1 | 4/2003 |
| WO | WO-2005/019254 A1 | 3/2005 |
| WO | WO-2005/019255 A1 | 3/2005 |
| WO | WO-2005/019256 A2 | 3/2005 |
| WO | WO-2006/056464 A2 | 6/2006 |
| WO | WO-2007/038619 A2 | 4/2007 |
| WO | WO-2009/052390 A1 | 4/2009 |
| WO | WO-2009/068649 A2 | 6/2009 |
| WO | WO-2009/114110 A1 | 9/2009 |
| WO | WO-2009/156456 A1 | 12/2009 |
| WO | WO-2010/097394 A1 | 9/2010 |
| WO | WO-2010/136492 A2 | 12/2010 |
| WO | WO-2011/015634 A2 | 2/2011 |
| WO | WO-2012/072806 A1 | 6/2012 |
| WO | WO2013164694 * | 3/2013 |
| WO | WO-2013/164694 A1 | 11/2013 |
| WO | WO-2015/104406 A2 | 7/2015 |
| WO | WO2015104406 * | 7/2015 |

OTHER PUBLICATIONS

Hinner et al., "Costimulatory T cell engagement via a novel bispecific anti-CD137/anti HER2 protein based on Anticalin technology," Sep. 2015, poster.

Hinner et al., "Costimulatory T cell engagement via a novel bispecific anti-CD137/anti-HER2 protein," Journal for Immunotherapy of Cancer, vol. 3, suppl 2, 2015, p. P187.

Kohrt et al. "Stimulation of natural killer cells with a CD137-specific antibody enhances trastuzumab efficacy in xenotransplant models of breast cancer," Journal of Clinical Investigation, vol. 122, No. 3, 2012, pp. 1066-1075.

Stagg et al., "Anti-ErbB-2 mAb therapy requires type I and II interferons and synergizes with anti-PD-1 or anti-CD137 mAb therapy," PNAS, vol. 108, No. 17, 2011.

Sternberg et al., "Poster Session: Immunogenomics," European Journal of Cancer, vol. 55, Mar. 2016, p. S16-S17.

International Search Report and Written Opinion issued in corresponding application No. PCT/EP2016/060041 dated Jul. 1, 2016.

"Chain A Crystal Structure of Siderocalin (Ngal, Lipocalin 2) Complexed With Trencam-3,2-Hopo, A Cepabactin Analogue," GenBank Accession No. 1X71_A, Sep. 24, 2008.

Altschul et al., Gapped BLAST and PSI-BLAST: a new generation of protein database search programs, Nucleic Acids Res., 25(17):3389-3402 (1997).

Altschul, S. et al., Basic Local Alignment Search Tool; J. Mol. Biol., 215:403-410 (1990).

Amstutz, P. et al., In vitro display technologies: novel developments and applications, Curr. Opin. Biotechnol., 2001, 12:400-405.

Bachmann, Barbara J., Linkage Map of *Escherichia coli* K-12. Edition 8, Microbial. Rev., Jun. 1990, 54(2):130-197.

Beck, et al., Nucleotide Sequence and Genome Organisation of Filamentous Bacteriophages f1 and fd, Gene, vol. 16, pp. 35-58, 1981.

Beste, G. et al., Small antibody-like proteins with prescribed ligand specificities derived from the lipocalin fold, Proc. Natl. Acad. Sci. USA, Mar. 1999, 96:1898-1903.

Bittker, J. et al., Nucleic acid evolution and minimization by nonhomologous random recombination, Nat. Biotechnol., Oct. 2002, 20:1024-1029.

Biburger, M. et al., A Novel Bispecific Tetravalent Antibody Fusion Protein to Target Costimulatory Activity for T-cell Activation to Tumor Cells Overexpressing ErbB2/HER2, J. Mol. Biol., 346:1299-1311 (2005).

Bos et al., OctoDEX.TM.—Controlled Release of Pharmaceutical Proteins from Hydrogels, Business Briefing: Pharmatech, 2003:1-6.

Breustedt, D. et al., Comparative ligand-binding analysis of ten human lipocalins, Biochim. Biophys. Acta, 2006, 1764:161-173.

Broders, O et al., Hyperphage. Improving antibody presentation in phage display, Methods Mol. Biol., 2003, 205:295-302.

Brody et al., Active and Passive Immunotherapy for Neurodegenerative Disorders, Annu. Rev. Neurosci., 2008, 31:175-193.

Bruckdorfer, T., et al., From Production of Peptides in Milligram Amounts for Research to Multi-Tons Quantities for Drugs of the Future, Curr. Pharm. Biotechnol., 2004, 5:29-43.

Bullock, W. et al., XL1-Blue: A High Efficiency Plasmid Transforming recA *Escherichia coli* Strain with Beta-Galactosidase Selection, Biotechniques, 1987, 5(4):376-378.

Bundgaard, J.R. et al., Molecular Cloning and Expression of a cDNA Encode NGAL: A Lipocalin Expressed in Human Neutrophils, Biochemical and Biophysical Research Communications, Aug. 15, 1994, pp. 1468-1475, vol. 202, No. 3, XP002036694.

Carnemolla et al., Phage Antibodies with PAN-Species Recognition of the Oncofoetal Angiogenesis Marker Fibronectin ED-B Domain, Int. J. Cancer, 1996, 68:397-405.

Chan et al., The primary structure of rat α 2μ globulin-related protein, Nucleic Acids Research, vol. 16, No. 23, pp. 11368, 1988.

Coles, et al., The Solution Structure and Dynamics of Human Neutrophil Gelatinase-associated Lipocalin, J. Mol. Biol., vol. 289, pp. 139-157, 1999.

Communication Pursuant to Article 94(3) EPC dated Jan. 5, 2015 issued in European Patent Application No. 09 769 304.8.

Corneillie et al., Irreversibly binding anti-metal chelate antibodies: Artificial receptors for pretargeting, Journal of Inorganic Biochemistry, May 1, 2006, 100(5-6):882-890.

Dennis, M. et al., Albumin Binding as a General Strategy for Improving the Pharmacokinetics of Proteins, J. Biol. Chem., Sep. 20, 2002, 277(38):35035-35043.

(56) References Cited

OTHER PUBLICATIONS

Dodel et al., Immunotherapy for Alzheimer's disease, Lancet Neurology, Apr. 2003, 2:215-220.
Ebbinghaus et al., Diagnostic and Therapeutic Applications of Recombinant Antibodies: Targeting the Extra-Domain B of Fibronectin, A Marker of Tumor Angiogenesis, Curr. Pharm. Des., 2004, 10:1537-1549.
Fitzgerald, Kevin, In Vitro Display Technologies—New Tools for Drug Discovery, Reviews, vol. 5, No. 6, pp. 253-258, Jun. 2000.
Fling, S. and Gregerson, D., Peptide and Protein Molecular Weight Determination by Electrophoresis Using a High-Molarity Tris Buffer System without Urea, Anal. Biochem., 1986, 155:83-88.
Flower, Darren R., Multiple Molecular Recognition Properties of the Lipocalin Protein Family, Journal of Molecular Recognition, 1995, 8:185-195.
Flower, Darren R., The lipocalin protein family: structure and function, Biochem. J., 1996, 318:1-14.
Frank, Ronald, The SPOT-synthesis technique Synthetic Peptide arrays on membrane supports—principles and applications, J. Immunol. Methods, 2002, 267:13-26.
Fuerteges, F. and Abuchowski, A., The Clinical Efficacy of Poly(Ethylene Glycol)-Modified Proteins,: J. Control. Release, 1990, 11:139-148.
Fujii, Phage display and beyond antibody—molecular target by antibody molecule, Seikagaku, 2010, vol. 82, No. 8, pp. 710-726, Abstract.
Gaillard, P. et al., Diphtheria toxin receptor-targeted brain drug delivery, International Congress Series., 2005, 1277:185-198.
Gaillard, P. et al., Targeted delivery across the blood-brain barrier, Expert Opin Drug Deliv., 2005, 2(2):299-309.
Gasteiger et al., ExPASy: the proteomics server for in-depth protein knowledge and analysis, Nucleic Acids Res., 2003, 31(13):3784-3788.
Gill, D. et al., Biopharmaceutical drug discovery using novel protein scaffolds, Curr. Opin. Biotechnol., 2006, 17(6):653-658.
Godovac-Zimmermann, Jasminka, The structural motif of β-lactoglobulin and retinol-binding protein: a basic framework for binding and transport of small hydrophobic molecules?, TIBS, Feb. 1988, vol. 13, pp. 64-66.
Goetz, D. et al., Ligand Preference Inferred from the Structure of Neutrophil Gelatinase Associated Lipocalin, Biochemistry, 2000, 39:1935-1941.
Gronwall et al., Selection and characterization of Affibody ligands binding to Alzheimer amyloid β peptides, J. Biotechnol., 2007, 128:162-183.
Haass et al., Soluble protein oligomers in neurodegeneration: lessons from the Alzheimer's amyloid β-peptide, Nat. Rev. Mol. Cell. Biol., Feb. 2007, 8:101-112.
Hengen, Paul N., Methods and Reagents, Trends Biochem. Sci., vol. 21, pp. 75-76, 1996.
Hoess, Ronald H., Phage Display of Peptides and Protein Domains, Structural Biology, vol. 3, pp. 572-279, 1993.
Hohlbaum, A. et al., Anticalins: the lipocalin family as a novel protein scaffold for the development of next-generation immunotherapies, Future Drugs Ltd, vol. 3, 2007, pp. 491-501.
Holzfeind, P. et al., Structural Organization of the Gene Encoding the Human Lipocalin Tear Prealbumin and Synthesis of the Recombinant Protein in *Escherichia coli*, Gene, vol. 139, pp. 177-183, 1994.
Hortschansky et al., The aggregation Kinetics of Alzheimer's β-amyloid peptide is controlled by stochastic nucleation, Protein Sci., 2005, 14:1753-1759.
Hoyer, W. et al., Stabilization of a β-hairpin in monomeric Alzheimer's amyloid-β. peptide inhibits amyloid formation, Proc. Natl. Acad. Sci. USA, Apr. 1, 2008, 105(13):5099-5104.
Huber et al., Molecular Structure of the Bilin Binding Protein (BBP) from *Pieris brassicae* After Refinement at 2•0 Å Resolution, J. Mol. Biol., 1987, vol. 198, pp. 499-513.
International Search Report and Written Opinion issued in corresponding application No. PCT/EP2016/059959 dated Jun. 29, 2016.
International Search Report dated Nov. 27, 2009 in PCT/EP2009/057925, 3 pages.
Junttila, T. et al., Superior in vivo Efficacy of Afucosylated Trastuzumab in the Treatment of HER2-Amplified Breast Cancer; Cancer Res., 70(11): 4481-4489 (2010).
Karlsson et al., Kinetic analysis of monoclonal antibody-antigen interactions with a new biosensor based analytical system, J. Immunol. Methods, 1991, 145:229-240.
Kaspar et al., Fibronectin as target for tumor therapy, Int. J. Cancer, 2006, 118:1331-1339.
Kaufman et al., Transgenic Analysis of 100-kb Human beta-Globin Cluster-Containing DNA Fragment Propagated as a Bacterial Artificial Chromosome, Blood, 1999, 94:3178-3184.
Khurana et al., Mechanism of thioflavin T binding to amyloid fibrils, J. Struct. Biol., 2005, 151:229-238.
Kim, H. et al., High-Affinity Recognition of Lanthanide(III) Chelate Complexes by a Reprogrammed Human Lipocalin 2, J. Am. Chem. Soc., 2009, 131:3565-3576.
Kjelsden, L. et al., Human Neutrophil Gelatinase-Associated Lipocalin and Homologous Proteins in Rat and Mouse, Biochimica et Biophysica Acta, vol. 1482, pp. 272-283, 2000.
Konig, T. And Skerra, A., Use of an albumin-binding domain for the selective immobilization of recombinant capture antibody fragments on ELISA plates, J. Immunol. Methods, 1998, 218:73-83.
Korean Office Action issued in corresponding application No. 10-2012-7017730 dated Jul. 28, 2018 with English translation.
Korndoerfer et al., "Crystallographic Analysis of an Anticalin" with Tailored Specificity for Fluorescein Reveals High Structural Plasticity of the Lipocalin Loop Region, Proteins: Structure, Function and Bioinformatics, 2003, vol. 53, pp. 121-129.
Korndoerfer et al., Structural Mechanism of Specific Ligand Recognition by a Lipocalin Tailored for the Complexation of Digoxigenin, J. Mol. Biol., 2003, vol. 330, pp. 385-396.
Kraulis, et al., The Serum Albumin-Binding Domain of Streptococcal Protein G is a Three-Helical Bundle: A Heteronuclear NMR Study, FEBS Letters, vol. 378, pp. 190-194, 1996.
Lazar et al. Transforming Growth Factor α: Mutation of Aspartic Acid 47 and Leucine 48 Results in Different Biological Activities, Molecular and Cellular Biology, Mar. 1988, 8(3):1247-1252.
Leahy et al., Crystallization of a Fragment of Human Fibronectin: Introduction of Methionine by Site-Directed Mutagenesis to Allow Phasing via Selenomethionine, Proteins, 1994, 19:48-54.
Lichtlen et al., Antibody-based approaches in Alzheimer's research: safety, pharmacokinetics, metabolism, and analytical tools, J. Neurochem., 2007, 104:859-874.
Lipocalin, definition of Lipocalin by Medical dictionary (pp. 1-3; Dec. 18, 2017).
Lohrengel, B. et al., Expression and Purification of Woodchuck Tumour Necrosis Factor Alpha, Cytokine, vol. 12, No. 6, pp. 573-577, Jun. 2000.
Low, N. et al., Mimicking Somatic Hypermutation: Affinity Maturation of Antibodies Displayed on Bacteriophage Using a Bacterial Mutator Strain, J. Mol. Biol., vol. 260, pp. 359-368, 1996.
Lowman, H.B. Bacteriophage display and discovery of peptides leads for drug development, Annu. Rev. Biophys. Biomol. Struct., 1997, 26:401-424.
Lynch et al., The promise of 4-1 BB (CD137)-mediated immunomodulation and the immunotherapy of cancer, Immunological Reviews, vol. 222, 2008, pp. 277-286.
Mateo, C. et al., Removal of Amphipathic Epitopes from Genetically Engineered Antibodies: Production of Modified Immunoglobulins with Reduced Immunogenicity, Hybridoma, 2000, 19(6):463-471.
Meidan et al., Emerging Technologies in Transdermal Therapeutics, Am. J. Ther., 2004, 11(4):312-316.
Mercader et al., Generation of anticalins with specificity for a nonsymmetric phthalic acid ester, Analytical Biochemistry, 2002, vol. 308, 269-277.
Moretto et al., Conformation-sensitive Antibodies against Alzheimer Amyloid-β. by Immunization with a Thioredoxin-constrained B-cell Epitope Peptide, J. Biol. Chem., 2007, 282(15):11436-11445.

(56) References Cited

OTHER PUBLICATIONS

Muller, H. et al. Functional Expression of the Uncomplexed Serum Retinol-binding Protein in Escherichia coli, J. Mol. Biol., 1993, vol. 230, pp. 725-732.

Muller, H. et al., Grafting of a High-Affinity Zn(II)-Binding Site on the β-Barrel of Retinol-Binding Protein Results in Enhanced Folding Stability and Enables Simplified Purification, Biochemistry, 1994, vol. 33, pp. 14126-14135.

Murakami, H. et al., Random insertion and deletion of arbitrary number of bases for codon-based random mutation of DNAs, Nat. Biotechnol., Jan. 2002, 20:76-81.

Ngo, T. et al., Computational Complexity, Protein Structure Prediction, and the Levinthal Paradox, The Protein Folding Problem and Tertiary Structure Prediction, pp. 492-495 (1994).

Notice of Reasons for Rejections dated Jan. 20, 2015 issued in Japanese Application No. 2012-542505, with English translation.

Olsson, C. et al., CTLA-4 Ligation Suppresses CD28-induced NF-KB and AP-1 Activity in Mouse T Cell Blasts, The Journal of Biological Chemistry, 274(20):14400-14405 (1999).

Osborn, B. et al., Pharmacokinetic and Pharmacodynamic Studies of a Human Serum Albumin-Interferon-α Fusion Protein in Cynomolgus Monkeys, J. Pharmacol. Exp. Ther., 2002, 303(2):540-548.

Paine et al., The Lipocalin website, Elsevier Science B.V., Biochimica et Biophysica Acta 1482, pp. 351-352, 2000.

Papiz, et al., The Structure of Beta-Lactoglobulin and Its Similarity to Plasma Retinol-Binding Protein, Nature, vol. 324, pp. 383-385, 1986.

PCT International Search Report issued in application No. PCT/EP2015/050378 dated Jul. 3, 2015.

Pervaiz, et al., Homology and Structure-Function Correlations Between ?1-Acid Glycoprotein and Serum Retinol-Binding Protein and Its Relatives, 1987, The FASEB journal 1.3 (1987): 209-214.

Pini et al., Design and Use of a Phage Display Library, J. Biol. Chem., Aug. 21, 1998, 273(34):21769-21776.

Pini, A. et al., Phage Display and Colony Filter Screening for High-Throughput Selection of Antibody Libraries, Comb. Chem. High Throughput Screen., 2002, 5:503-510.

Pujuguet et al., Expression of Fibronectin ED-A+ and ED-B+ Isoforms by Human and Experimental Colorectal Cancer, Am. J. Pathol., Feb. 1996, 148(2):579-592.

Ramoni, R. et al., the protein scaffold of the lipocalin odorant-binding protein is suitable for the design of new biosensors for the detection of explosive components, J. Phys. Condens. Matter, 19: 8 pages (2007).

Redl, Bernhard, Human tear lipocalin, Biochim. Biophys. Acta, 2000, 1482:241-248.

Roberts, Richard W., Totally In Vitro Protein Selection Using mRNA-Protein Fusions and Ribosome Display, Current Opinion in Chemical Biology, vol. 3, pp. 268-273, 1999.

Rodi, D. And Makowski, L., Phage-display technology—finding a needle in a vast molecular haystack, Curr. Opin. Biotechnol., 1999, 10:87-93.

Rothe, C. And Skerra, A., Anticalin Proteins as Therapeutic Agents in Human Diseases, BioDrugs, 32:233-243 (2018).

Schlehuber et al., Lipocalins in drug discovery: from natural ligand-binding proteins to 'anticalins', Drug Discovery Today, 10(1):23-33 (2005).

Schlehuber, S. and Skerra, A. et al., Duocalins, engineered ligand-binding proteins with dual specificity derived from the lipocalin fold, Biol. Chem., Sep. 2001, 382:1335-1342.

Schlehuber, S. and Skerra, A., Tuning ligand affinity, specificity, and folding stability of an engineered lipocalin variant—a so-called 'anticalin'—using a molecular random approach, Biophysical Chemistry 96 (2002) 213-228.

Schlehuber, S. et al., A Novel Type of Receptor Protein, Based on the Lipocalin Scaffold, with Specificity for Digoxigenin, J. Mol. Biol., 2000, 297:1105-1120.

Schliemann et al., Antibody-based targeting of the tumor vasculature, Biochim. Biophys. Acta, 2007, 1776:175-192.

Schmidt et al., The Strep-tag system for one-step purification and high-affinity detection of capturing of proteins, Nat. Protoc., 2007, 2(6):1528-1535.

Schmidt, F. et al., The bilin-binding protein of Pieris brassicae cDNA sequence and regulation of expression reveal distinct features of this insect pigment protein, Eur. J. Biochem., 1994, 219:855-863.

Schmidt, T. et al., Molecular Interaction Between the Strep-tag Affinity Peptide and its Cognate Target, Streptavidin, J. Mol. Biol., 1996, 255:753-766.

Schoepfer, Ralf, The pRSET Family of T7 Promoter Expression Vectors for Escherichia coli, Gene, vol. 124, pp. 83-85, 1993.

Schonfeld, D. et al. An engineered lipocalin specific for CTLA-4 reveals a combining site with structural and conformational features similar to antibodies, PNAS, 106(20): 8198-8203 (2009).

Sivaprasadarao, A. et al., Lipocalin structure and function, Biochemical Society Transactions, 1990. pp. 619-622.

Skerra, A., Engineered protein scaffolds for molecular recognition, J. Mol. Recognit., 2000; 13:167-187.

Skerra, A., et al., Lipocalins as a scaffold, Elsevier Science B.V., Biochimica et Biophysica Acta 1482, pp. 337-350, 2000.

Skerra, Alternative binding proteins: Anticalins—harnessing the structural plasticity of the lipocalin ligand pocket to engineer novel binding activities; FEBS Journal, 275(11): 2677-2683 (Jun. 2008).

Skerra, Arne, Use of the tetracycline promoter for the tightly regulated production of a murine antibody fragment in Escherichia coli, Gene, 1994, 151:131-135.

Skerra, et al., Filter Screening of Antibody Fab Fragments Secreted From Individual Bacterial Colonies: Specific Detection of Antigen Binding with a Two-Membrane System, Anal. Biochem., vol. 196, pp. 151-155, 1991.

Smith, T.F. et al., Identification of Common Molecular Subsequences; J. Mol. Biol., 147:195-197 (1981).

Stoesz, S. et al., Overexpression of neu-related lipocalin (NRL) in neu-initiated but not ras or chemically initiated rat mammary carcinomas, Oncogene (1995), 11, pp. 2233-2241.

Studier, F.W., and Moffatt, B.A., Use of Bacteriophage T7 RNA Polymerase to Direct Selective High-level Expression of Cloned Genes, J. Mol. Biol., 1986, 189:113-130.

Stump et al., Site-directed Mutagenesis of Rat Cellular Retinol-binding Protein, J. Biol. Chem., Mar. 1991, 266(7):4622-4630.

Tartof et al., Improved Media for Growing Plasmid and Cosmid Clones, Focus, Bethesda Research Laboratory, 1987, 9(2):12.

Tulasne, D. et al., C-Terminal Peptide of Thrombospondin-1 Includes Platelet Aggregation Through the Fc Receptor γ-Chain-Associated Signaling Pathway and by Agglutination, Blood, vol. 98, No. 12, pp. 3346-3352, Dec. 1, 2001.

Vajo, Z. and Duckworth, W., Genetically Engineered Insulin Analogs: Diabetes in the New Millenium, Pharmacol. Rev., 2000, 52(1):1-9.

Venturi, M. et al., High Level Production of Functional Antibody Fab Fragments in an Oxidizing Bacterial Cytoplasm, J. Mol. Biol., 2002, 315:1-8.

Virnekas et al., Trinucleotide phosphoramidites: ideal reagents for the synthesis of mixed oligonucleotides for random mutagenesis, Nucleic Acids Res, 1994, 22(25):5600-5607.

Vogt, M. And Skerra, A., Construction of an Artificial Receptor Protein ("Anticalin") Based on the Human Apolipoprotein D, ChemBioChem, 5: 191-199 (2004).

Voss, et al., Mutagenesis of a Flexible Loop in Streptavidin Leads to Higher Affinity for the Strep-Tag II Peptide and Improved Performance in Recombinant Protein Purification, Protein Engineering, vol. 10, No. 8, pp. 975-982, 1997.

Wang et al., Expanding the Genetic Code of Escherichia coli, Science, Apr. 20, 2001, 292:498-500.

Wang et al., Expanding the genetic code, Chem. Comm., 2002, 1:1-11.

Wang et al., Rapid analysis of gene expression (RAGE) facilitates universal expression profiling, Nucleic Acids Research, 1999, 27(23):4609-4618.

Wang, A. M. et al., Molecular Cloning of the Complementary DNA for Human Tumor Necrosis Factor, Science, vol. 228, pp. 149-154, 1985 (Abstract).

(56) References Cited

OTHER PUBLICATIONS

Wells, J. et al., Rapid Evolution of Peptide and Protein Binding Properties In Vitro, Current Opinion in Structural Biology, vol. 2, pp. 597-604, 1992.

Wells, James A., Additivity of Mutational Effects in Proteins, Biochemistry, Sep. 18, 1990, 29(37):8509-8517.

Wilson, D. et al., The use of mRNA display to select high-affinity protein-binding peptides, Proc. Natl. Acad. Sci. USA, Mar. 27, 2001, 98(7):3750-3755.

Yanisch-Perron, C. et al., Improved M13 phage cloning vectors and host strains: nucleotide sequences of the M13mp18 and pUC19 vectors, Gene, 1985, 33:103-119.

Zaccolo, M.et al., An Approach to Random Mutagenesis of DNA Using Mixtures of Triphosphate Derivatives of Nucleoside Analogues, J. Mal. Biol., 1996, 255:589-603.

Zardi, L. et al., Transformed human cells produce a new fibronectin isoform by preferential alternative splicing of a previously unobserved exon, EMBO J, 6(8):2337-42 (1987).

LCN1—Lipocalin-1 precursor—*Homo sapiens* (Human)—LCN1 gene protein, UniProtKB—P31025 (LCN1_HUMAN), retrieved from https://www.uniprot.org/uniprot/P31025, 11 pages (retrieved on Aug. 27, 2019).

UNIPROT Database—Signal peptide, retrieved from https://www.uniprot.org/help/signal, 2 pages (retrieved on Aug. 27, 2019).

UniProt sequence G3SEI1 (G3SEI1_GORGO), retrieved from https://www.uniprot.org/uniprot/G3SEI1, integrated into UniProtKB Nov. 16, 2011, 7 pages.

* cited by examiner

SEQ ID NO's: 13 and 14

SEQ ID NO's: 15 and 16

SEQ ID NO's: 7 and 8

SEQ ID NO's: 11 and 12

SEQ ID NO's: 9 and 10

SEQ ID NO's: 5 and 6

A

B

A

B

SEQUENCE LISTING

```
<160> NUMBER OF SEQ ID NOS: 52

<210> SEQ ID NO 1
<211> LENGTH: 178
<212> TYPE: PRT
<213> ORGANISM: artificial
<220> FEATURE:
<223> OTHER INFORMATION: negative control

<400> SEQUENCE: 1
```

-continued

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Leu Ala Gly Asn Ala Ile Leu Arg Glu Asp Lys Asp Pro
        35                  40                  45

Gln Lys Met Tyr Ala Thr Ile Tyr Glu Leu Lys Glu Asp Lys Ser Tyr
    50                  55                  60

Asn Val Thr Ser Val Leu Phe Arg Lys Lys Cys Asp Tyr Trp Ile
65                  70                  75                  80

Arg Thr Phe Val Pro Gly Ser Gln Pro Gly Glu Phe Thr Leu Gly Asn
                85                  90                  95

Ile Lys Ser Tyr Pro Gly Leu Thr Ser Tyr Leu Val Arg Val Val Ser
            100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 2
<211> LENGTH: 178
<212> TYPE: PRT
<213> ORGANISM: artificial
<220> FEATURE:
<223> OTHER INFORMATION: positive control lipocalin mutein

<400> SEQUENCE: 2

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Arg Leu Arg Glu Asp Lys Asp Pro
        35                  40                  45

Ile Lys Met Met Ala Thr Ile Tyr Glu Leu Lys Glu Asp Lys Ser Tyr
    50                  55                  60

Asp Val Thr Met Val Lys Phe Asp Lys Lys Cys Met Tyr Asp Ile
65                  70                  75                  80

Trp Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
            115                 120                 125

Asn Arg Glu Glu Phe Tyr Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 3
<211> LENGTH: 450
<212> TYPE: PRT
<213> ORGANISM: artificial
<220> FEATURE:
<223> OTHER INFORMATION: benchmark antibody heavy chain

<400> SEQUENCE: 3

| Glu | Val | Gln | Leu | Val | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Ala | Ser | Gly | Phe | Asn | Ile | Lys | Asp | Thr |
|---|---|---|---|---|---|---|---|---|---|---|---|---|---|---|---|
| | | | 20 | | | | | 25 | | | | | 30 | | |

| Tyr | Ile | His | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ala | Arg | Ile | Tyr | Pro | Thr | Asn | Gly | Tyr | Thr | Arg | Tyr | Ala | Asp | Ser | Val |
|---|---|---|---|---|---|---|---|---|---|---|---|---|---|---|---|
| 50 | | | | | 55 | | | | | 60 | | | | | |

| Lys | Gly | Arg | Phe | Thr | Ile | Ser | Ala | Asp | Thr | Ser | Lys | Asn | Thr | Ala | Tyr |
|---|---|---|---|---|---|---|---|---|---|---|---|---|---|---|---|
| 65 | | | | | 70 | | | | | 75 | | | | | 80 |

| Leu | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ser | Arg | Trp | Gly | Gly | Asp | Gly | Phe | Tyr | Ala | Met | Asp | Tyr | Trp | Gly | Gln |
|---|---|---|---|---|---|---|---|---|---|---|---|---|---|---|---|
| | | | 100 | | | | | 105 | | | | | 110 | | |

| Gly | Thr | Leu | Val | Thr | Val | Ser | Ser | Ala | Ser | Thr | Lys | Gly | Pro | Ser | Val |
|---|---|---|---|---|---|---|---|---|---|---|---|---|---|---|---|
| | | | 115 | | | | | 120 | | | | | 125 | | |

| Phe | Pro | Leu | Ala | Pro | Ser | Ser | Lys | Ser | Thr | Ser | Gly | Gly | Thr | Ala | Ala |
|---|---|---|---|---|---|---|---|---|---|---|---|---|---|---|---|
| 130 | | | | | 135 | | | | | 140 | | | | | |

| Leu | Gly | Cys | Leu | Val | Lys | Asp | Tyr | Phe | Pro | Glu | Pro | Val | Thr | Val | Ser |
|---|---|---|---|---|---|---|---|---|---|---|---|---|---|---|---|
| 145 | | | | | 150 | | | | | 155 | | | | | 160 |

| Trp | Asn | Ser | Gly | Ala | Leu | Thr | Ser | Gly | Val | His | Thr | Phe | Pro | Ala | Val |
|---|---|---|---|---|---|---|---|---|---|---|---|---|---|---|---|
| | | | | 165 | | | | | 170 | | | | | 175 | |

| Leu | Gln | Ser | Ser | Gly | Leu | Tyr | Ser | Leu | Ser | Ser | Val | Val | Thr | Val | Pro |
|---|---|---|---|---|---|---|---|---|---|---|---|---|---|---|---|
| | | | 180 | | | | | 185 | | | | | 190 | | |

| Ser | Ser | Ser | Leu | Gly | Thr | Gln | Thr | Tyr | Ile | Cys | Asn | Val | Asn | His | Lys |
|---|---|---|---|---|---|---|---|---|---|---|---|---|---|---|---|
| | | | 195 | | | | | 200 | | | | | 205 | | |

| Pro | Ser | Asn | Thr | Lys | Val | Asp | Lys | Lys | Val | Glu | Pro | Lys | Ser | Cys | Asp |
|---|---|---|---|---|---|---|---|---|---|---|---|---|---|---|---|
| 210 | | | | | 215 | | | | | 220 | | | | | |

| Lys | Thr | His | Thr | Cys | Pro | Pro | Cys | Pro | Ala | Pro | Glu | Leu | Leu | Gly | Gly |
|---|---|---|---|---|---|---|---|---|---|---|---|---|---|---|---|
| 225 | | | | | 230 | | | | | 235 | | | | | 240 |

| Pro | Ser | Val | Phe | Leu | Phe | Pro | Pro | Lys | Pro | Lys | Asp | Thr | Leu | Met | Ile |
|---|---|---|---|---|---|---|---|---|---|---|---|---|---|---|---|
| | | | | 245 | | | | | 250 | | | | | 255 | |

| Ser | Arg | Thr | Pro | Glu | Val | Thr | Cys | Val | Val | Val | Asp | Val | Ser | His | Glu |
|---|---|---|---|---|---|---|---|---|---|---|---|---|---|---|---|
| | | | 260 | | | | | 265 | | | | | 270 | | |

| Asp | Pro | Glu | Val | Lys | Phe | Asn | Trp | Tyr | Val | Asp | Gly | Val | Glu | Val | His |
|---|---|---|---|---|---|---|---|---|---|---|---|---|---|---|---|
| | | 275 | | | | | 280 | | | | | 285 | | | |

| Asn | Ala | Lys | Thr | Lys | Pro | Arg | Glu | Glu | Gln | Tyr | Asn | Ser | Thr | Tyr | Arg |
|---|---|---|---|---|---|---|---|---|---|---|---|---|---|---|---|
| | | 290 | | | | | 295 | | | | | 300 | | | |

| Val | Val | Ser | Val | Leu | Thr | Val | Leu | His | Gln | Asp | Trp | Leu | Asn | Gly | Lys |
|---|---|---|---|---|---|---|---|---|---|---|---|---|---|---|---|
| 305 | | | | | 310 | | | | | 315 | | | | | 320 |

| Glu | Tyr | Lys | Cys | Lys | Val | Ser | Asn | Lys | Ala | Leu | Pro | Ala | Pro | Ile | Glu |
|---|---|---|---|---|---|---|---|---|---|---|---|---|---|---|---|
| | | | | 325 | | | | | 330 | | | | | 335 | |

| Lys | Thr | Ile | Ser | Lys | Ala | Lys | Gly | Gln | Pro | Arg | Glu | Pro | Gln | Val | Tyr |
|---|---|---|---|---|---|---|---|---|---|---|---|---|---|---|---|
| | | | 340 | | | | | 345 | | | | | 350 | | |

| Thr | Leu | Pro | Pro | Ser | Arg | Glu | Glu | Met | Thr | Lys | Asn | Gln | Val | Ser | Leu |
|---|---|---|---|---|---|---|---|---|---|---|---|---|---|---|---|
| | | | 355 | | | | | 360 | | | | | 365 | | |

```
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 4
<211> LENGTH: 214
<212> TYPE: PRT
<213> ORGANISM: artificial
<220> FEATURE:
<223> OTHER INFORMATION: benchmark antibody light chain

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 5
<211> LENGTH: 643
<212> TYPE: PRT
<213> ORGANISM: artificial
<220> FEATURE:
<223> OTHER INFORMATION: fusion polypeptide
```

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys Gly Gly Gly Gly Ser Gly Gly Gly Ser Gly Gly Gly Gly
450                 455                 460

Ser Gln Asp Ser Thr Ser Asp Leu Ile Pro Ala Pro Pro Leu Ser Lys
465                 470                 475                 480

Val Pro Leu Gln Gln Asn Phe Gln Asp Asn Gln Phe His Gly Lys Trp
                485                 490                 495

Tyr Val Gly Gln Ala Gly Asn Ile Arg Leu Arg Glu Asp Lys Asp
            500                 505                 510

Pro Ile Lys Met Met Ala Thr Ile Tyr Glu Leu Lys Glu Asp Lys Ser
            515                 520                 525

Tyr Asp Val Thr Met Val Lys Phe Asp Asp Lys Lys Cys Met Tyr Asp
            530                 535                 540

Ile Trp Thr Phe Val Pro Gly Ser Gln Pro Gly Glu Phe Thr Leu Gly
545                 550                 555                 560

Lys Ile Lys Ser Phe Pro Gly His Thr Ser Ser Leu Val Arg Val Val
                565                 570                 575

Ser Thr Asn Tyr Asn Gln His Ala Met Val Phe Phe Lys Phe Val Phe
            580                 585                 590

Gln Asn Arg Glu Glu Phe Tyr Ile Thr Leu Tyr Gly Arg Thr Lys Glu
            595                 600                 605

Leu Thr Ser Glu Leu Lys Glu Asn Phe Ile Arg Phe Ser Lys Ser Leu
            610                 615                 620

Gly Leu Pro Glu Asn His Ile Val Phe Pro Val Pro Ile Asp Gln Cys
625                 630                 635                 640

Ile Asp Gly

<210> SEQ ID NO 6
<211> LENGTH: 214
<212> TYPE: PRT
<213> ORGANISM: artificial
<220> FEATURE:
<223> OTHER INFORMATION: fusion polypeptide

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 7
<211> LENGTH: 640
<212> TYPE: PRT
<213> ORGANISM: artificial
<220> FEATURE:
<223> OTHER INFORMATION: fusion polypeptide

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

```
Val Gln Phe Asn Trp Tyr Val Asp Gly Val Glu Val His Asn Ala Lys
            275                 280                 285

Thr Lys Pro Arg Glu Glu Gln Phe Ala Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys Gly
    435                 440                 445

Gly Gly Gly Ser Gly Gly Gly Gly Ser Gly Gly Gly Gly Ser Gln Asp
450                 455                 460

Ser Thr Ser Asp Leu Ile Pro Ala Pro Pro Leu Ser Lys Val Pro Leu
465                 470                 475                 480

Gln Gln Asn Phe Gln Asp Asn Gln Phe His Gly Lys Trp Tyr Val Val
                485                 490                 495

Gly Gln Ala Gly Asn Ile Arg Leu Arg Glu Asp Lys Asp Pro Ile Lys
            500                 505                 510

Met Met Ala Thr Ile Tyr Glu Leu Lys Glu Asp Lys Ser Tyr Asp Val
    515                 520                 525

Thr Met Val Lys Phe Asp Asp Lys Lys Cys Met Tyr Asp Ile Trp Thr
530                 535                 540

Phe Val Pro Gly Ser Gln Pro Gly Glu Phe Thr Leu Gly Lys Ile Lys
545                 550                 555                 560

Ser Phe Pro Gly His Thr Ser Ser Leu Val Arg Val Val Ser Thr Asn
                565                 570                 575

Tyr Asn Gln His Ala Met Val Phe Phe Lys Phe Val Phe Gln Asn Arg
            580                 585                 590

Glu Glu Phe Tyr Ile Thr Leu Tyr Gly Arg Thr Lys Glu Leu Thr Ser
    595                 600                 605

Glu Leu Lys Glu Asn Phe Ile Arg Phe Ser Lys Ser Leu Gly Leu Pro
610                 615                 620

Glu Asn His Ile Val Phe Pro Val Pro Ile Asp Gln Cys Ile Asp Gly
625                 630                 635                 640

<210> SEQ ID NO 8
<211> LENGTH: 214
<212> TYPE: PRT
<213> ORGANISM: artificial
<220> FEATURE:
<223> OTHER INFORMATION: fusion polypeptide

<400> SEQUENCE: 8
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 9
<211> LENGTH: 640
<212> TYPE: PRT
<213> ORGANISM: artificial
<220> FEATURE:
<223> OTHER INFORMATION: fusion polypeptide

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Lys Thr Tyr Thr Cys Asn Val Asp His Lys
    195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
        260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Gln Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
        420                 425                 430

His Asn His Tyr Thr Gln Lys Ser Leu Ser Leu Ser Leu Gly Lys Gly
    435                 440                 445

Gly Gly Gly Ser Gly Gly Gly Gly Ser Gly Gly Gly Gly Ser Gln Asp
450                 455                 460

Ser Thr Ser Asp Leu Ile Pro Ala Pro Pro Leu Ser Lys Val Pro Leu
465                 470                 475                 480

Gln Gln Asn Phe Gln Asp Asn Gln Phe His Gly Lys Trp Tyr Val Val
            485                 490                 495

Gly Gln Ala Gly Asn Ile Arg Leu Arg Glu Asp Lys Asp Pro Ile Lys
        500                 505                 510

Met Met Ala Thr Ile Tyr Glu Leu Lys Glu Asp Lys Ser Tyr Asp Val
    515                 520                 525

Thr Met Val Lys Phe Asp Asp Lys Lys Cys Met Tyr Asp Ile Trp Thr
530                 535                 540

Phe Val Pro Gly Ser Gln Pro Gly Glu Phe Thr Leu Gly Lys Ile Lys
545                 550                 555                 560

Ser Phe Pro Gly His Thr Ser Ser Leu Val Arg Val Val Ser Thr Asn
```

```
                    565                 570                 575
Tyr Asn Gln His Ala Met Val Phe Phe Lys Phe Val Phe Gln Asn Arg
                580                 585                 590

Glu Glu Phe Tyr Ile Thr Leu Tyr Gly Arg Thr Lys Glu Leu Thr Ser
            595                 600                 605

Glu Leu Lys Glu Asn Phe Ile Arg Phe Ser Lys Ser Leu Gly Leu Pro
        610                 615                 620

Glu Asn His Ile Val Phe Pro Val Pro Ile Asp Gln Cys Ile Asp Gly
625                 630                 635                 640

<210> SEQ ID NO 10
<211> LENGTH: 214
<212> TYPE: PRT
<213> ORGANISM: artificial
<220> FEATURE:
<223> OTHER INFORMATION: fusion polypeptide

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 11
<211> LENGTH: 447
<212> TYPE: PRT
<213> ORGANISM: artificial
<220> FEATURE:
<223> OTHER INFORMATION: fusion polypeptide

<400> SEQUENCE: 11

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Asn Ile Lys Asp Thr
        20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
```

<210> SEQ ID NO 12
<211> LENGTH: 407
<212> TYPE: PRT
<213> ORGANISM: artificial
<220> FEATURE:
<223> OTHER INFORMATION: fusion polypeptide

<400> SEQUENCE: 12

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Gly Gly Gly Gly Ser Gln Asp Ser Thr Ser Asp Leu Ile Pro Ala Pro
225                 230                 235                 240

Pro Leu Ser Lys Val Pro Leu Gln Gln Asn Phe Gln Asp Asn Gln Phe
                245                 250                 255

His Gly Lys Trp Tyr Val Val Gly Gln Ala Gly Asn Ile Arg Leu Arg
            260                 265                 270

Glu Asp Lys Asp Pro Ile Lys Met Met Ala Thr Ile Tyr Glu Leu Lys
        275                 280                 285

Glu Asp Lys Ser Tyr Asp Val Thr Met Val Lys Phe Asp Asp Lys Lys
    290                 295                 300

Cys Met Tyr Asp Ile Trp Thr Phe Val Pro Gly Ser Gln Pro Gly Glu
305                 310                 315                 320

Phe Thr Leu Gly Lys Ile Lys Ser Phe Pro Gly His Thr Ser Ser Leu
                325                 330                 335

Val Arg Val Val Ser Thr Asn Tyr Asn Gln His Ala Met Val Phe Phe
            340                 345                 350

Lys Phe Val Phe Gln Asn Arg Glu Glu Phe Tyr Ile Thr Leu Tyr Gly
```

```
                355                 360                 365
Arg Thr Lys Glu Leu Thr Ser Glu Leu Lys Glu Asn Phe Ile Arg Phe
370                 375                 380

Ser Lys Ser Leu Gly Leu Pro Glu Asn His Ile Val Phe Pro Val Pro
385                 390                 395                 400

Ile Asp Gln Cys Ile Asp Gly
                405

<210> SEQ ID NO 13
<211> LENGTH: 640
<212> TYPE: PRT
<213> ORGANISM: artificial
<220> FEATURE:
<223> OTHER INFORMATION: fusion polypeptide

<400> SEQUENCE: 13

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Gln Ala Gly Asn Ile Arg Leu Arg Glu Asp Lys Asp Pro
            35                  40                  45

Ile Lys Met Met Ala Thr Ile Tyr Glu Leu Lys Glu Asp Lys Ser Tyr
        50                  55                  60

Asp Val Thr Met Val Lys Phe Asp Lys Lys Cys Met Tyr Asp Ile
65                  70                  75                  80

Trp Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
        115                 120                 125

Asn Arg Glu Glu Phe Tyr Ile Thr Leu Tyr Gly Arg Thr Lys Glu Leu
130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Ser Gly Gly Gly Ser Gly Gly Gly Gly
            180                 185                 190

Ser Glu Val Gln Leu Val Glu Ser Gly Gly Leu Val Gln Pro Gly
        195                 200                 205

Gly Ser Leu Arg Leu Ser Cys Ala Ala Ser Gly Phe Asn Ile Lys Asp
210                 215                 220

Thr Tyr Ile His Trp Val Arg Gln Ala Pro Gly Lys Gly Leu Glu Trp
225                 230                 235                 240

Val Ala Arg Ile Tyr Pro Thr Asn Gly Tyr Thr Arg Tyr Ala Asp Ser
                245                 250                 255

Val Lys Gly Arg Phe Thr Ile Ser Ala Asp Thr Ser Lys Asn Thr Ala
            260                 265                 270

Tyr Leu Gln Met Asn Ser Leu Arg Ala Glu Asp Thr Ala Val Tyr Tyr
        275                 280                 285

Cys Ser Arg Trp Gly Gly Asp Gly Phe Tyr Ala Met Asp Tyr Trp Gly
290                 295                 300

Gln Gly Thr Leu Val Thr Val Ser Ser Ala Ser Thr Lys Gly Pro Ser
```

```
            305                 310                 315                 320
Val Phe Pro Leu Ala Pro Cys Ser Arg Ser Thr Ser Glu Ser Thr Ala
                    325                 330                 335

Ala Leu Gly Cys Leu Val Lys Asp Tyr Phe Pro Glu Pro Val Thr Val
                340                 345                 350

Ser Trp Asn Ser Gly Ala Leu Thr Ser Gly Val His Thr Phe Pro Ala
            355                 360                 365

Val Leu Gln Ser Ser Gly Leu Tyr Ser Leu Ser Ser Val Val Thr Val
        370                 375                 380

Pro Ser Ser Ser Leu Gly Thr Lys Thr Tyr Thr Cys Asn Val Asp His
385                 390                 395                 400

Lys Pro Ser Asn Thr Lys Val Asp Lys Arg Val Glu Ser Lys Tyr Gly
                405                 410                 415

Pro Pro Cys Pro Pro Cys Pro Ala Pro Glu Ala Ala Gly Gly Pro Ser
                420                 425                 430

Val Phe Leu Phe Pro Pro Lys Pro Lys Asp Thr Leu Met Ile Ser Arg
            435                 440                 445

Thr Pro Glu Val Thr Cys Val Val Val Asp Val Ser Gln Glu Asp Pro
        450                 455                 460

Glu Val Gln Phe Asn Trp Tyr Val Asp Gly Val Glu Val His Asn Ala
465                 470                 475                 480

Lys Thr Lys Pro Arg Glu Glu Gln Phe Asn Ser Thr Tyr Arg Val Val
                485                 490                 495

Ser Val Leu Thr Val Leu His Gln Asp Trp Leu Asn Gly Lys Glu Tyr
                500                 505                 510

Lys Cys Lys Val Ser Asn Lys Gly Leu Pro Ser Ser Ile Glu Lys Thr
            515                 520                 525

Ile Ser Lys Ala Lys Gly Gln Pro Arg Glu Pro Gln Val Tyr Thr Leu
        530                 535                 540

Pro Pro Ser Gln Glu Glu Met Thr Lys Asn Gln Val Ser Leu Thr Cys
545                 550                 555                 560

Leu Val Lys Gly Phe Tyr Pro Ser Asp Ile Ala Val Glu Trp Glu Ser
                565                 570                 575

Asn Gly Gln Pro Glu Asn Asn Tyr Lys Thr Thr Pro Pro Val Leu Asp
                580                 585                 590

Ser Asp Gly Ser Phe Phe Leu Tyr Ser Arg Leu Thr Val Asp Lys Ser
            595                 600                 605

Arg Trp Gln Glu Gly Asn Val Phe Ser Cys Ser Val Met His Glu Ala
        610                 615                 620

Leu His Asn His Tyr Thr Gln Lys Ser Leu Ser Leu Ser Leu Gly Lys
625                 630                 635                 640

<210> SEQ ID NO 14
<211> LENGTH: 214
<212> TYPE: PRT
<213> ORGANISM: artificial
<220> FEATURE:
<223> OTHER INFORMATION: fusion polypeptide

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
```

```
            35                  40                  45
Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 15
<211> LENGTH: 447
<212> TYPE: PRT
<213> ORGANISM: artificial
<220> FEATURE:
<223> OTHER INFORMATION: fusion polypeptide

<400> SEQUENCE: 15

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
         35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

```
            180             185             190
Ser Ser Ser Leu Gly Thr Lys Thr Tyr Thr Cys Asn Val Asp His Lys
        195             200             205

Pro Ser Asn Thr Lys Val Asp Lys Arg Val Glu Ser Lys Tyr Gly Pro
    210             215             220

Pro Cys Pro Pro Cys Pro Ala Pro Glu Ala Ala Gly Gly Pro Ser Val
225             230             235             240

Phe Leu Phe Pro Pro Lys Pro Lys Asp Thr Leu Met Ile Ser Arg Thr
            245             250             255

Pro Glu Val Thr Cys Val Val Val Asp Val Ser Gln Glu Asp Pro Glu
        260             265             270

Val Gln Phe Asn Trp Tyr Val Asp Gly Val Glu Val His Asn Ala Lys
    275             280             285

Thr Lys Pro Arg Glu Glu Gln Phe Asn Ser Thr Tyr Arg Val Val Ser
290             295             300

Val Leu Thr Val Leu His Gln Asp Trp Leu Asn Gly Lys Glu Tyr Lys
305             310             315             320

Cys Lys Val Ser Asn Lys Gly Leu Pro Ser Ser Ile Glu Lys Thr Ile
            325             330             335

Ser Lys Ala Lys Gly Gln Pro Arg Glu Pro Gln Val Tyr Thr Leu Pro
        340             345             350

Pro Ser Gln Glu Glu Met Thr Lys Asn Gln Val Ser Leu Thr Cys Leu
    355             360             365

Val Lys Gly Phe Tyr Pro Ser Asp Ile Ala Val Glu Trp Glu Ser Asn
370             375             380

Gly Gln Pro Glu Asn Asn Tyr Lys Thr Thr Pro Pro Val Leu Asp Ser
385             390             395             400

Asp Gly Ser Phe Phe Leu Tyr Ser Arg Leu Thr Val Asp Lys Ser Arg
            405             410             415

Trp Gln Glu Gly Asn Val Phe Ser Cys Ser Val Met His Glu Ala Leu
        420             425             430

His Asn His Tyr Thr Gln Lys Ser Leu Ser Leu Ser Leu Gly Lys
    435             440             445

<210> SEQ ID NO 16
<211> LENGTH: 407
<212> TYPE: PRT
<213> ORGANISM: artificial
<220> FEATURE:
<223> OTHER INFORMATION: fusion polypeptide

<400> SEQUENCE: 16

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Arg Leu Arg Glu Asp Lys Asp Pro
        35                  40                  45

Ile Lys Met Met Ala Thr Ile Tyr Glu Leu Lys Glu Asp Lys Ser Tyr
    50                  55                  60

Asp Val Thr Met Val Lys Phe Asp Asp Lys Lys Cys Met Tyr Asp Ile
65                  70                  75                  80

Trp Thr Phe Val Pro Gly Ser Gln Pro Gly Glu Phe Thr Leu Gly Lys
            85                  90                  95

Ile Lys Ser Phe Pro Gly His Thr Ser Ser Leu Val Arg Val Val Ser
```

```
              100                 105                 110
Thr Asn Tyr Asn Gln His Ala Met Val Phe Lys Phe Val Phe Gln
            115                 120                 125

Asn Arg Glu Glu Phe Tyr Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly Gly Gly Gly Gly Ser Gly Gly Gly Ser Gly Gly Gly Gly
                180                 185                 190

Ser Asp Ile Gln Met Thr Gln Ser Pro Ser Ser Leu Ser Ala Ser Val
            195                 200                 205

Gly Asp Arg Val Thr Ile Thr Cys Arg Ala Ser Gln Asp Val Asn Thr
            210                 215                 220

Ala Val Ala Trp Tyr Gln Gln Lys Pro Gly Lys Ala Pro Lys Leu Leu
225                 230                 235                 240

Ile Tyr Ser Ala Ser Phe Leu Tyr Ser Gly Val Pro Ser Arg Phe Ser
                245                 250                 255

Gly Ser Arg Ser Gly Thr Asp Phe Thr Leu Thr Ile Ser Ser Leu Gln
            260                 265                 270

Pro Glu Asp Phe Ala Thr Tyr Tyr Cys Gln Gln His Tyr Thr Thr Pro
            275                 280                 285

Pro Thr Phe Gly Gln Gly Thr Lys Val Glu Ile Lys Arg Thr Val Ala
            290                 295                 300

Ala Pro Ser Val Phe Ile Phe Pro Pro Ser Asp Glu Gln Leu Lys Ser
305                 310                 315                 320

Gly Thr Ala Ser Val Val Cys Leu Leu Asn Asn Phe Tyr Pro Arg Glu
                325                 330                 335

Ala Lys Val Gln Trp Lys Val Asp Asn Ala Leu Gln Ser Gly Asn Ser
            340                 345                 350

Gln Glu Ser Val Thr Glu Gln Asp Ser Lys Asp Ser Thr Tyr Ser Leu
            355                 360                 365

Ser Ser Thr Leu Thr Leu Ser Lys Ala Asp Tyr Glu Lys His Lys Val
370                 375                 380

Tyr Ala Cys Glu Val Thr His Gln Gly Leu Ser Ser Pro Val Thr Lys
385                 390                 395                 400

Ser Phe Asn Arg Gly Glu Cys
                405

<210> SEQ ID NO 17
<211> LENGTH: 158
<212> TYPE: PRT
<213> ORGANISM: artificial
<220> FEATURE:
<223> OTHER INFORMATION: wildtype hTlc

<400> SEQUENCE: 17

His His Leu Leu Ala Ser Asp Glu Glu Ile Gln Asp Val Ser Gly Thr
1               5                   10                  15

Trp Tyr Leu Lys Ala Met Thr Val Asp Arg Glu Phe Pro Glu Met Asn
                20                  25                  30

Leu Glu Ser Val Thr Pro Met Thr Leu Thr Thr Leu Glu Gly Gly Asn
            35                  40                  45

Leu Glu Ala Lys Val Thr Met Leu Ile Ser Gly Arg Cys Gln Glu Val
```

```
                50                  55                  60
Lys Ala Val Leu Glu Lys Thr Asp Glu Pro Gly Lys Tyr Thr Ala Asp
 65                  70                  75                  80

Gly Gly Lys His Val Ala Tyr Ile Ile Arg Ser His Val Lys Asp His
                 85                  90                  95

Tyr Ile Phe Tyr Cys Glu Gly Glu Leu His Gly Lys Pro Val Arg Gly
                100                 105                 110

Val Lys Leu Val Gly Arg Asp Pro Lys Asn Asn Leu Glu Ala Leu Glu
            115                 120                 125

Asp Phe Glu Lys Ala Ala Gly Ala Arg Gly Leu Ser Thr Glu Ser Ile
        130                 135                 140

Leu Ile Pro Arg Gln Ser Glu Thr Cys Ser Pro Gly Ser Asp
145                 150                 155
```

<210> SEQ ID NO 18
<211> LENGTH: 178
<212> TYPE: PRT
<213> ORGANISM: artificial
<220> FEATURE:
<223> OTHER INFORMATION: wildtype hNGAL

<400> SEQUENCE: 18

```
Gln Asp Ser Thr Ser Asp Leu Ile Pro Ala Pro Pro Leu Ser Lys Val
 1               5                  10                  15

Pro Leu Gln Gln Asn Phe Gln Asp Asn Gln Phe Gln Gly Lys Trp Tyr
                20                  25                  30

Val Val Gly Leu Ala Gly Asn Ala Ile Leu Arg Glu Asp Lys Asp Pro
            35                  40                  45

Gln Lys Met Tyr Ala Thr Ile Tyr Glu Leu Lys Glu Asp Lys Ser Tyr
        50                  55                  60

Asn Val Thr Ser Val Leu Phe Arg Lys Lys Lys Cys Asp Tyr Trp Ile
 65                  70                  75                  80

Arg Thr Phe Val Pro Gly Cys Gln Pro Gly Glu Phe Thr Leu Gly Asn
                 85                  90                  95

Ile Lys Ser Tyr Pro Gly Leu Thr Ser Tyr Leu Val Arg Val Val Ser
                100                 105                 110

Thr Asn Tyr Asn Gln His Ala Met Val Phe Phe Lys Lys Val Ser Gln
            115                 120                 125

Asn Arg Glu Tyr Phe Lys Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 19
<211> LENGTH: 15
<212> TYPE: PRT
<213> ORGANISM: artificial
<220> FEATURE:
<223> OTHER INFORMATION: linker

<400> SEQUENCE: 19

```
Gly Gly Gly Gly Ser Gly Gly Gly Ser Gly Gly Gly Gly Ser
 1               5                  10                  15
```

<210> SEQ ID NO 20
<211> LENGTH: 1929
<212> TYPE: DNA
<213> ORGANISM: artificial
<220> FEATURE:
<223> OTHER INFORMATION: fusion polypeptide

<400> SEQUENCE: 20

| | | | | | |
|---|---|---|---|---|---|
| gaagtccagc | tggtcgaatc | tggtggtggc | ctggtccagc | ctggtggatc | actgagactg | 60 |
| tcctgtgctg | cttctggttt | caacatcaag | gacacctaca | tccattgggt | cagacaggca | 120 |
| cctggcaagg | gactggaatg | ggtcgcccga | atctacccta | caaacggcta | cactcgctac | 180 |
| gccgactccg | tcaagggacg | ctttaccatc | tccgccgaca | cctctaaaaa | caccgcctac | 240 |
| ctgcagatga | atagtctgag | ggccgaggat | actgctgtgt | actactgctc | acgatgggga | 300 |
| ggcgacggct | tttacgctat | ggattactgg | ggacagggaa | ctctggtcac | tgtgtctagc | 360 |
| gctagcacaa | agggccctag | tgtgtttcct | ctggctccct | cttccaaatc | cacttctggt | 420 |
| ggcactgctg | ctctgggatg | cctggtgaag | gattactttc | ctgaacctgt | gactgtctca | 480 |
| tggaactctg | gtgctctgac | ttctggtgtc | cacactttcc | ctgctgtgct | gcagtctagt | 540 |
| ggactgtact | ctctgtcatc | tgtggtcact | gtgccctctt | catctctggg | aacccagacc | 600 |
| tacatttgta | atgtgaacca | caaaccatcc | aacactaaag | tggacaaaaa | agtggaaccc | 660 |
| aaatcctgtg | acaaaaccca | cacctgccca | ccttgtcctg | ccctgaact | gctgggagga | 720 |
| ccttctgtgt | ttctgttccc | accaaaaacca | aaagatacccc | tgatgatctc | tagaaccct | 780 |
| gaggtgacat | gtgtggtggt | ggatgtgtct | catgaggacc | ctgaggtcaa | attcaactgg | 840 |
| tacgtggatg | gagtggaagt | ccacaatgcc | aaaaccaagc | ctagagagga | acagtacaat | 900 |
| tcaacctaca | gagtggtcag | tgtgctgact | gtgctgcatc | aggattggct | gaatggcaag | 960 |
| gaatacaagt | gtaaagtctc | aaacaaggcc | ctgcctgctc | caattgagaa | aacaatctca | 1020 |
| aaggccaagg | gacagcctag | gaaccccag | gtctacaccc | tgccaccttc | aagagaggaa | 1080 |
| atgaccaaaa | accaggtgtc | cctgacatgc | ctggtcaaag | gcttctaccc | ttctgacatt | 1140 |
| gctgtggagt | gggagtcaaa | tggacagcct | gagaacaact | acaaaacaac | cccccctgtg | 1200 |
| ctggattctg | atggctcttt | cttctctgtac | tccaaactga | ctgtggacaa | gtctagatgg | 1260 |
| cagcagggga | atgtcttttc | ttgctctgtc | atgcatgagg | ctctgcataa | ccactacact | 1320 |
| cagaaatccc | tgtctctgtc | tcctggcaaa | ggcggcggag | gatccggggg | tgggggaagc | 1380 |
| ggcggaggag | gtagccagga | ctctactagt | gatctgatcc | cggcaccgcc | actgtcaaaa | 1440 |
| gtccctctgc | aacaaaactt | tcaagacaat | cagtttcacg | gcaaatggta | tgtggtcggc | 1500 |
| caggccggaa | acattaggct | gcgggaggac | aaggacccca | tcaaaatgat | ggctaccatc | 1560 |
| tacgagctga | aggaagacaa | atcttatgat | gtgacaatgg | tcaagttcga | cgataagaaa | 1620 |
| tgcatgtacg | acatctggac | cttcgtgccc | ggctcccagc | cgggagagtt | caccctgggc | 1680 |
| aagatcaagt | cctcccccgg | ccacacttcc | agcctggtcc | gcgtggtctc | gaccaactat | 1740 |
| aatcagcatg | ctatggtgtt | cttcaagttc | gtctttcaga | atagagagga | gttctacatc | 1800 |
| acactgtatg | gacgcaccaa | ggagctgaca | agcgagctga | agaaaacctt | catcaggttt | 1860 |
| tcaaagtccc | tggggctgcc | cgaaaatcat | atcgtgttcc | cagtccccat | cgaccagtgt | 1920 |
| attgatggt | | | | | 1929 |

<210> SEQ ID NO 21
<211> LENGTH: 642
<212> TYPE: DNA

<213> ORGANISM: artificial
<220> FEATURE:
<223> OTHER INFORMATION: fusion polypeptide

<400> SEQUENCE: 21

| | | | | | |
|---|---|---|---|---|---|
| gacatccaga | tgacacagtc | tccctcttcc | ctgtccgctt | ctgtgggcga | tcgagtgaca | 60 |
| atcacctgta | gggctagtca | ggatgtgaat | actgctgttg | cttggtacca | gcagaaacca | 120 |
| ggaaaagccc | ctaaactgct | gatctactct | gcctcattcc | tgtactctgg | ggtgccttct | 180 |
| cgattcagtg | gttctagatc | tggcaccgat | ttcacactga | ccatttcttc | actgcaacct | 240 |
| gaggattttg | ccacctacta | ctgtcagcag | cactacacaa | cacctcccac | atttggccag | 300 |
| ggcacaaaag | tggagatcaa | acggaccgtg | gcggcgcctt | ctgtgttcat | tttccccca | 360 |
| tctgatgaac | agctgaaatc | tggcactgct | tctgtggtct | gtctgctgaa | caacttctac | 420 |
| cctagagagg | ccaaagtcca | gtggaaagtg | gacaatgctc | tgcagagtgg | gaattcccag | 480 |
| gaatctgtca | ctgagcagga | ctctaaggat | agcacatact | ccctgtcctc | tactctgaca | 540 |
| ctgagcaagg | ctgattacga | gaaacacaaa | gtgtacgcct | gtgaagtcac | acatcagggg | 600 |
| ctgtctagtc | ctgtgaccaa | atccttcaat | aggggagagt | gc | | 642 |

<210> SEQ ID NO 22
<211> LENGTH: 1920
<212> TYPE: DNA
<213> ORGANISM: artificial
<220> FEATURE:
<223> OTHER INFORMATION: fusion polypeptide

<400> SEQUENCE: 22

| | | | | | |
|---|---|---|---|---|---|
| gaagtccagc | tggtcgaatc | tggtggtggc | ctggtccagc | ctggtggatc | actgagactg | 60 |
| tcctgtgctg | cttctggttt | caacatcaag | gacacctaca | tccattgggt | cagacaggca | 120 |
| cctggcaagg | gactggaatg | ggtcgcccga | atctacccta | caaacggcta | cactcgctac | 180 |
| gccgactccg | tcaagggacg | ctttaccatc | tccgccgaca | cctctaaaaa | caccgcctac | 240 |
| ctgcaaatga | atagtctgag | ggccgaggat | actgctgtgt | actactgctc | acgatgggga | 300 |
| ggcgacggct | tttacgctat | ggattactgg | ggacagggaa | ctctggtcac | tgtctcgagc | 360 |
| gctagcacca | agggcccctc | cgtgttcccc | ctggcccctt | gctccggtc | cacctccgag | 420 |
| tctaccgccg | ctctgggctg | cctggtgaaa | gactacttcc | ccgagcctgt | gaccgtgagc | 480 |
| tggaactctg | gcgccctgac | ctccggcgtg | cacaccttcc | ctgccgtgct | gcaatcctcc | 540 |
| ggcctgtact | ccctgtcctc | cgtggtgaca | gtgccctcct | ccagcctggg | caccaagacc | 600 |
| tacacctgta | acgtggacca | caagccctcc | aacaccaagg | tggacaagcg | ggtggaatct | 660 |
| aaatacggcc | ctccctgccc | ccctgccct | gccctgaag | cggcgggcgg | accttccgtg | 720 |
| tttctgttcc | ccccaaagcc | caaggacacc | ctgatgatct | cccggacccc | cgaagtgacc | 780 |
| tgcgtggtgg | tggacgtgtc | ccaggaagat | ccagaggtgc | agttcaactg | gtatgttgac | 840 |
| ggcgtggaag | tgcacaacgc | caagaccaag | cccagagagg | aacagttcgc | ctccacctac | 900 |
| cgggtggtgt | ccgtgctgac | cgtgctgcac | caggactggc | tgaacggcaa | agagtacaag | 960 |
| tgcaaggtgt | ccaacaaggg | cctgcccctcc | agcatcgaaa | agaccatctc | caaggccaag | 1020 |
| ggccagcccc | gcgagcccca | ggtgtacacc | ctgcccccta | gccaggaaga | gatgaccaag | 1080 |
| aaccaggtgt | ccctgacctg | tctggtgaaa | ggcttctacc | cctccgacat | tgccgtggaa | 1140 |
| tgggagtcca | acggccagcc | cgagaacaac | tacaagacca | ccccccctgt | gctggactcc | 1200 |
| gacggctcct | tcttcctgta | ctctcggctg | acagtggata | agtcccggtg | gcaggaaggc | 1260 |

```
aatgtgttct cctgcagcgt gatgcacgag gccctgcaca accactatac ccagaagtcc    1320
ctgtccctga gcctgggcaa gggcggtgga ggatccgggg gtgggggaag cggcggagga    1380
ggtagccagg actctactag tgatctgatc ccggcaccgc cactgtcaaa agtccctctg    1440
caacaaaact ttcaagacaa tcagtttcac ggcaaatggt atgtggtcgg ccaggccgga    1500
aacattaggc tgcgggagga caaggacccc atcaaaatga tggctaccat ctacgagctg    1560
aaggaagaca aatcttatga tgtgacaatg gtcaagttcg acgataagaa atgcatgtac    1620
gacatctgga ccttcgtgcc cggctcccag ccgggagagt tcaccctggg caagatcaag    1680
tccttccccg ccacacttc cagcctggtc cgcgtggtct cgaccaacta taatcagcat    1740
gctatggtgt tcttcaagtt cgtctttcag aatagagagg agttctacat cacactgtat    1800
ggacgcacca aggagctgac aagcgagctg aaagaaaact tcatcaggtt ttcaaagtcc    1860
ctggggctgc ccgaaaatca tatcgtgttc ccagtcccca tcgaccagtg tattgatggt    1920

<210> SEQ ID NO 23
<211> LENGTH: 642
<212> TYPE: DNA
<213> ORGANISM: artificial
<220> FEATURE:
<223> OTHER INFORMATION: fusion polypeptide

<400> SEQUENCE: 23
gacatccaga tgacacagtc tccctcttcc ctgtccgctt ctgtgggcga tcgagtgaca      60
atcacctgta gggctagtca ggatgtgaat actgctgttg cttggtacca gcagaaacca     120
ggaaaagccc ctaaactgct gatctactct gcctcattcc tgtactctgg ggtgccttct     180
cgattcagtg gttctagatc tggcaccgat ttcacactga ccatttcttc actgcaacct     240
gaggattttg ccacctacta ctgtcagcag cactacacaa cacctcccac atttggccag     300
ggcacaaaag tggagatcaa acggaccgtg gcggcgcctt ctgtgttcat tttccccca      360 tctgatgaac agctgaaatc tggcactgct tctgtggtct gtctgctgaa caacttctac     420
cctagagagg ccaaagtcca gtggaaagtg acaatgctc tgcagagtgg gaattcccag     480
gaatctgtca ctgagcagga ctctaaggat agcacatact ccctgtcctc tactctgaca     540
ctgagcaagg ctgattacga aaacacaaa gtgtacgcct gtgaagtcac acatcagggg     600
ctgtctagtc ctgtgaccaa atccttcaat aggggagagt gc                       642

<210> SEQ ID NO 24
<211> LENGTH: 1920
<212> TYPE: DNA
<213> ORGANISM: artificial
<220> FEATURE:
<223> OTHER INFORMATION: fusion polypeptide

<400> SEQUENCE: 24
gaagtccagc tggtcgaatc tggtggtggc ctggtccagc tggtggatc actgagactg       60 tcctgtgctg cttctggttt caacatcaag gacacctaca tccattgggt cagacaggca     120
cctggcaagg gactggaatg ggtcgcccga atctacccta caaacggcta cactcgctac     180
gccgactccg tcaagggacg ctttaccatc tccgccgaca cctctaaaaa caccgcctac     240
ctgcaaatga atagtctgag ggccgaggat actgctgtgt actactgctc acgatgggga     300
ggcgacggct tttacgctat ggattactgg ggacagggaa ctctggtcac tgtctcgagc     360
gctagcacca agggcccctc cgtgttcccc ctggcccctt gctccggtc cacctccgag     420
```

```
tctaccgccg ctctgggctg cctggtgaaa gactacttcc ccgagcctgt gaccgtgagc      480
tggaactctg gcgccctgac ctccggcgtg cacaccttcc ctgccgtgct gcaatcctcc      540
ggcctgtact ccctgtcctc cgtggtgaca gtgccctcct ccagcctggg caccaagacc      600
tacacctgta acgtggacca caagccctcc aacaccaagg tggacaagcg ggtggaatct      660
aaatacggcc ctcccctgccc ccctgccct gcccctgaag cggcgggcgg accttccgtg      720
tttctgttcc ccccaaagcc caaggacacc ctgatgatct cccggacccc cgaagtgacc      780
tgcgtggtgg tggacgtgtc ccaggaagat ccagaggtgc agttcaactg gtatgttgac      840
ggcgtggaag tgcacaacgc caagaccaag cccagagagg aacagttcaa ctccacctac      900
cgggtggtgt ccgtgctgac cgtgctgcac caggactggc tgaacggcaa agagtacaag      960
tgcaaggtgt ccaacaaggg cctgccctcc agcatcgaaa agaccatctc caaggccaag     1020
ggccagcccc gcgagcccca ggtgtacacc ctgcccccta gccaggaaga gatgaccaag     1080
aaccaggtgt ccctgacctg tctggtgaaa ggcttctacc cctccgacat tgccgtggaa     1140
tgggagtcca acggccagcc cgagaacaac tacaagacca ccccccctgt gctggactcc     1200
gacggctcct tcttcctgta ctctcggctg acagtggata gtcccggtg gcaggaaggc     1260 aatgtgttct cctgcagcgt gatgcacgag gccctgcaca accactatac ccagaagtcc     1320
ctgtccctga gcctgggcaa gggcggtgga ggatccgggg gtgggggaag cggcggagga     1380
ggtagccagg actctactag tgatctgatc ccggcaccgc cactgtcaaa agtccctctg     1440
caacaaaact ttcaagacaa tcagtttcac ggcaaatggt atgtggtcgg ccaggccgga     1500
aacattaggc tgcgggagga caaggacccc atcaaaatga tggctaccat ctacgagctg     1560
aaggaagaca aatcttatga tgtgacaatg gtcaagttcg acgataagaa atgcatgtac     1620
gacatctgga ccttcgtgcc cggctcccag ccgggagagt tcacccctggg caagatcaag     1680 tccttccccg gccacacttc cagcctggtc gcgcgtggtct cgaccaacta taatcagcat     1740
gctatggtgt tcttcaagtt cgtctttcag aatagagagg agttctacat cacactgtat     1800
ggacgcacca aggagctgac aagcgagctg aaagaaaact tcatcaggtt ttcaaagtcc     1860
ctggggctgc ccgaaaatca tatcgtgttc ccagtcccca tcgaccagtg tattgatggt     1920
```

<210> SEQ ID NO 25
<211> LENGTH: 642
<212> TYPE: DNA
<213> ORGANISM: artificial
<220> FEATURE:
<223> OTHER INFORMATION: fusion polypeptide

<400> SEQUENCE: 25

```
gacatccaga tgacacagtc tccctcttcc ctgtccgctt ctgtgggcga tcgagtgaca       60
atcacctgta gggctagtca ggatgtgaat actgctgttg cttggtacca gcagaaacca      120
ggaaaagccc ctaaactgct gatctactct gcctcattcc tgtactctgg ggtgccttct      180
cgattcagtg gttctagatc tggcaccgat ttcacactga ccatttcttc actgcaacct      240
gaggattttg ccacctacta ctgtcagcag cactacacaa cacctcccac atttggccag      300
ggcacaaaag tggagatcaa acggaccgtg gcggcgcctt ctgtgttcat tttccccca       360 tctgatgaac agctgaaatc tggcactgct tctgtggtct gtctgctgaa caacttctac      420
cctagagagg ccaaagtcca gtggaaagtg gacaatgctc tgcagagtgg gaattcccag      480
gaatctgtca ctgagcagga ctctaaggat agcacatact ccctgtcctc tactctgaca      540
ctgagcaagg ctgattacga gaaacacaaa gtgtacgcct gtgaagtcac acatcagggg      600
```

```
ctgtctagtc ctgtgaccaa atccttcaat aggggagagt gc              642
```

<210> SEQ ID NO 26
<211> LENGTH: 1341
<212> TYPE: DNA
<213> ORGANISM: artificial
<220> FEATURE:
<223> OTHER INFORMATION: fusion polypeptide

<400> SEQUENCE: 26

```
gaagtccagc tggtcgaatc tggtggtggc ctggtccagc ctggtggatc actgagactg     60
tcctgtgctg cttctggttt caacatcaag gacacctaca tccattgggt cagacaggca    120
cctggcaagg gactggaatg ggtcgcccga atctacccta caaacggcta cactcgctac    180
gccgactccg tcaagggacg ctttaccatc tccgccgaca cctctaaaaa caccgcctac    240
ctgcaaatga atagtctgag ggccgaggat actgctgtgt actactgctc acgatgggga    300
ggcgacggct tttacgctat ggattactgg ggacagggaa ctctggtcac tgtctcgagc    360
gctagcacca agggcccctc cgtgttcccc ctggcccctt gctccggtc cacctccgag    420
tctaccgccg ctctgggctg cctggtgaaa gactacttcc ccgagcctgt gaccgtgagc    480
tggaactctg gcgccctgac ctccggcgtg cacaccttcc ctgccgtgct gcaatcctcc    540
ggcctgtact ccctgtcctc cgtggtgaca gtgccctcct ccagcctggg caccaagacc    600
tacacctgta acgtggacca caagccctcc aacaccaagg tggacaagcg ggtggaatct    660
aaatacggcc ctccctgccc ccctgccct gccctgaag cggcgggcgg accttccgtg    720
tttctgttcc ccccaaagcc caaggacacc ctgatgatct cccggacccc cgaagtgacc    780
tgcgtggtgg tggacgtgtc ccaggaagat ccagaggtgc agttcaactg gtatgttgac    840
ggcgtggaag tgcacaacgc caagaccaag cccagagagg aacagttcaa ctccacctac    900
cgggtggtgt ccgtgctgac cgtgctgcac caggactggc tgaacggcaa agagtacaag    960
tgcaaggtgt ccaacaaggg cctgccctcc agcatcgaaa agaccatctc caaggccaag   1020
ggccagcccc gcgagcccca ggtgtacacc ctgcccccta gccaggaaga gatgaccaag   1080
aaccaggtgt ccctgacctg tctggtgaaa ggcttctacc cctccgacat tgccgtggaa   1140
tgggagtcca acggccagcc cgagaacaac tacaagacca ccccccctgt gctggactcc   1200
gacggctcct tcttcctgta ctctcggctg acagtggata gtcccggtg caggaaggc   1260
aatgtgttct cctgcagcgt gatgcacgag gccctgcaca accactatac ccagaagtcc   1320
ctgtccctga gcctgggcaa g                                           1341
```

<210> SEQ ID NO 27
<211> LENGTH: 1062
<212> TYPE: DNA
<213> ORGANISM: artificial
<220> FEATURE:
<223> OTHER INFORMATION: fusion polypeptide

<400> SEQUENCE: 27

```
ctgtactctg gggtgccttc tcgattcagt ggttctagat ctggcaccga tttcacactg     60
accatttctt cactgcaacc tgaggatttt gccacctact actgtcagca gcactacaca    120
acacctccca catttggcca gggcacaaaa gtggagatca acggaccgt ggcggcgcct    180
tctgtgttca ttttccccc atctgatgaa cagctgaaat ctggcactgc ttctgtggtc    240
tgtctgctga acaacttcta ccctagagag gccaaagtcc agtggaaagt ggacaatgct    300
```

| | |
|---|---|
| ctgcagagtg ggaattccca ggaatctgtc actgagcagg actctaagga tagcacatac | 360 |
| tccctgtcct ctactctgac actgagcaag gctgattacg agaaacacaa agtgtacgcc | 420 |
| tgtgaagtca cacatcaggg gctgtctagt cctgtgacca atccttcaa taggggagag | 480 |
| tgcggcggcg gaggatccgg gggtggggga agcggcggag gaggtagcca ggactctact | 540 |
| agtgatctga tcccggcacc gccactgtca aaagtccctc tgcaacaaaa ctttcaagac | 600 |
| aatcagtttc acggcaaatg gtatgtggtc ggccaggccg gaaacattag gctgcgggag | 660 |
| gacaaggacc ccatcaaaat gatggctacc atctacgagc tgaaggaaga caaatcttat | 720 |
| gatgtgacaa tggtcaagtt cgacgataag aaatgcatgt acgacatctg gaccttcgtg | 780 |
| cccggctccc agccgggaga gttcaccctg gcaagatca agtccttccc cggccacact | 840 |
| tccagcctgg tccgcgtggt ctcgaccaac tataatcagc atgctatggt gttcttcaag | 900 |
| ttcgtctttc agaatagaga ggagttctac atcacactgt atggacgcac caaggagctg | 960 |
| acaagcgagc tgaaagaaaa cttcatcagg ttttcaaagt ccctggggct gcccgaaaat | 1020 |
| catatcgtgt tcccagtccc catcgaccag tgtattgatg gt | 1062 |

<210> SEQ ID NO 28
<211> LENGTH: 1920
<212> TYPE: DNA
<213> ORGANISM: artificial
<220> FEATURE:
<223> OTHER INFORMATION: fusion polypeptide

<400> SEQUENCE: 28

| | |
|---|---|
| caggactcta ctagtgatct gatcccggca ccgccactgt caaaagtccc tctgcaacaa | 60 |
| aactttcaag acaatcagtt tcacggcaaa tggtatgtgg tcggccaggc cggaaacatt | 120 |
| aggctgcggg aggacaagga ccccatcaaa atgatggcta ccatctacga gctgaaggaa | 180 |
| gacaaatctt atgatgtgac aatggtcaag ttcgacgata gaaatgcat gtacgacatc | 240 |
| tggaccttcg tgcccggctc ccagccggga gagttcaccc tggcaagat caagtccttc | 300 |
| cccggccaca cttccagcct ggtccgcgtg gtctcgacca actataatca gcatgctatg | 360 |
| gtgttcttca gttcgtctt tcagaataga ggagttct acatcacact gtatggacgc | 420 |
| accaaggagc tgacaagcga gctgaaagaa aacttcatca ggttttcaaa gtccctgggg | 480 |
| ctgcccgaaa atcatatcgt gttcccagtc cccatcgacc agtgtattga tggaggaggc | 540 |
| ggaggatccg gcggaggagg aagtggcgga ggaggaagtg aagtccagct ggtcgaatct | 600 |
| ggtggtggcc tggtccagcc tggtggatca ctgagactgt cctgtgctgc ttctggtttc | 660 |
| aacatcaagg acacctacat ccattgggtc agacaggcac ctggcaaggg actggaatgg | 720 |
| gtcgcccgaa tctaccctac aaacggctac actcgctacg ccgactccgt caagggacgc | 780 |
| tttaccatct ccgccgacac ctctaaaaac accgcctacc tgcagatgaa tagtctgagg | 840 |
| gccgaggata ctgctgtgta ctactgctca cgatggggag cgacggctt ttacgctatg | 900 |
| gattactggg gacagggaac tctggtcact gtgtctagcg ctagcaccaa gggcccctcc | 960 |
| gtgttccccc tggccccttg ctccggtcc acctccgagt ctaccgccgc tctgggctgc | 1020 |
| ctggtgaaag actactcc cgagcctgtg accgtgagct ggaactctgg cgccctgacc | 1080 |
| tccggcgtgc acaccttccc tgccgtgctg caatcctccg gcctgtactc cctgtcctcc | 1140 |
| gtggtgacag tgccctcctc cagcctgggc accaagacct acacctgtaa cgtggaccac | 1200 |
| aagccctcca caccaaggt ggacaagcgg gtggaatcta atacggcccc ccctgcccc | 1260 |
| ccctgccctg cccctgaagc ggcgggcgga ccttccgtgt ttctgttccc cccaaagccc | 1320 |

```
aaggacaccc tgatgatctc ccggaccccc gaagtgacct gcgtggtggt ggacgtgtcc   1380
caggaagatc cagaggtgca gttcaactgg tatgttgacg gcgtggaagt gcacaacgcc   1440
aagaccaagc ccagagagga acagttcaac tccacctacc gggtggtgtc cgtgctgacc   1500
gtgctgcacc aggactggct gaacggcaaa gagtacaagt gcaaggtgtc caacaagggc   1560 ctgcccctcca gcatcgaaaa gaccatctcc aaggccaagg ccagccccg cgagccccag    1620 gtgtacaccc tgcccctag ccaggaagag atgaccaaga accaggtgtc cctgacctgt    1680
ctggtgaaag cttctaccc ctccgacatt gccgtggaat gggagtccaa cggccagccc     1740
gagaacaact acaagaccac cccccctgtg ctggactccg acggctcctt cttcctgtac    1800
tctcggctga cagtggataa gtcccggtgg caggaaggca atgtgttctc ctgcagcgtg    1860
atgcacgagg ccctgcacaa ccactatacc cagaagtccc tgtccctgag cctgggcaag   1920

<210> SEQ ID NO 29
<211> LENGTH: 642
<212> TYPE: DNA
<213> ORGANISM: artificial
<220> FEATURE:
<223> OTHER INFORMATION: fusion polypeptide

<400> SEQUENCE: 29
gacatccaga tgacacagtc tccctcttcc ctgtccgctt ctgtgggcga tcgagtgaca     60
atcacctgta gggctagtca ggatgtgaat actgctgttg cttggtacca gcagaaacca    120
ggaaaagccc ctaaactgct gatctactct gcctcattcc tgtactctgg ggtgccttct    180
cgattcagtg gttctagatc tggcaccgat ttcacactga ccatttcttc actgcaacct    240
gaggattttg ccacctacta ctgtcagcag cactacacaa cacctcccac atttggccag    300
ggcacaaaag tggagatcaa acggaccgtg gcggcgcctt ctgtgttcat tttccccca     360 tctgatgaac agctgaaatc tggcactgct tctgtggtct gtctgctgaa caacttctac    420
cctagagagg ccaaagtcca gtggaaagtg gacaatgctc tgcagagtgg aattcccag    480 gaatctgtca ctgagcagga ctctaaggat agcacatact ccctgtcctc tactctgaca    540
ctgagcaagg ctgattacga gaaacacaaa gtgtacgcct gtgaagtcac acatcagggg   600
ctgtctagtc ctgtgaccaa atccttcaat aggggagagt gc                       642

<210> SEQ ID NO 30
<211> LENGTH: 1341
<212> TYPE: DNA
<213> ORGANISM: artificial
<220> FEATURE:
<223> OTHER INFORMATION: fusion polypeptide

<400> SEQUENCE: 30
gaagtccagc tggtcgaatc tggtggtggc ctggtccagc ctggtggatc actgagactg     60
tcctgtgctg cttctggttt caacatcaag gacacctaca tccattgggt cagacaggca    120
cctggcaagg gactggaatg ggtcgcccga atctacccta caaacggcta cactcgctac    180
gccgactccg tcaagggacg ctttaccatc tccgccgaca cctctaaaaa caccgcctac    240
ctgcaaatga atagtctgag ggccgaggat actgctgtgt actactgctc acgatgggga    300
ggcgacggct tttacgctat ggattactgg ggacagggaa ctctggtcac tgtctcgagc    360
gctagcacca agggccctc cgtgttccc ctggcccctt gctccggtc cacctccgag     420 tctaccgccg ctctgggctg cctggtgaaa gactacttcc ccgagcctgt gaccgtgagc    480
```

| | |
|---|---|
| tggaactctg gcgccctgac ctccggcgtg cacaccttcc ctgccgtgct gcaatcctcc | 540 |
| ggcctgtact ccctgtcctc cgtggtgaca gtgccctcct ccagcctggg caccaagacc | 600 |
| tacacctgta acgtggacca caagccctcc aacaccaagg tggacaagcg ggtggaatct | 660 |
| aaatacggcc ctccctgccc ccctgccct gccctgaag cggcgggcgg accttccgtg | 720 |
| tttctgttcc ccccaaagcc caaggacacc ctgatgatct cccggacccc cgaagtgacc | 780 |
| tgcgtggtgg tggacgtgtc ccaggaagat ccagaggtgc agttcaactg gtatgttgac | 840 |
| ggcgtggaag tgcacaacgc caagaccaag cccagagagg aacagttcaa ctccacctac | 900 |
| cgggtggtgt ccgtgctgac cgtgctgcac caggactggc tgaacggcaa agagtacaag | 960 |
| tgcaaggtgt ccaacaaggg cctgccctcc agcatcgaaa agaccatctc caaggccaag | 1020 |
| ggccagcccc gcgagcccca ggtgtacacc ctgcccccta gccaggaaga gatgaccaag | 1080 |
| aaccaggtgt ccctgacctg tctggtgaaa ggcttctacc cctccgacat tgccgtggaa | 1140 |
| tgggagtcca acggccagcc cgagaacaac tacaagacca cccccctgt gctggactcc | 1200 |
| gacggctcct tcttcctgta ctctcggctg acagtggata agtcccggtg gcaggaaggc | 1260 |
| aatgtgttct cctgcagcgt gatgcacgag gccctgcaca accactatac ccagaagtcc | 1320 |
| ctgtccctga gcctgggcaa g | 1341 |

<210> SEQ ID NO 31
<211> LENGTH: 1221
<212> TYPE: DNA
<213> ORGANISM: artificial
<220> FEATURE:
<223> OTHER INFORMATION: fusion polypeptide

<400> SEQUENCE: 31

| | |
|---|---|
| caggactcta ctagtgatct gatcccggca ccgccactgt caaaagtccc tctgcaacaa | 60 |
| aactttcaag acaatcagtt tcacggcaaa tggtatgtgg tcggccaggc cggaaacatt | 120 |
| aggctgcggg aggacaagga ccccatcaaa atgatggcta ccatctacga gctgaaggaa | 180 |
| gacaaatctt atgatgtgac aatggtcaag ttcgacgata gaaatgcat gtacgacatc | 240 |
| tggaccttcg tgcccggctc ccagccggga gagttcaccc tgggcaagat caagtccttc | 300 |
| cccggccaca cttccagcct ggtccgcgtg gtctcgacca actataatca gcatgctatg | 360 |
| gtgttcttca gttcgtcttt cagaatagag gaggagttct acatcacact gtatggacgc | 420 |
| accaaggagc tgacaagcga gctgaaagaa aacttcatca ggttttcaaa gtccctgggg | 480 |
| ctgcccgaaa atcatatcgt gttcccagtc cccatcgacc agtgtattga tggaggaggc | 540 |
| ggaggatccg gcggaggagg aagtggcgga ggaggaagtg acatccagat gacacagtct | 600 |
| ccctcttccc tgtccgcttc tgtgggcgat cgagtgacaa tcacctgtag gctagtcag | 660 |
| gatgtgaata tgctgttgc ttggtaccag cagaaaccag aaaagcccc taaactgctg | 720 |
| atctactctg cctcattcct gtactctggg gtgccttctc gattcagtgg ttctagatct | 780 |
| ggcaccgatt tcacactgac catttcttca ctgcaacctg aggattttgc cacctactac | 840 |
| tgtcagcagc actacacaac acctcccaca tttggccagg gcacaaaagt ggagatcaaa | 900 |
| cggaccgtgg cggcgccttc tgtgttcatt ttccccccat ctgatgaaca gctgaaatct | 960 |
| ggcactgctt ctgtggtctg tctgctgaac aacttctacc ctagagaggc caaagtccag | 1020 |
| tggaaagtgg acaatgctct gcagagtggg aattcccagg aatctgtcac tgagcaggac | 1080 |
| tctaaggata gcacatactc cctgtcctct actctgacac tgagcaaggc tgattacgag | 1140 |
| aaacacaaag tgtacgcctg tgaagtcaca catcaggggc tgtctagtcc tgtgaccaaa | 1200 | tccttcaata ggggagagtg c                                              1221

<210> SEQ ID NO 32
<211> LENGTH: 152
<212> TYPE: PRT
<213> ORGANISM: artificial
<220> FEATURE:
<223> OTHER INFORMATION: lipocalin mutein

<400> SEQUENCE: 32

Ala Ser Asp Glu Glu Ile Gln Asp Val Ser Gly Thr Trp Tyr Leu Lys
1               5                   10                  15

Ala Met Thr Val Asp Glu Gly Cys Arg Pro Trp Asn Ile Phe Ser Val
            20                  25                  30

Thr Pro Met Thr Leu Thr Thr Leu Glu Gly Gly Asn Leu Glu Ala Lys
        35                  40                  45

Val Thr Met Ala Ile Asp Gly Pro Ala Gln Glu Val Lys Ala Val Leu
    50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Val Cys Asp Gly Ser Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 33
<211> LENGTH: 152
<212> TYPE: PRT
<213> ORGANISM: artificial
<220> FEATURE:
<223> OTHER INFORMATION: lipocalin mutein

<400> SEQUENCE: 33

Thr Ser Asp Glu Glu Ile Gln Asp Val Ser Gly Thr Trp Tyr Leu Lys
1               5                   10                  15

Ala Met Thr Val Asp Glu Gly Cys Arg Pro Trp Asn Ile Phe Ser Val
            20                  25                  30

Thr Pro Met Thr Leu Thr Thr Leu Glu Gly Gly Asn Leu Glu Ala Lys
        35                  40                  45

Val Thr Met Ala Ile Asp Gly Pro Ala Gln Glu Val Arg Ala Val Leu
    50                  55                  60

Glu Lys Thr Asp Glu Pro Gly Lys Tyr Thr Ala Asp Gly Gly Lys His
65                  70                  75                  80

Asp Ala Tyr Ile Ile Arg Ser His Val Lys Asp His Tyr Ile Phe Tyr
                85                  90                  95

Ser Glu Gly Val Cys Asp Gly Ser Pro Val Pro Gly Val Trp Leu Val
            100                 105                 110

Gly Arg Asp Pro Glu Asn Asn Leu Glu Ala Leu Glu Asp Phe Glu Lys
        115                 120                 125

Thr Ala Gly Ala Arg Gly Leu Ser Thr Glu Ser Ile Leu Ile Pro Arg
    130                 135                 140

```
Gln Ser Glu Thr Ser Ser Pro Gly
145                 150

<210> SEQ ID NO 34
<211> LENGTH: 152
<212> TYPE: PRT
<213> ORGANISM: artificial
<220> FEATURE:
<223> OTHER INFORMATION: lipocalin mutein

<400> SEQUENCE: 34

Ala Ser Asp Glu Glu Ile Gln Asp Val Ser Gly Thr Trp Tyr Leu Lys
1               5                   10                  15

Ala Met Thr Val Asp Glu Gly Cys Arg Pro Trp Asn Ile Phe Ser Val
                20                  25                  30

Thr Pro Met Thr Leu Thr Thr Leu Glu Gly Gly Asn Leu Glu Ala Lys
            35                  40                  45

Val Thr Met Ala Ile Asp Gly Pro Ala Gln Glu Val Asn Ala Val Leu
50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Arg Asp His Tyr Ile Phe Tyr
                85                  90                  95

Ser Glu Gly Val Cys Asp Gly Ser Pro Val Pro Gly Val Trp Leu Val
            100                 105                 110

Gly Arg Asp Pro Glu Asn Asn Leu Glu Ala Leu Glu Asp Phe Glu Lys
        115                 120                 125

Thr Ala Gly Ala Arg Gly Leu Ser Thr Glu Ser Ile Leu Ile Pro Arg
    130                 135                 140

Gln Ser Glu Thr Ser Ser Pro Gly
145                 150

<210> SEQ ID NO 35
<211> LENGTH: 152
<212> TYPE: PRT
<213> ORGANISM: artificial
<220> FEATURE:
<223> OTHER INFORMATION: lipocalin mutein

<400> SEQUENCE: 35

Val Ser Asp Glu Glu Ile Gln Asp Val Ser Gly Thr Trp Tyr Leu Lys
1               5                   10                  15

Ala Met Thr Val Asp Glu Gly Cys Arg Pro Trp Asn Ile Phe Ser Val
                20                  25                  30

Thr Pro Met Thr Leu Thr Thr Leu Glu Gly Gly Asn Leu Glu Ala Lys
            35                  40                  45

Val Thr Met Ala Ile Asp Gly Pro Ala Gln Glu Val Arg Ala Val Leu
50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Glu Asp His Tyr Ile Phe Tyr
                85                  90                  95

Ser Glu Gly Val Cys Asp Gly Ser Pro Val Pro Gly Val Trp Leu Val
            100                 105                 110

Gly Arg Asp Pro Glu Asn Asn Leu Glu Ala Leu Glu Asp Phe Glu Lys
        115                 120                 125

Thr Ala Gly Ala Arg Gly Leu Ser Thr Glu Ser Ile Leu Ile Pro Arg
```

```
                130                 135                 140
Gln Ser Glu Thr Ser Ser Pro Gly
145                 150

<210> SEQ ID NO 36
<211> LENGTH: 152
<212> TYPE: PRT
<213> ORGANISM: artificial
<220> FEATURE:
<223> OTHER INFORMATION: lipocalin mutein

<400> SEQUENCE: 36

Ala Ser Asp Glu Glu Ile Gln Asp Val Ser Gly Thr Trp Tyr Leu Lys
1               5                   10                  15

Ala Met Thr Val Asp Glu Gly Cys Arg Pro Trp Asn Ile Phe Ser Val
                20                  25                  30

Thr Pro Met Thr Leu Ser Thr Leu Glu Gly Gly Asn Leu Glu Ala Lys
            35                  40                  45

Val Thr Met Ala Ile Asp Gly Pro Ala Gln Glu Val Lys Ala Val Leu
        50                  55                  60

Glu Lys Thr Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Val Cys Asp Gly Ser Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ile Glu Thr Ser Ser Pro Gly
145                 150

<210> SEQ ID NO 37
<211> LENGTH: 152
<212> TYPE: PRT
<213> ORGANISM: artificial
<220> FEATURE:
<223> OTHER INFORMATION: lipocalin mutein

<400> SEQUENCE: 37

Ala Ser Asp Glu Glu Ile Gln Asp Val Ser Gly Thr Trp Tyr Leu Lys
1               5                   10                  15

Ala Met Thr Val Asp Glu Gly Cys Arg Pro Trp Asn Ile Phe Ser Val
                20                  25                  30

Thr Pro Met Thr Leu Thr Thr Leu Glu Gly Gly Asn Leu Glu Ala Glu
            35                  40                  45

Val Thr Met Ala Ile Asp Gly Pro Ala Gln Glu Val Lys Ala Val Leu
        50                  55                  60

Glu Lys Ala Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Val Cys Asp Gly Ser Pro Val Pro Gly Val Trp Leu Val
            100                 105                 110

Gly Arg Asp Pro Lys Asn Asn Leu Glu Ala Leu Glu Asp Phe Glu Lys
        115                 120                 125
```

```
Thr Ala Gly Ala Arg Gly Leu Ser Thr Glu Ser Ile Leu Ile Pro Ser
            130                 135                 140

Gln Ile Glu Thr Ser Ser Pro Gly
145                 150

<210> SEQ ID NO 38
<211> LENGTH: 152
<212> TYPE: PRT
<213> ORGANISM: artificial
<220> FEATURE:
<223> OTHER INFORMATION: lipocalin mutein

<400> SEQUENCE: 38

Thr Ser Asp Glu Glu Ile Gln Asp Val Ser Gly Thr Trp Tyr Leu Lys
1               5                   10                  15

Ala Met Thr Val Asp Glu Gly Cys Arg Pro Trp Asn Ile Phe Ser Val
                20                  25                  30

Thr Pro Met Thr Leu Thr Thr Leu Glu Asp Gly Asn Leu Glu Ala Lys
            35                  40                  45

Val Thr Met Ala Ile Asp Gly Pro Ala Gln Glu Val Lys Ala Val Leu
    50                  55                  60

Glu Lys Ala Asp Glu Pro Gly Lys Tyr Thr Ala Asp Gly Gly Lys His
65                  70                  75                  80

Val Ala Tyr Ile Ile Arg Ser His Val Lys Asp His Tyr Ile Phe Tyr
                85                  90                  95

Ser Glu Gly Val Cys Asp Gly Ser Pro Val Pro Gly Val Trp Leu Val
            100                 105                 110

Gly Arg Asp Pro Lys Asn Asn Leu Glu Ala Leu Glu Asp Phe Glu Lys
        115                 120                 125

Ala Ala Gly Ala Arg Gly Leu Ser Thr Glu Ser Ile Leu Ile Pro Arg
    130                 135                 140

Gln Ile Glu Thr Ser Ser Pro Gly
145                 150

<210> SEQ ID NO 39
<211> LENGTH: 178
<212> TYPE: PRT
<213> ORGANISM: artificial
<220> FEATURE:
<223> OTHER INFORMATION: lipocalin mutein

<400> SEQUENCE: 39

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
                20                  25                  30

Val Val Gly Gln Ala Gly Asn Ile Lys Leu Arg Glu Lys Asp Pro
            35                  40                  45

Asn Lys Met Met Ala Thr Ile Tyr Glu Leu Lys Glu Asp Lys Ser Tyr
    50                  55                  60

Asn Val Thr Gly Val Thr Phe Asp Asp Lys Lys Cys Thr Tyr Ala Ile
65                  70                  75                  80

Ser Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
        115                 120                 125
```

-continued

```
Asn Arg Glu Glu Phe Tyr Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 40
<211> LENGTH: 178
<212> TYPE: PRT
<213> ORGANISM: artificial
<220> FEATURE:
<223> OTHER INFORMATION: lipocalin mutein

<400> SEQUENCE: 40

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Arg Leu Arg Glu Asp Lys Asp Pro
        35                  40                  45

Asn Lys Met Met Ala Thr Ile Tyr Glu Leu Lys Glu Asp Lys Ser Tyr
50                  55                  60

Asp Val Thr Ala Val Ala Phe Asp Asp Lys Lys Cys Thr Tyr Asp Ile
65                  70                  75                  80

Trp Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
        115                 120                 125

Asn Arg Glu Glu Phe Tyr Ile Thr Leu Tyr Gly Arg Thr Lys Glu Leu
            130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly
```

<210> SEQ ID NO 41
<211> LENGTH: 178
<212> TYPE: PRT
<213> ORGANISM: artificial
<220> FEATURE:
<223> OTHER INFORMATION: lipocalin muein

<400> SEQUENCE: 41

```
Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Lys Leu Arg Glu Asp Lys Asp Pro
        35                  40                  45

Asn Lys Met Met Ala Thr Ile Tyr Glu Leu Lys Glu Asp Lys Ser Tyr
50                  55                  60
```

```
Asp Val Thr Ala Val Ala Phe Asp Asp Lys Lys Cys Thr Tyr Asp Ile
 65                  70                  75                  80

Trp Thr Phe Val Pro Gly Ser Gln Pro Gly Glu Phe Thr Leu Gly Lys
                 85                  90                  95

Ile Lys Ser Phe Pro Gly His Thr Ser Ser Leu Val Arg Val Ser
                100                 105                 110

Thr Asn Tyr Asn Gln His Ala Met Val Phe Phe Lys Phe Val Phe Gln
            115                 120                 125

Asn Arg Glu Glu Phe Tyr Ile Thr Leu Tyr Gly Arg Thr Lys Glu Leu
        130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 42
<211> LENGTH: 175
<212> TYPE: PRT
<213> ORGANISM: artificial
<220> FEATURE:
<223> OTHER INFORMATION: lipocalin mutein

<400> SEQUENCE: 42

Gln Asp Ser Thr Ser Asp Leu Ile Pro Ala Pro Pro Leu Ser Lys Val
  1               5                  10                  15

Pro Leu Gln Gln Asn Phe Gln Asp Asn Gln Phe His Gly Lys Trp Tyr
                 20                  25                  30

Val Val Gly Gln Ala Gly Asn Ile Lys Leu Arg Glu Asp Ser Lys Met
             35                  40                  45

Met Ala Thr Ile Tyr Glu Leu Lys Glu Asp Lys Ser Tyr Asp Val Thr
 50                  55                  60

Gly Val Ser Phe Asp Asp Lys Lys Cys Thr Tyr Ala Ile Met Thr Phe
 65                  70                  75                  80

Val Pro Gly Ser Gln Pro Gly Glu Phe Thr Leu Gly Lys Ile Lys Ser
                 85                  90                  95

Phe Pro Gly His Thr Ser Ser Leu Val Arg Val Val Ser Thr Asn Tyr
                100                 105                 110

Asn Gln His Ala Met Val Phe Phe Lys Phe Val Phe Gln Asn Arg Glu
            115                 120                 125

Glu Phe Tyr Ile Thr Leu Tyr Gly Arg Thr Lys Glu Leu Thr Ser Glu
        130                 135                 140

Leu Lys Glu Asn Phe Ile Arg Phe Ser Lys Ser Leu Gly Leu Pro Glu
145                 150                 155                 160

Asn His Ile Val Phe Pro Val Pro Ile Asp Gln Cys Ile Asp Gly
                165                 170                 175

<210> SEQ ID NO 43
<211> LENGTH: 178
<212> TYPE: PRT
<213> ORGANISM: artificial
<220> FEATURE:
<223> OTHER INFORMATION: lipocalin mutein

<400> SEQUENCE: 43

Gln Asp Ser Thr Ser Asp Leu Ile Pro Ala Pro Pro Leu Ser Lys Val
  1               5                  10                  15
```

-continued

Pro Leu Gln Gln Asn Phe Gln Asp Asn Gln Phe His Gly Lys Trp Tyr
            20                  25                  30

Val Val Gly Gln Ala Gly Asn Ile Lys Leu Arg Glu Asp Lys Asp Pro
        35                  40                  45

Val Lys Met Met Ala Thr Ile Tyr Glu Leu Lys Glu Asp Lys Ser Tyr
    50                  55                  60

Asp Val Thr Gly Val Thr Phe Asp Asp Lys Lys Cys Arg Tyr Asp Ile
65                  70                  75                  80

Ser Thr Phe Val Pro Gly Ser Gln Pro Gly Glu Phe Thr Phe Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
        115                 120                 125

Asn Arg Glu Glu Phe Tyr Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 44
<211> LENGTH: 178
<212> TYPE: PRT
<213> ORGANISM: artificial
<220> FEATURE:
<223> OTHER INFORMATION: lipocalin mutein

<400> SEQUENCE: 44

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Arg Leu Arg Glu Asp Lys Asp Pro
        35                  40                  45

His Lys Met Met Ala Thr Ile Tyr Glu Leu Lys Glu Asp Lys Ser Tyr
    50                  55                  60

Asp Val Thr Gly Val Thr Phe Asp Asp Lys Lys Cys Thr Tyr Ala Ile
65                  70                  75                  80

Ser Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
        115                 120                 125

Asn Arg Glu Glu Phe Tyr Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 45

<211> LENGTH: 178
<212> TYPE: PRT
<213> ORGANISM: artificial
<220> FEATURE:
<223> OTHER INFORMATION: lipocalin mutein

<400> SEQUENCE: 45

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Lys Leu Arg Glu Asp Lys Asp Pro
        35                  40                  45

Asn Lys Met Met Ala Thr Ile Tyr Glu Leu Lys Glu Asp Lys Ser Tyr
    50                  55                  60

Asp Val Thr Gly Val Thr Phe Asp Asp Lys Lys Cys Thr Tyr Ala Ile
65                  70                  75                  80

Ser Thr Leu Val Pro Gly Ser Gln Pro Gly Glu Phe Thr Phe Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
        115                 120                 125

Asn Arg Glu Glu Phe Tyr Ile Thr Leu Tyr Gly Arg Thr Lys Glu Leu
    130                 135                 140

Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 46
<211> LENGTH: 178
<212> TYPE: PRT
<213> ORGANISM: artificial
<220> FEATURE:
<223> OTHER INFORMATION: lipocalin mutein

<400> SEQUENCE: 46

Gln Asp Ser Thr Ser Asp Leu Ile Pro Ala Pro Pro Leu Ser Lys Val
1               5                   10                  15

Pro Leu Gln Gln Asn Phe Gln Asp Asn Gln Phe His Gly Lys Trp Tyr
            20                  25                  30

Val Val Gly Gln Ala Gly Asn Ile Arg Leu Arg Glu Asp Lys Asp Pro
        35                  40                  45

Ser Lys Met Met Ala Thr Ile Tyr Glu Leu Lys Glu Asp Lys Ser Tyr
    50                  55                  60

Asp Val Thr Ala Val Thr Phe Asp Asp Lys Lys Cys Asn Tyr Ala Ile
65                  70                  75                  80

Ser Thr Phe Val Pro Gly Ser Gln Pro Gly Glu Phe Thr Leu Gly Lys
                85                  90                  95

Ile Lys Ser Phe Pro Gly His Thr Ser Ser Leu Val Arg Val Val Ser
            100                 105                 110

Thr Asn Tyr Asn Gln His Ala Met Val Phe Phe Lys Phe Val Phe Gln
        115                 120                 125

Asn Arg Glu Glu Phe Tyr Ile Thr Leu Tyr Gly Arg Thr Lys Glu Leu
    130                 135                 140

```
Thr Ser Glu Leu Lys Glu Asn Phe Ile Arg Phe Ser Lys Ser Leu Gly
145                 150                 155                 160

Leu Pro Glu Asn His Ile Val Phe Pro Val Pro Ile Asp Gln Cys Ile
                165                 170                 175

Asp Gly

<210> SEQ ID NO 47
<211> LENGTH: 448
<212> TYPE: PRT
<213> ORGANISM: artificial
<220> FEATURE:
<223> OTHER INFORMATION: reference antibody

<400> SEQUENCE: 47

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Ser Pro Glu Lys Gly Leu Glu Trp Ile
        35                  40                  45

Gly Glu Ile Asn His Gly Gly Tyr Val Thr Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Tyr Gly Pro Gly Asn Tyr Asp Trp Tyr Phe Asp Leu Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320
```

```
Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Gln Glu Glu Met Thr Lys Asn Gln Val Ser Leu Thr Cys
                355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly Lys
                435                 440                 445

<210> SEQ ID NO 48
<211> LENGTH: 216
<212> TYPE: PRT
<213> ORGANISM: artificial
<220> FEATURE:
<223> OTHER INFORMATION: reference antibody

<400> SEQUENCE: 48

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 49
<211> LENGTH: 442
```

```
<212> TYPE: PRT
<213> ORGANISM: artificial
<220> FEATURE:
<223> OTHER INFORMATION: reference antibody

<400> SEQUENCE: 49
```

| | | | | | | | | | | | | | | |
|---|---|---|---|---|---|---|---|---|---|---|---|---|---|---|
| Glu | Val | Gln | Leu | Val | Gln | Ser | Gly | Ala | Glu | Val | Lys | Lys | Pro | Gly | Glu |
| 1 | | | | 5 | | | | | 10 | | | | | 15 |
| Ser | Leu | Arg | Ile | Ser | Cys | Lys | Gly | Ser | Gly | Tyr | Ser | Phe | Ser | Thr | Tyr |
| | | | 20 | | | | | 25 | | | | | 30 | |
| Trp | Ile | Ser | Trp | Val | Arg | Gln | Met | Pro | Gly | Lys | Gly | Leu | Glu | Trp | Met |
| | | 35 | | | | | 40 | | | | | 45 | | |
| Gly | Lys | Ile | Tyr | Pro | Gly | Asp | Ser | Tyr | Thr | Asn | Tyr | Ser | Pro | Ser | Phe |
| 50 | | | | | 55 | | | | | 60 | | | | |
| Gln | Gly | Gln | Val | Thr | Ile | Ser | Ala | Asp | Lys | Ser | Ile | Ser | Thr | Ala | Tyr |
| 65 | | | | 70 | | | | | 75 | | | | | 80 |
| Leu | Gln | Trp | Ser | Ser | Leu | Lys | Ala | Ser | Asp | Thr | Ala | Met | Tyr | Tyr | Cys |
| | | | | 85 | | | | | 90 | | | | | 95 |
| Ala | Arg | Gly | Tyr | Gly | Ile | Phe | Asp | Tyr | Trp | Gly | Gln | Gly | Thr | Leu | Val |
| | | | 100 | | | | | 105 | | | | | 110 | |
| Thr | Val | Ser | Ser | Ala | Ser | Thr | Lys | Gly | Pro | Ser | Val | Phe | Pro | Leu | Ala |
| | | 115 | | | | | 120 | | | | | 125 | | |
| Pro | Cys | Ser | Arg | Ser | Thr | Ser | Glu | Ser | Thr | Ala | Ala | Leu | Gly | Cys | Leu |
| 130 | | | | | 135 | | | | | 140 | | | | |
| Val | Lys | Asp | Tyr | Phe | Pro | Glu | Pro | Val | Thr | Val | Ser | Trp | Asn | Ser | Gly |
| 145 | | | | 150 | | | | | 155 | | | | | 160 |
| Ala | Leu | Thr | Ser | Gly | Val | His | Thr | Phe | Pro | Ala | Val | Leu | Gln | Ser | Ser |
| | | | | 165 | | | | | 170 | | | | | 175 |
| Gly | Leu | Tyr | Ser | Leu | Ser | Ser | Val | Val | Thr | Val | Pro | Ser | Ser | Asn | Phe |
| | | | 180 | | | | | 185 | | | | | 190 | |
| Gly | Thr | Gln | Thr | Tyr | Thr | Cys | Asn | Val | Asp | His | Lys | Pro | Ser | Asn | Thr |
| | | 195 | | | | | 200 | | | | | 205 | | |
| Lys | Val | Asp | Lys | Thr | Val | Glu | Arg | Lys | Cys | Cys | Val | Glu | Cys | Pro | Pro |
| 210 | | | | | 215 | | | | | 220 | | | | |
| Cys | Pro | Ala | Pro | Pro | Val | Ala | Gly | Pro | Ser | Val | Phe | Leu | Phe | Pro | Pro |
| 225 | | | | 230 | | | | | 235 | | | | | 240 |
| Lys | Pro | Lys | Asp | Thr | Leu | Met | Ile | Ser | Arg | Thr | Pro | Glu | Val | Thr | Cys |
| | | | | 245 | | | | | 250 | | | | | 255 |
| Val | Val | Val | Asp | Val | Ser | His | Glu | Asp | Pro | Glu | Val | Gln | Phe | Asn | Trp |
| | | | 260 | | | | | 265 | | | | | 270 | |
| Tyr | Val | Asp | Gly | Val | Glu | Val | His | Asn | Ala | Lys | Thr | Lys | Pro | Arg | Glu |
| | | 275 | | | | | 280 | | | | | 285 | | |
| Glu | Gln | Phe | Asn | Ser | Thr | Phe | Arg | Val | Val | Ser | Val | Leu | Thr | Val | Val |
| 290 | | | | | 295 | | | | | 300 | | | | |
| His | Gln | Asp | Trp | Leu | Asn | Gly | Lys | Glu | Tyr | Lys | Cys | Lys | Val | Ser | Asn |
| 305 | | | | 310 | | | | | 315 | | | | | 320 |
| Lys | Gly | Leu | Pro | Ala | Pro | Ile | Glu | Lys | Thr | Ile | Ser | Lys | Thr | Lys | Gly |
| | | | | 325 | | | | | 330 | | | | | 335 |
| Gln | Pro | Arg | Glu | Pro | Gln | Val | Tyr | Thr | Leu | Pro | Pro | Ser | Arg | Glu | Glu |
| | | | 340 | | | | | 345 | | | | | 350 | |
| Met | Thr | Lys | Asn | Gln | Val | Ser | Leu | Thr | Cys | Leu | Val | Lys | Gly | Phe | Tyr |
| | | 355 | | | | | 360 | | | | | 365 | | |
| Pro | Ser | Asp | Ile | Ala | Val | Glu | Trp | Glu | Ser | Asn | Gly | Gln | Pro | Glu | Asn |
| 370 | | | | | 375 | | | | | 380 | | | | |

```
Asn Tyr Lys Thr Thr Pro Met Leu Asp Ser Asp Gly Ser Phe Phe
385                 390                 395                 400

Leu Tyr Ser Lys Leu Thr Val Asp Lys Ser Arg Trp Gln Gln Gly Asn
            405                 410                 415

Val Phe Ser Cys Ser Val Met His Glu Ala Leu His Asn His Tyr Thr
            420                 425                 430

Gln Lys Ser Leu Ser Leu Ser Pro Gly Lys
            435                 440

<210> SEQ ID NO 50
<211> LENGTH: 214
<212> TYPE: PRT
<213> ORGANISM: artificial
<220> FEATURE:
<223> OTHER INFORMATION: reference antibody

<400> SEQUENCE: 50

Ser Tyr Glu Leu Thr Gln Pro Pro Ser Val Ser Val Ser Pro Gly Gln
1               5                   10                  15

Thr Ala Ser Ile Thr Cys Ser Gly Asp Asn Ile Gly Asp Gln Tyr Ala
            20                  25                  30

His Trp Tyr Gln Gln Lys Pro Gly Gln Ser Pro Val Leu Val Ile Tyr
        35                  40                  45

Gln Asp Lys Asn Arg Pro Ser Gly Ile Pro Glu Arg Phe Ser Gly Ser
50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Ala Thr Tyr Thr Gly Phe Gly Ser Leu
                85                  90                  95

Ala Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 51
<211> LENGTH: 447
<212> TYPE: PRT
<213> ORGANISM: artificial
<220> FEATURE:
<223> OTHER INFORMATION: Trastuzumab-IgG4 S228P FALA (Heavy chain)

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30
```

```
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ser Arg Trp Gly Gly Asp Gly Phe Tyr Ala Met Asp Tyr Trp Gly Gln
                100                 105                 110
Gly Thr Leu Val Thr Val Ser Ser Ala Ser Thr Lys Gly Pro Ser Val
        115                 120                 125
Phe Pro Leu Ala Pro Cys Ser Arg Ser Thr Ser Glu Ser Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
        180                 185                 190
Ser Ser Ser Leu Gly Thr Lys Thr Tyr Thr Cys Asn Val Asp His Lys
        195                 200                 205
Pro Ser Asn Thr Lys Val Asp Lys Arg Val Glu Ser Lys Tyr Gly Pro
        210                 215                 220
Pro Cys Pro Pro Cys Pro Ala Pro Glu Ala Ala Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
        260                 265                 270
Val Gln Phe Asn Trp Tyr Val Asp Gly Val Glu Val His Asn Ala Lys
        275                 280                 285
Thr Lys Pro Arg Glu Glu Gln Phe Asn Ser Thr Tyr Arg Val Val Ser
        290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Gln Glu Glu Met Thr Lys Asn Gln Val Ser Leu Thr Cys Leu
        355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
                420                 425                 430
His Asn His Tyr Thr Gln Lys Ser Leu Ser Leu Ser Leu Gly Lys
        435                 440                 445
```

<210> SEQ ID NO 52
<211> LENGTH: 214
<212> TYPE: PRT
<213> ORGANISM: artificial
<220> FEATURE:
<223> OTHER INFORMATION: Trastuzumab-IgG4 S228P FALA (Light chain)

<400> SEQUENCE: 52

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

ANTI-CANCER FUSION POLYPEPTIDE

CROSS REFERENCE TO RELATED APPLICATIONS

The present application is a national stage entry of International Patent Application No. PCT/EP2016/060041, filed May 4, 2016, which claims priority to EP Patent Application No. 15166179.0 filed May 4, 2015, EP Patent Application No. 15167917.2 filed May 18, 2015, EP Patent Application No. 15002702.7 filed Sep. 17, 2015, EP Patent Application No. 15192870.2 filed Nov. 4, 2015, and EP Patent Application No. 16150705.8 filed Jan. 11, 2016, EP Patent Application No. 16000862.9 filed Apr. 15, 2015 each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Aug. 27, 2019, is named "2013101-0049 SL.txt" and is 119,507 bytes in size.

I. BACKGROUND

HER2/neu is a member of the human epidermal growth factor receptor family. Amplification or overexpression of this oncogene has been shown to play an important role in the development and progression of a variety of tumors, including certain aggressive types of breast cancer. HER2/neu has been shown to be highly differentially expressed on tumor cells with much higher cell-surface density compared to healthy tissue.

Trastuzumab (marketed as Herceptin®), a monoclonal antibody targeting HER2/neu, is indicated for the treatment of women with either early stage or metastatic HER2(+) breast cancer. Despite the promising activity of monoclonal antibodies such as Trastuzumab in this setting, the response rates among patients with either refractory or advanced cancer are suboptimal. For example, while the objective response rate rose significantly in a clinical trial comparing chemotherapy alone with chemotherapy plus Trastuzumab—from 32% to 50% —, this still left the other half of the enrolled patients having no response (Slamon D. J. et al., N Engl J Med. 2001 Mar. 15; 344(11):783-92). Therefore, better HER2/neu-targeting therapies with an improved response rate are required.

CD137 is a co-stimulatory immune receptor and a member of the tumor necrosis factor receptor (TNFR) superfamily. It is mainly expressed on activated CD4+ and CD8+ T cells, activated B cells, and natural killer (NK) cells but can also be found on resting monocytes and dendritic cells (Li, S. Y. et al., Clin Pharmacol 2013 5(Suppl 1):47-53), or endothelial cells (Snell, L. M. et al., Immunol Rev 2011 November; 244(1):197-217). CD137 plays an important role in the regulation of immune responses and thus is a target for cancer immunotherapy. CD137 ligand (CD137L) is the only known natural ligand of CD137, and is constitutively expressed on several types of APC, such as activated B cells, monocytes, and splenic dendritic cells, and it can be induced on T lymphocytes.

CD137L is a trimeric protein that exists as a membrane-bound form and as a soluble variant. The ability of soluble CD137L to activate CD137 e.g. on CD137-expressing lymphocytes is limited, however, and large concentrations are required to elicit an effect (Wyzgol, A. et al., J Immunol 2009 Aug. 1; 183(3):1851-1861). The natural way of activation of CD137 is via the engagement of a CD137-positive cell with a CD137L-positive cell. CD137 activation is then thought to be induced by clustering through CD137L on the opposing cell, leading to signaling via TRAF1, 2 and 3 (Snell, L. M. et al., Immunol Rev 2011 November; 244(1): 197-217, Yao, S. et al., Nat Rev Drug Disc 2013 February; 12(2):130-146) and further concomitant downstream effects in the CD137-positive T-cell. In the case of T-cells activated by recognition of their respective cognate targets, the effects elicited by costimulation of CD137 are a further enhanced activation, enhanced survival and proliferation, the production of pro-inflammatory cytokines and an improved capacity to kill.

The benefit of CD137 costimulation for the elimination of cancer cells has been demonstrated in a number of preclinical in-vivo models. The forced expression of CD137L on a tumor, for example, leads to tumor rejection (Melero, I. et al., Eur J Immunol 1998 March; 28(3):1116-1121). Likewise, the forced expression of an anti-CD137 scFv on a tumor leads to a CD4+ T-cell and NK-cell dependent elimination of the tumor (Ye, Z. et al., Nat Med 2002 April; 8(4):343-348, Zhang, H. et al., Mol Canc Ther 2006 January; 5(1):149-155, Yang, Y. et al., Canc Res 2007 Mar. 1; 67(5):2339-2344). A systemically administered anti-CD137 antibody has also been demonstrated to lead to retardation of tumor growth (Martinet, O. et al., Gene Ther 2002 June; 9(12):786-792).

It has been shown that CD137 is an excellent marker for naturally occurring tumor-reactive T cells in human tumors (Ye, Q. et al., Clin Canc Res: 2014 Jan. 1; 20(1):44-55), and that anti-CD137 antibodies can be employed to improve the expansion and activity of CD8+ melanoma tumor-infiltrating lymphocytes for the application in adoptive T-cell therapy (Chacon, J. A. et al., PloS One 2013 8(4):e60031).

The preclinical demonstration of the potential therapeutic benefit of CD137 costimulation has spurred the development of therapeutic antibodies targeting CD137, BMS-663513 (Jure-Kunkel, M. et al., U.S. Pat. No. 7,288,638) and PF-05082566 (Fisher, T. S. et al., Canc Immunol Immunother 2012 October; 61(10):1721-1733); both are currently in early clinical trials.

However, it has only recently been appreciated that a bivalent CD137-binder like an antibody may by itself not be sufficient to cluster CD137 on T-cells or NK-cells and lead to efficient activation, in analogy to the lack of activity of the trivalent soluble CD137L. In recent publications utilizing preclinical mouse models, in-vivo evidence has been presented that the mode of action of other anti-TNFR antibodies in fact requires the interaction of the antibodies via their Fc-part with Fc-gamma receptors on Fc-gamma-receptor expressing cells (Bulliard, Y. et al., J Exp Med 2013 Aug. 26; 210(9):1685-1693, Bulliard, Y. et al., Immunol Cell Biol 2014 July; 92(6):475-480). The mode of action of the antibodies currently in clinical development may therefore be dominated by a non-targeted clustering via Fc-gamma receptors which may be nearly randomly dependent on the presence of Fc-γ-expressing cells in the vicinity of the tumor.

Thus, there is unmet need for the generation of therapeutics that cluster and activate CD137 with a specific tumor-targeted mode of action.

To meet this unmet need, the present application, provides a novel approach of simultaneously engaging CD137 and tumor antigen HER2/neu via a fusion polypeptide having the following properties:

(a) binding specificity for CD137; and
(b) binding specificity for HER2/neu;

This fusion polypeptide is designed to provide a tumor-target-dependent activation of CD137 on lymphocytes, via HER2 overexpressed on tumor cells. Such a molecule is expected to further activate T-cells and/or NK cells that are located in the vicinity of a HER2-positive tumor. Such a bispecific may display improved therapeutic effects over either anti-HER2 or anti-CD137 antibodies.

II. DEFINITIONS

The following list defines terms, phrases, and abbreviations used throughout the instant specification. All terms listed and defined herein are intended to encompass all grammatical forms.

As used herein, unless otherwise specified, "CD137" means human CD137. CD137 is also known as "4-1BB" or "tumor necrosis factor receptor superfamily member 9 (TN-FRSF9)" or "induced by lymphocyte activation (ILA)". Human CD137 means a full-length protein defined by UniProt Q07011, a fragment thereof, or a variant thereof.

As used herein, unless otherwise specified, "HER2" or "HER2/neu" means human HER2. Her-2 or HER2/neu is also known as "erbB-2", "c-neu", or "p185". Human Her 2 means a full-length protein defined by UniProt P04626, a fragment thereof, or a variant thereof.

As used herein, "detectable affinity" means the ability to bind to a selected target with an affinity constant of generally at least about $10^{-5}$ M or below. Lower affinities are generally no longer measurable with common methods such as ELISA and therefore of secondary importance.

As used herein, "binding affinity" of a protein of the disclosure (e.g. a mutein of a lipocalin) or a fusion polypeptide thereof to a selected target (in the present case, CD137 and/or HER2/neu), can be measured (and thereby KD values of a mutein-ligand complex be determined) by a multitude of methods known to those skilled in the art. Such methods include, but are not limited to, fluorescence titration, competition ELISA, calorimetric methods, such as isothermal titration calorimetry (ITC), and surface plasmon resonance (BIAcore). Such methods are well established in the art and examples thereof are also detailed below.

It is also noted that the complex formation between the respective binder and its ligand is influenced by many different factors such as the concentrations of the respective binding partners, the presence of competitors, pH and the ionic strength of the buffer system used, and the experimental method used for determination of the dissociation constant $K_D$ (for example fluorescence titration, competition ELISA or surface plasmon resonance, just to name a few) or even the mathematical algorithm which is used for evaluation of the experimental data.

Therefore, it is also clear to the skilled person that the $K_D$ values (dissociation constant of the complex formed between the respective binder and its target/ligand) may vary within a certain experimental range, depending on the method and experimental setup that is used for determining the affinity of a particular lipocalin mutein for a given ligand. This means that there may be a slight deviation in the measured $K_D$ values or a tolerance range depending, for example, on whether the $K_D$ value was determined by surface plasmon resonance (Biacore), by competition ELISA, or by "direct ELISA."

As used herein, a "mutein," a "mutated" entity (whether protein or nucleic acid), or "mutant" refers to the exchange, deletion, or insertion of one or more nucleotides or amino acids, compared to the naturally occurring (wild-type) nucleic acid or protein "reference" scaffold. Said term also includes fragments of a mutein and variants as described herein. Lipocalin muteins of the present invention, fragments or variants thereof preferably retain the function of binding to CD137 as described herein.

The term "fragment" as used herein in connection with the muteins of the disclosure relates to proteins or peptides derived from full-length mature human tear lipocalin that are N-terminally and/or C-terminally shortened, i.e. lacking at least one of the N-terminal and/or C-terminal amino acids. Such fragments may include at least 10, more such as 20 or 30 or more consecutive amino acids of the primary sequence of the mature lipocalin and are usually detectable in an immunoassay of the mature lipocalin. In general, the term "fragment", as used herein with respect to the corresponding protein ligand CD137 of a lipocalin mutein of the disclosure or of the combination according to the disclosure or of a fusion protein described herein, relates to N-terminally and/or C-terminally shortened protein or peptide ligands, which retain the capability of the full length ligand to be recognized and/or bound by a mutein according to the disclosure.

The term "mutagenesis" as used herein means that the experimental conditions are chosen such that the amino acid naturally occurring at a given sequence position of the mature lipocalin can be substituted by at least one amino acid that is not present at this specific position in the respective natural polypeptide sequence. The term "mutagenesis" also includes the (additional) modification of the length of sequence segments by deletion or insertion of one or more amino acids. Thus, it is within the scope of the disclosure that, for example, one amino acid at a chosen sequence position is replaced by a stretch of three random mutations, leading to an insertion of two amino acid residues compared to the length of the respective segment of the wild-type protein. Such an insertion or deletion may be introduced independently from each other in any of the peptide segments that can be subjected to mutagenesis in the disclosure. In one exemplary embodiment of the disclosure, an insertion of several mutations may be introduced into the loop AB of the chosen lipocalin scaffold (cf. International Patent Application WO 2005/019256 which is incorporated by reference its entirety herein).

The term "random mutagenesis" means that no predetermined single amino acid (mutation) is present at a certain sequence position but that at least two amino acids can be incorporated with a certain probability at a predefined sequence position during mutagenesis.

"Identity" is a property of sequences that measures their similarity or relationship. The term "sequence identity" or "identity" as used in the present disclosure means the percentage of pair-wise identical residues—following (homologous) alignment of a sequence of a polypeptide of the disclosure with a sequence in question—with respect to the number of residues in the longer of these two sequences. Sequence identity is measured by dividing the number of identical amino acid residues by the total number of residues and multiplying the product by 100.

The term "homology" is used herein in its usual meaning and includes identical amino acids as well as amino acids which are regarded to be conservative substitutions (for example, exchange of a glutamate residue by an aspartate residue) at equivalent positions in the linear amino acid sequence of a polypeptide of the disclosure (e.g., any lipocalin mutein of the disclosure).

The percentage of sequence homology or sequence identity can, for example, be determined herein using the program BLASTP, version blastp 2.2.5 (Nov. 16, 2002; cf. Altschul, S. F. et al. (1997) *Nucl. Acids Res.* 25, 3389-3402). In this embodiment the percentage of homology is based on the alignment of the entire polypeptide sequences (matrix: BLOSUM 62; gap costs: 11.1; cutoff value set to $10^{-3}$) including the propeptide sequences, preferably using the wild-type protein scaffold as reference in a pairwise comparison. It is calculated as the percentage of numbers of "positives" (homologous amino acids) indicated as result in the BLASTP program output divided by the total number of amino acids selected by the program for the alignment.

Specifically, in order to determine whether an amino acid residue of the amino acid sequence of a lipocalin (mutein) different from a wild-type lipocalin corresponds to a certain position in the amino acid sequence of a wild-type lipocalin, a skilled artisan can use means and methods well-known in the art, e.g., alignments, either manually or by using computer programs such as BLAST2.0, which stands for Basic Local Alignment Search Tool or ClustalW or any other suitable program which is suitable to generate sequence alignments. Accordingly, a wild-type lipocalin can serve as "subject sequence" or "reference sequence", while the amino acid sequence of a lipocalin different from the wild-type lipocalin described herein serves as "query sequence". The terms "reference sequence" and "wild-type sequence" are used interchangeably herein. A preferred wild-type lipocalin is shown in SEQ ID NO: 17 (hTlc) or SEQ ID NO: 18 (hNGAL), respectively. Dependent on whether a lipocalin mutein of the present invention is based on Tlc or NGAL, respectively, the corresponding wild-type lipocalin may be used as reference sequence or wild-type sequence.

"Gaps" are spaces in an alignment that are the result of additions or deletions of amino acids. Thus, two copies of exactly the same sequence have 100% identity, but sequences that are less highly conserved, and have deletions, additions, or replacements, may have a lower degree of sequence identity. Those skilled in the art will recognize that several computer programs are available for determining sequence identity using standard parameters, for example Blast (Altschul, et al. (1997) Nucleic Acids Res. 25, 3389-3402), Blast2 (Altschul, et al. (1990) J. Mol. Biol. 215, 403-410), and Smith-Waterman (Smith, et al. (1981) J. Mol. Biol. 147, 195-197).

The term "variant" as used in the present disclosure relates to derivatives of a protein or peptide that include modifications of the amino acid sequence, for example by substitution, deletion, insertion or chemical modification. Such modifications do in some embodiments not reduce the functionality of the protein or peptide. Such variants include proteins, wherein one or more amino acids have been replaced by their respective D-stereoisomers or by amino acids other than the naturally occurring 20 amino acids, such as, for example, ornithine, hydroxyproline, citrulline, homoserine, hydroxylysine, norvaline. However, such substitutions may also be conservative, i.e. an amino acid residue is replaced with a chemically similar amino acid residue. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. The term "variant", as used herein with respect to the corresponding protein ligand CD137 of a lipocalin mutein of the disclosure or of the combination according to the disclosure or of a fusion protein described herein, relates to CD137 or fragment thereof, respectively, that has one or more such as 1, 2, 3, 4, 5, 6, 7, 8, 9, 10, 12, 14, 16, 18, 20, 22, 24, 26, 28, 30, 40, 50, 60, 70, 80 or more amino acid substitutions, deletions and/or insertions in comparison to a wild-type CD137 protein, respectively, such as a CD137 reference protein as deposited with UniProt as described herein. A CD137 variant, respectively, has preferably an amino acid identity of at least 50%, 60%, 70%, 80%, 85%, 90% or 95% with a wild-type human CD137, such as a CD137 reference protein as deposited with UniProt as described herein.

By a "native sequence" lipocalin is meant a lipocalin that has the same amino acid sequence as the corresponding polypeptide derived from nature. Thus, a native sequence lipocalin can have the amino acid sequence of the respective naturally-occurring lipocalin from any organism, in particular a mammal. Such native sequence polypeptide can be isolated from nature or can be produced by recombinant or synthetic means. The term "native sequence" polypeptide specifically encompasses naturally-occurring truncated or secreted forms of the lipocalin, naturally-occurring variant forms such as alternatively spliced forms and naturally-occurring allelic variants of the lipocalin. A polypeptide "variant" means a biologically active polypeptide having at least about 50%, 60%, 70%, 80% or at least about 85% amino acid sequence identity with the native sequence polypeptide. Such variants include, for instance, polypeptides in which one or more amino acid residues are added or deleted at the N- or C-terminus of the polypeptide. Generally a variant has at least about 70%, including at least about 80%, such as at least about 85% amino acid sequence identity, including at least about 90% amino acid sequence identity or at least about 95% amino acid sequence identity with the native sequence polypeptide. As an illustrative example, the first 4 N-terminal amino acid residues (His-His-Leu-Leu) and the last 2 C-terminal amino acid residues (Ser-Asp) can be deleted in a tear lipocalin (Tlc) mutein of the disclosure without affecting the biological function of the protein, e.g. SEQ ID NOs: 32-38. In addition, as another illustrative example, certain amino acid residues can be deleted in a lipocalin 2 (NGAL) mutein of the disclosure without affecting the biological function of the protein, e.g. (Lys-Asp-Pro, positions 46-48) as to SEQ ID NO: 42.

The term "position" when used in accordance with the disclosure means the position of either an amino acid within an amino acid sequence depicted herein or the position of a nucleotide within a nucleic acid sequence depicted herein. To understand the term "correspond" or "corresponding" as used herein in the context of the amino acid sueqnece positions of one or more lipocalin muteins, a corresponding position is not only determined by the number of the preceding nucleotides/amino acids. Accordingly, the position of a given amino acid in accordance with the disclosure which may be substituted may vary due to deletion or addition of amino acids elsewhere in a (mutant or wild-type) lipocalin. Similarly, the position of a given nucleotide in accordance with the present disclosure which may be substituted may vary due to deletions or additional nucleotides elsewhere in a mutein or wild-type lipocalin 5'-untranslated region (UTR) including the promoter and/or any other regulatory sequences or gene (including exons and introns).

Thus, for a corresponding position in accordance with the disclosure, it is preferably to be understood that the positions of nucleotides/amino acids may differ in the indicated number than similar neighbouring nucleotides/amino acids, but said neighbouring nucleotides/amino acids, which may be exchanged, deleted, or added, are also comprised by the one or more corresponding positions.

In addition, for a corresponding position in a lipocalin mutein based on a reference scaffold in accordance with the disclosure, it is preferably to be understood that the positions of nucleotides/amino acids are structurally corresponding to the positions elsewhere in a (mutant or wild-type) lipocalin, even if they may differ in the indicated number, as appreciated by the skilled in light of the highly-conserved overall folding pattern among lipocalins.

The word "detect", "detection", "detectable" or "detecting" as used herein is understood both on a quantitative and a qualitative level, as well as a combination thereof. It thus includes quantitative, semi-quantitative and qualitative measurements of a molecule of interest.

A "subject" is a vertebrate, preferably a mammal, more preferably a human. The term "mammal" is used herein to refer to any animal classified as a mammal, including, without limitation, humans, domestic and farm animals, and zoo, sports, or pet animals, such as sheep, dogs, horses, cats, cows, rats, pigs, apes such as cynomolgus monkeys and etc., to name only a few illustrative examples. Preferably, the mammal herein is human.

An "effective amount" is an amount sufficient to effect beneficial or desired results. An effective amount can be administered in one or more administrations.

A "sample" is defined as a biological sample taken from any subject. Biological samples include, but are not limited to, blood, serum, urine, feces, semen, or tissue.

A "subunit" of a fusion polypeptide disclosed herein is defined as a stretch of amino acids of the polypeptide, which stretch defines a unique functional unit of said polypeptide such as provides binding motif towards a target.

III. DESCRIPTIONS OF FIGURES

FIG. 1: provides an overview over the design of the representative fusion polypeptides described in this application, which are bispecific with regard to the targets, HER2 and CD137. Representative fusion polypeptides were made based on an antibody specific for HER2 (SEQ ID NOs: 3 and 4) and a lipocalin mutein specific for CD137 (SEQ ID NO: 2). Direct fusion of the antibody with the lipocalin mutein resulted in a fusion polypeptide of SEQ ID NOs: 5 and 6. Lipocalin muteins were fused to either one of the four termini of the antibody, using an engineered IgG4 backbone with the mutations S228P, F234A and L235A (SEQ ID NOs: 9 and 10, SEQ ID NOs: 11 and 12, SEQ ID NOs: 13 and 14, SEQ ID NOs: 15 and 16). In addition, within the fusion polypeptide SEQ ID NOs: 7 and 8), a N297A mutation was made to remove the glycosylation motif.

Figure 2:
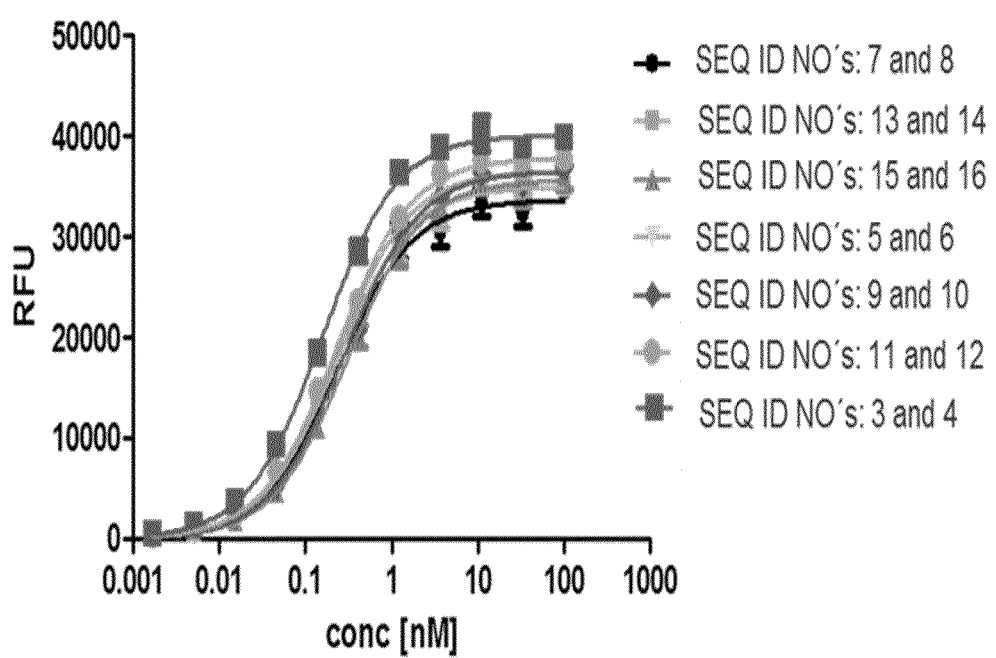

FIG. 2: depicts the results of an ELISA experiment in which the affinity of representative fusion polypeptides and the benchmark antibody against HER2 was determined. Recombinant HER2 was coated on a microtiter plate, and the tested agents were titrated starting from a concentration of 100 nM. Bound agents under study were detected via an anti-human IgG Fc antibody as described in Example 2. The data was fit with a 1:1 binding model with EC50 value and the maximum signal as free parameters, and a slope that was fixed to unity. The resulting EC50 values are provided in Table 2.

Figure 3:
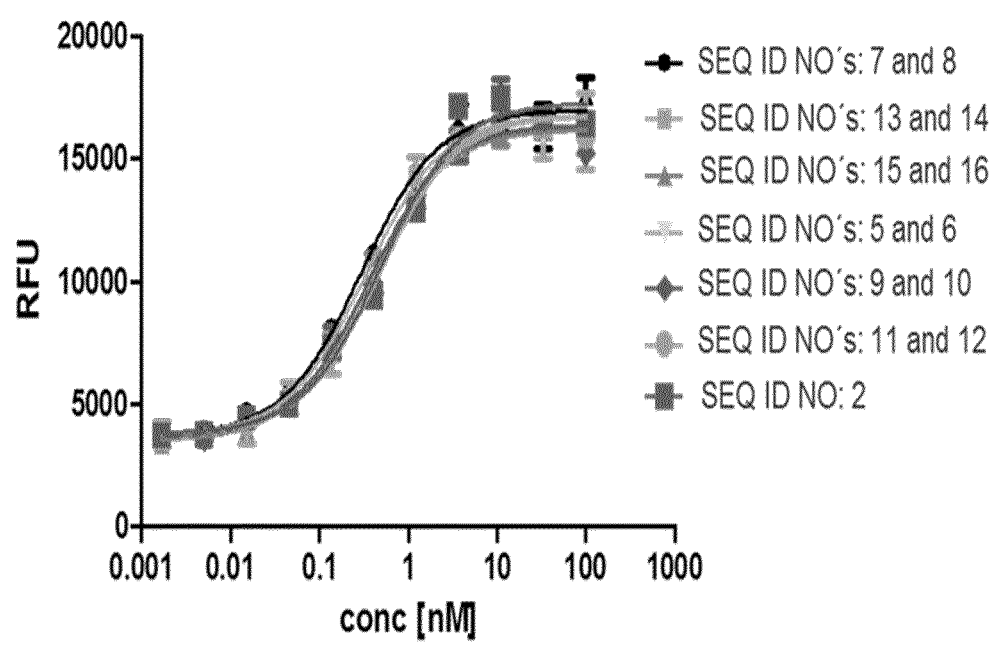

FIG. 3: shows the results of an ELISA experiment in which the affinity of representative fusion polypeptides and the positive control lipocalin mutein against CD137 was determined. An Fc-fusion of human CD137 was coated on a microtiter plate, and the tested agents were titrated starting from a concentration of 100 nM. Bound agents under study were detected via an anti-human-IgG-Fc antibody as described in Example 3. The data was fit with a 1:1 binding model with EC50 value and the maximum signal as free parameters, and a slope that was fixed to unity. The resulting EC50 values are provided in Table 3.

Figure 4:
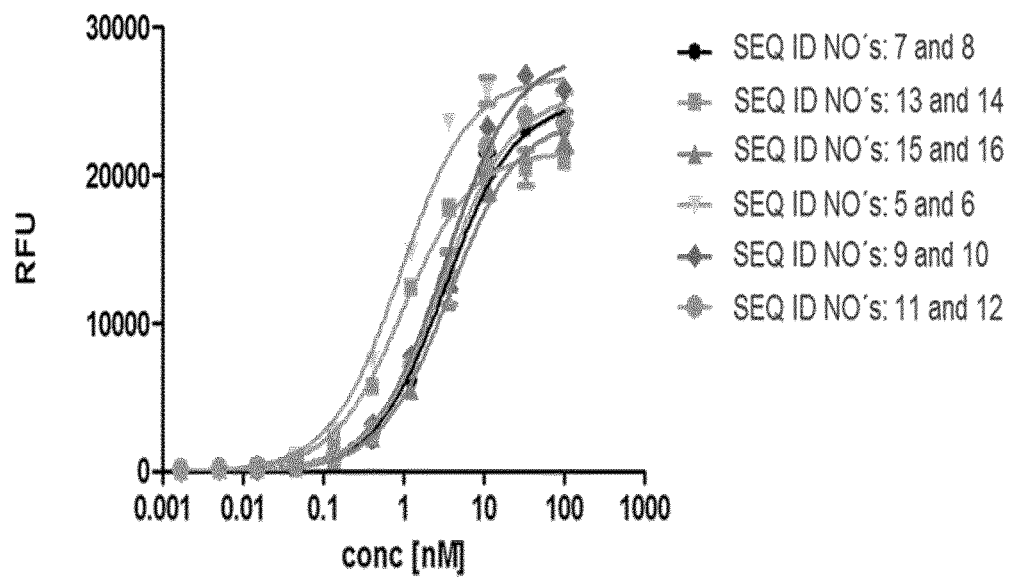

FIG. 4: illustrates the results of an ELISA experiment in which the ability of representative fusion polypeptides to simultaneously bind both targets, HER2 and CD137, was determined. Recombinant HER2 was coated on a microtiter plate, followed by a titration of the fusion polypeptides starting from a concentration of 100 nM. Subsequently, a constant concentration of biotinylated human CD137-Fc was added, which was detected via extravidin as described in Example 4.

Figure 5:
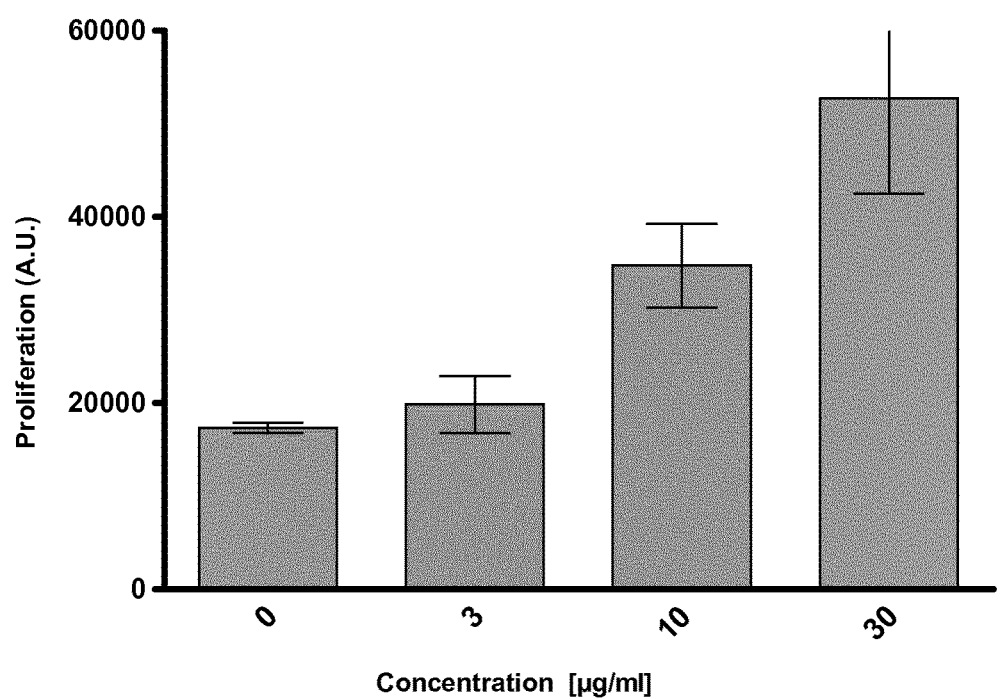

FIG. 5: shows the result of a T-cell activation assay in which the ability of the fusion polypeptide of SEQ ID NOs: 15 and 16 to co-stimulate T-cell responses was assessed. The fusion polypeptide of SEQ ID NOs: 15 and 16 at different concentrations was coated onto a plastic dish together with an anti-human CD3 antibody, and purified T-cells were subsequently incubated on the coated surface. Supernatant interleukin 2 (IL-2) levels were measured as described in Example 5.

Figure 6:
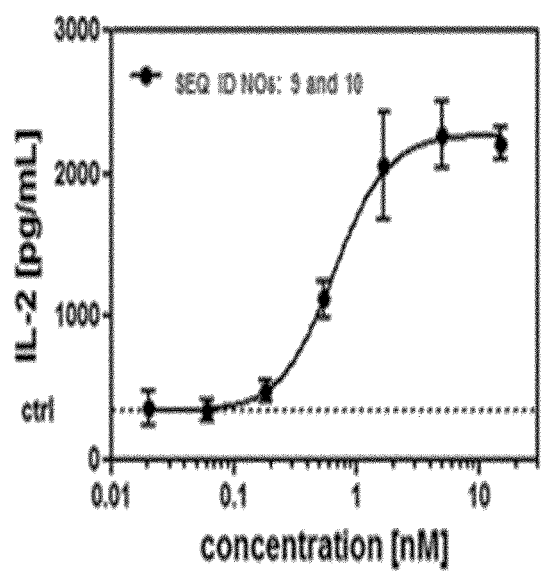
Figure 6:
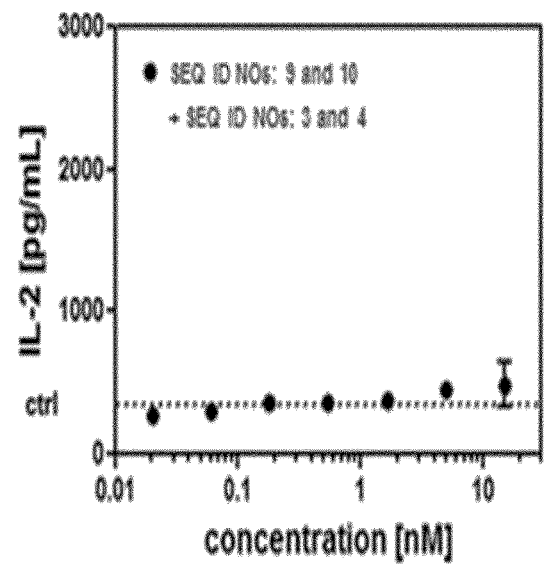
Figure 6:
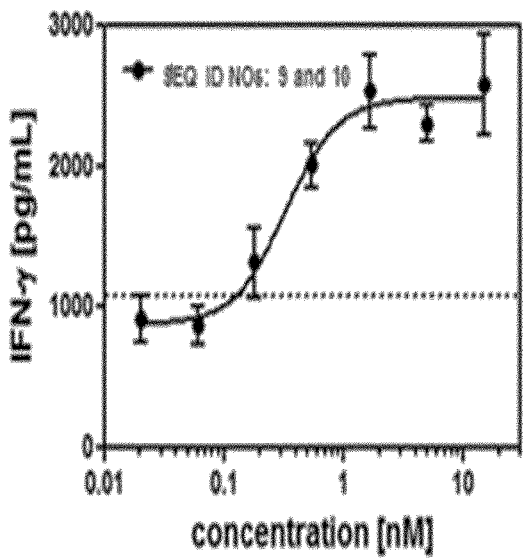
Figure 6:
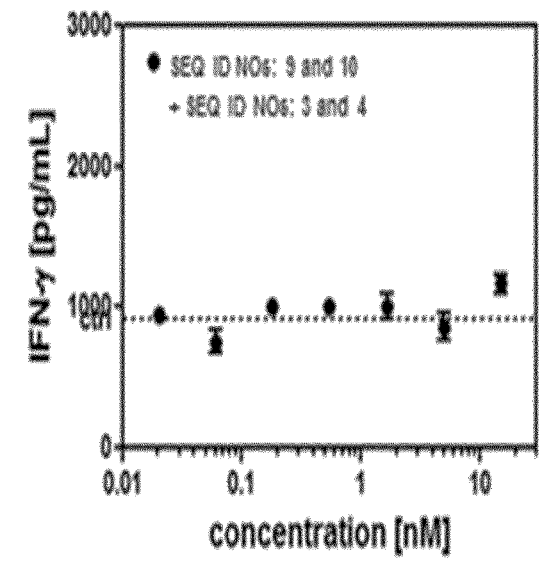

FIG. 6: provides a representative experiment in which the ability of the fusion polypeptide of SEQ ID NOs: 9 and 10 to co-stimulate T-cell activation in a HER2-target-dependent manner was investigated. As a control, we employed the monospecific, HER2-binding antibody of SEQ ID NOs: 3 and 4. In the experiment, an anti-human CD3 antibody was coated on a plastic culture dish, and subsequently HER2-positive SKBR3 cells were cultured on the dish overnight. The next day, purified T-cells were incubated on the coated surface in the presence of various concentrations of the bispecific fusion polypeptide SEQ ID NOs: 9 and 10 (filled circles) or the control antibody of SEQ ID NOs: 3 and 4. The values determined for SEQ ID NOs: 3 and 4 at different concentrations are provided as the average (dotted line). Supernatant interleukin 2 (IL-2) (A) and IFN-γ (B) were determined by an Electrochemoluminescence-based assay. The experiment was also performed in the presence of an excess of SEQ ID NOs: 3 and 4, and supernatant levels of IL-2 (C) and IFN-γ (D) were measured. The data was fitted with a 1:1 binding model.

Figure 7:
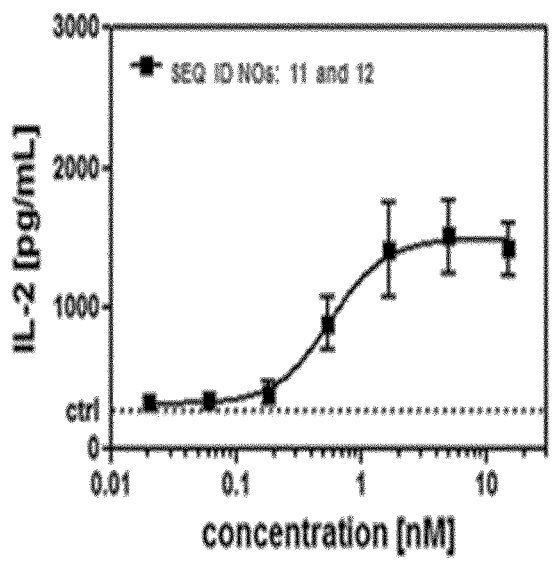
Figure 7:
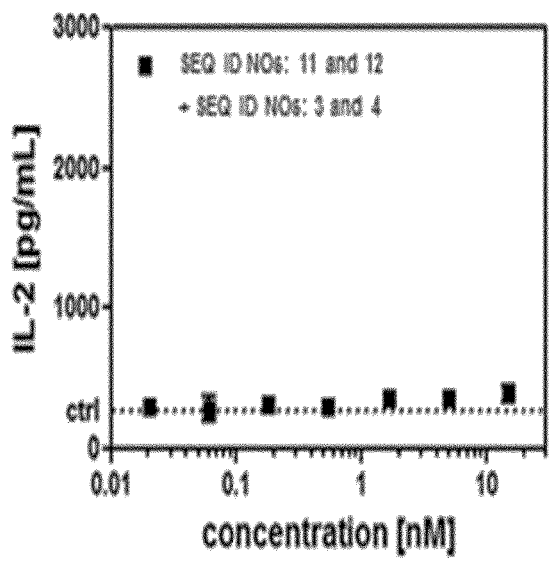
Figure 7:
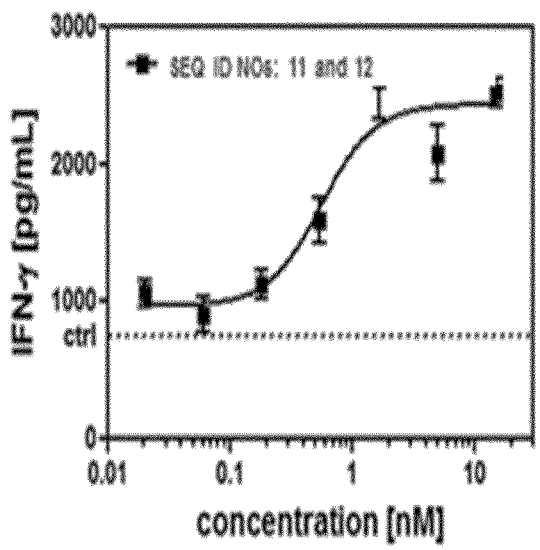
Figure 7:
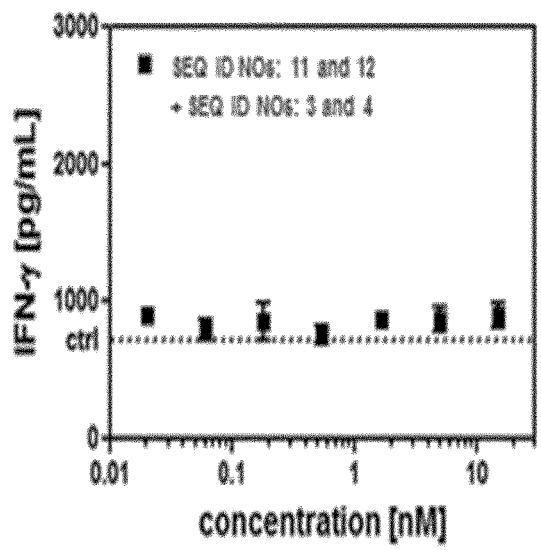

FIG. 7: provides a representative experiment in which the ability of the fusion polypeptide of SEQ ID NOs: 11 and 12 to co-stimulate T-cell activation in a HER2-target-dependent manner was investigated. For details; see legend of FIG. 6.

Figure 8:
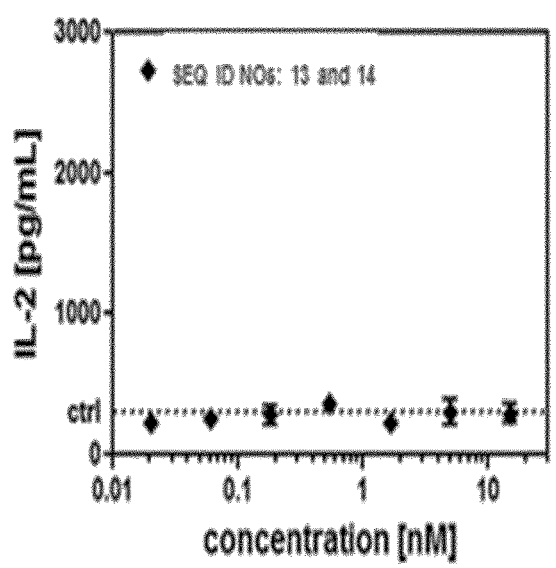
Figure 8:
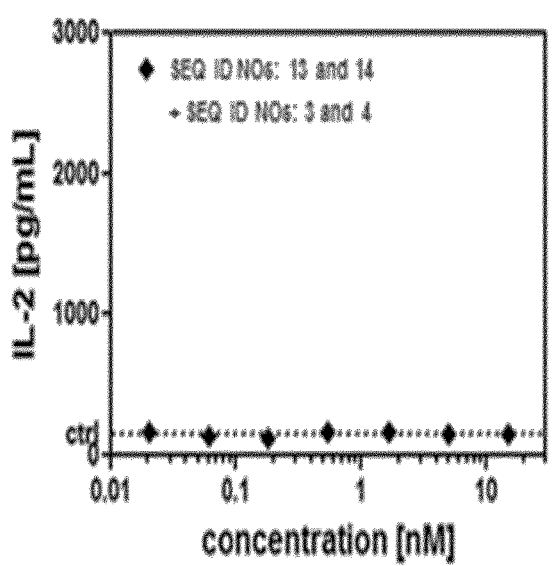
Figure 8:
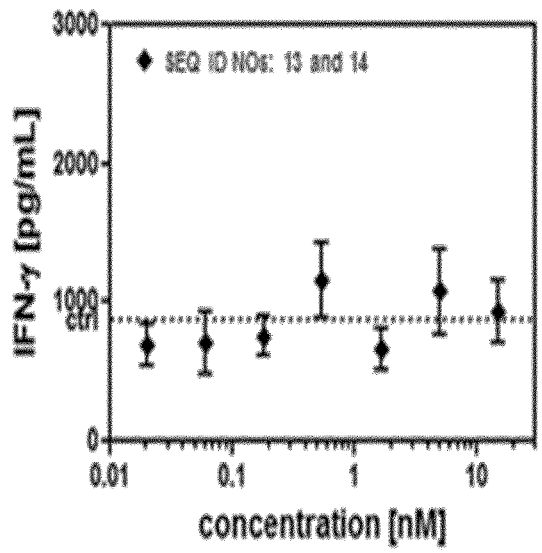
Figure 8:
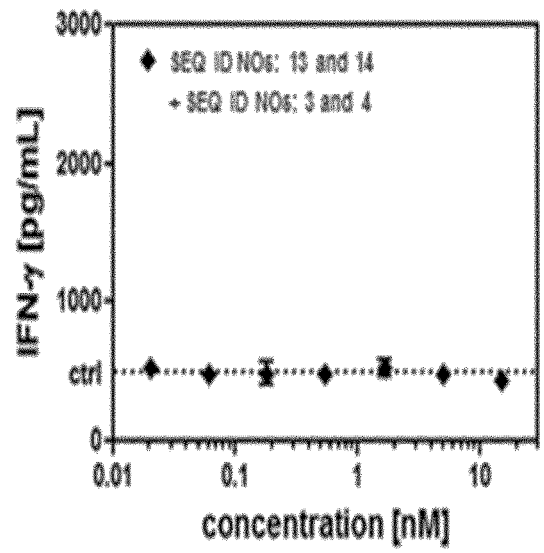

FIG. 8: provides a representative experiment in which the ability of the fusion polypeptide of SEQ ID NOs: 13 and 14 to co-stimulate T-cell activation in a HER2-target-dependent manner was investigated. For details; see legend of FIG. 6.

Figure 9:
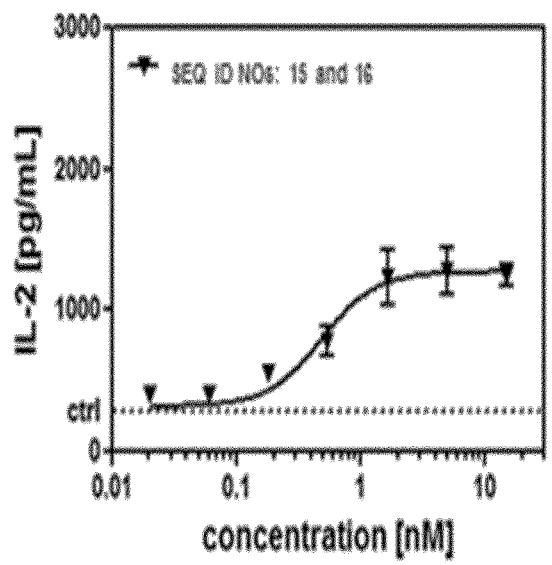
Figure 9:
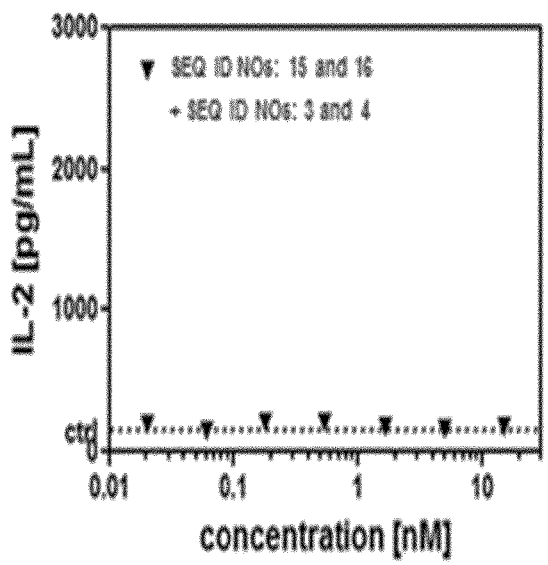
Figure 9:
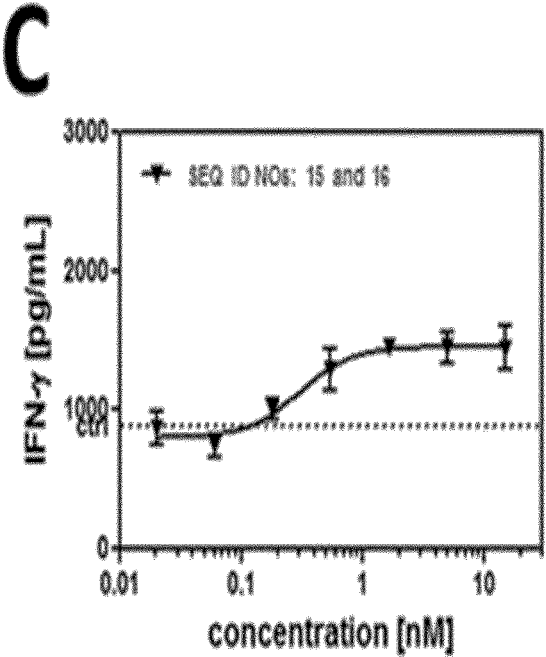
Figure 9:
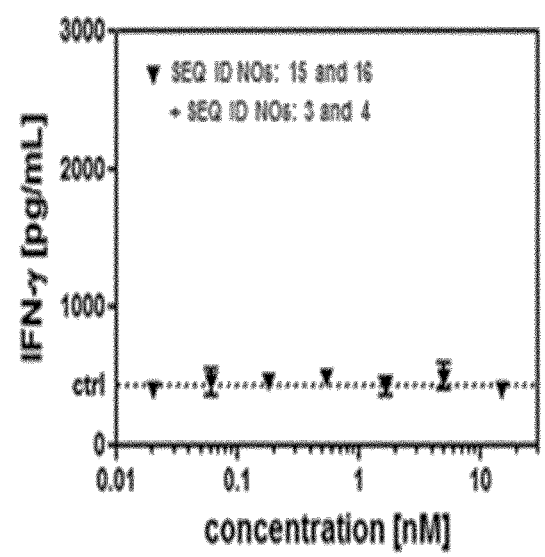

FIG. 9: provides a representative experiment in which the ability of the fusion polypeptide of SEQ ID NOs: 15 and 16 to co-stimulate T-cell activation in a HER2-target-dependent manner was investigated. For details; see legend of FIG. 6.

Figure 10:
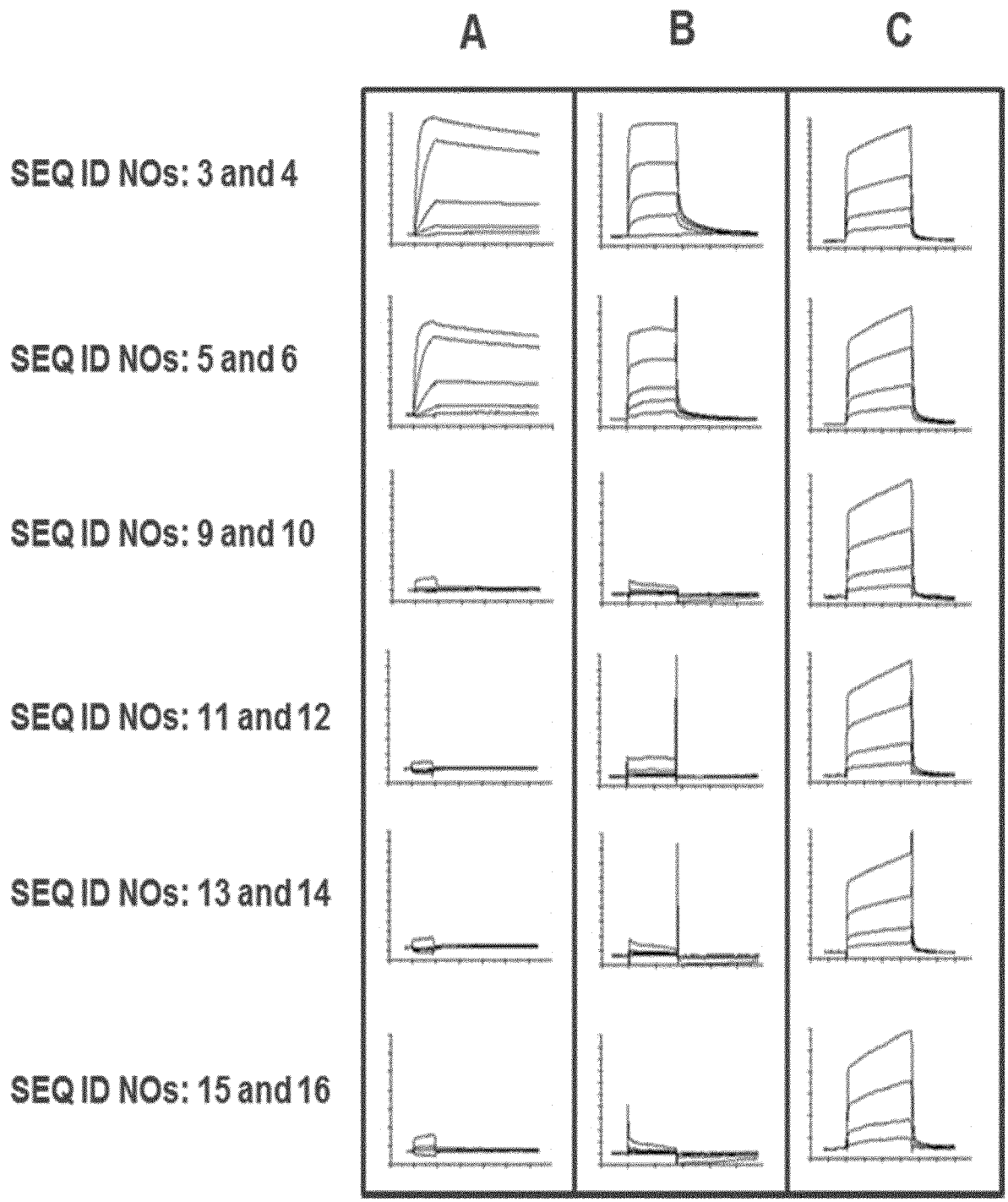

FIG. 10: provides a representative experiment on the affinity of polypeptides to FcgRI, FcgRIII and FcRn as described in Examples 7 and 8.

Figure 11:
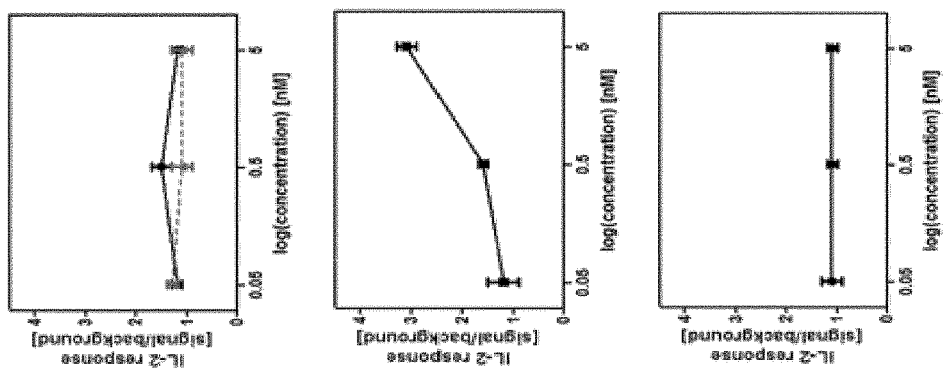
Figure 11:
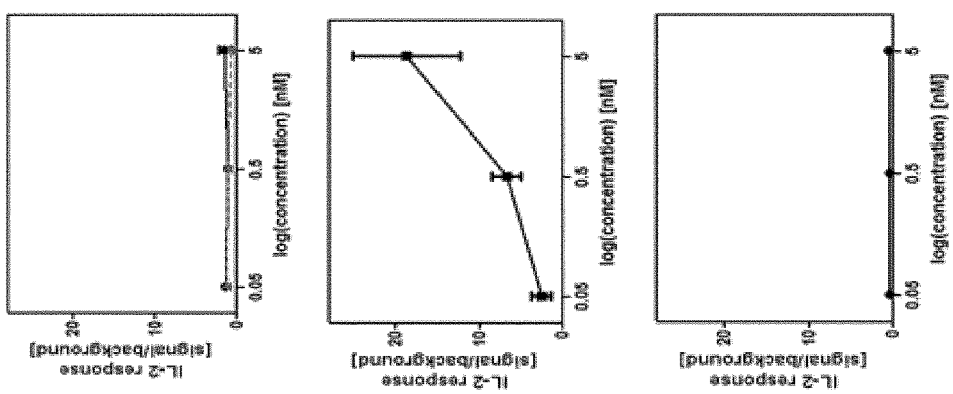
Figure 11:
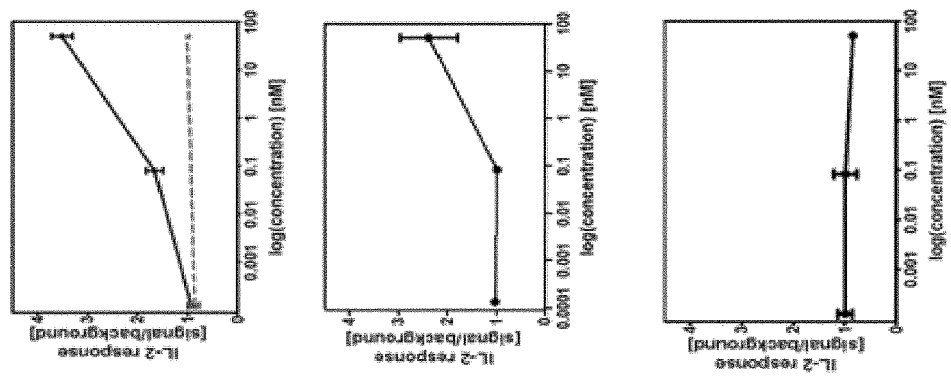

FIG. 11: provides a representative experiment in which the ability of the fusion polypeptides indicated in the Figure to co-stimulate T-cell activation with different cell lines was investigated. Cell lines utilized were the highly HER2-positive cells (SKBR3, BT474) and cell lines expressing HER2 at a level similar to that of healthy cells (HepG2, MCF7). In the experiment, an anti-human CD3 antibody was coated on a plastic culture dish, and subsequently the cell line under study was cultured on the dish overnight. The next day, purified T-cells were incubated on the coated surface for three days in the presence of various concentrations of the bispecific fusion polypeptides as follows: (A) SEQ ID NOs: 9 and 10 (solid lines) or the control antibody of SEQ ID NOs: 3 and 4 (broken line). (B) Anti-CD137 antibody SEQ ID NOs: 32 and 33. (C) Anti-CD137 antibody SEQ ID NOs: 34 and 35. Supernatant interleukin 2 levels were determined by an Electrochemoluminescence-based assay. The plotted relative IL-2 response corresponds to the ratio of the responses obtained in the presence and in the absence ("background") of test articles.

Figure 12:
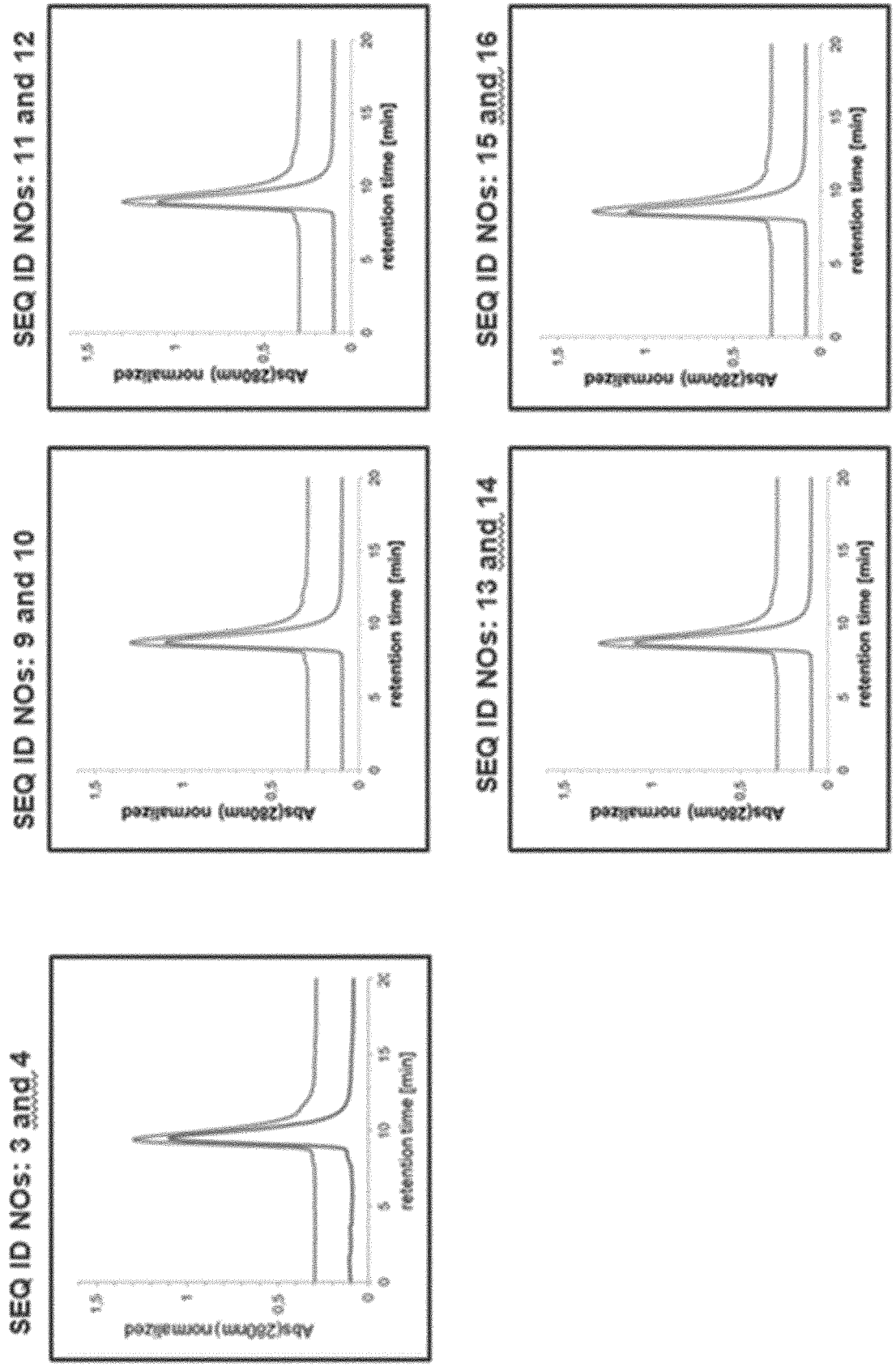

FIG. 12: provides representative size exclusion chromatography (SEC) traces of bispecific fusion polypeptides and the control antibody of SEQ ID NOs: 3 and 4 before (bottom curves) and after (top curves) incubation for 4 weeks at 40° C. in PBS, pH 7.4. Sample concentration was 20 mg/mL in each case, fusion polypeptide identity was as indicated in the figure. SEC curves are plotted with an offset on the y-axis for better visualization.

Figure 13:
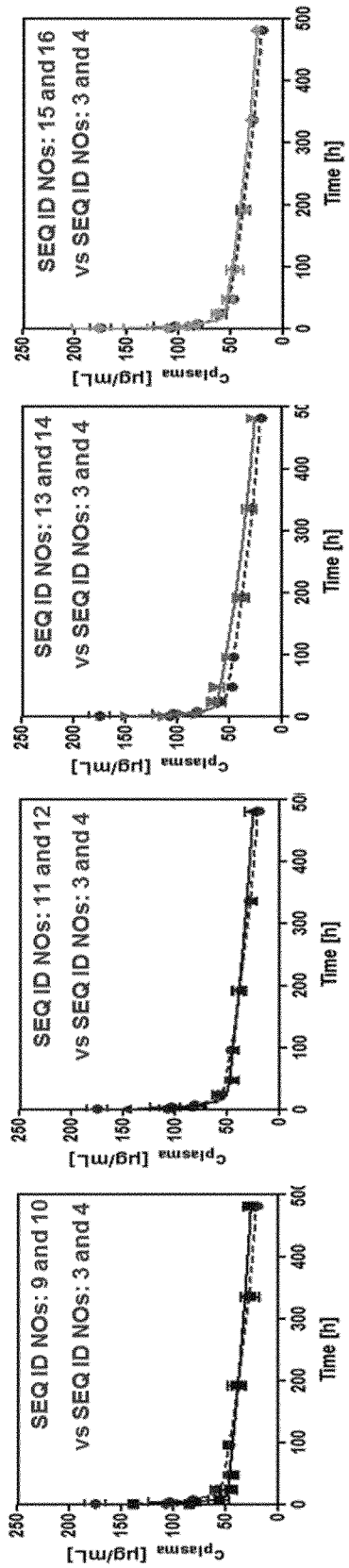

FIG. 13: provides the result of a pharmacokinetic analysis of the bispecific fusion polypeptides and the control antibody of SEQ ID NOs: 3 and 4 in mice. Male CD-1 mice (3 mice per timepoint) were injected intravenously with fusion polypeptides at a dose of 10 mg/kg. Drug levels were detected using a Sandwich ELISA detecting the full bispecific construct via the targets HER2 and CD137. Trastuzumab plasma levels were determined using a Sandwich ELISA with targets HER2 and human Fc. The data were fitted using a two-compartmental model.

Figure 14:
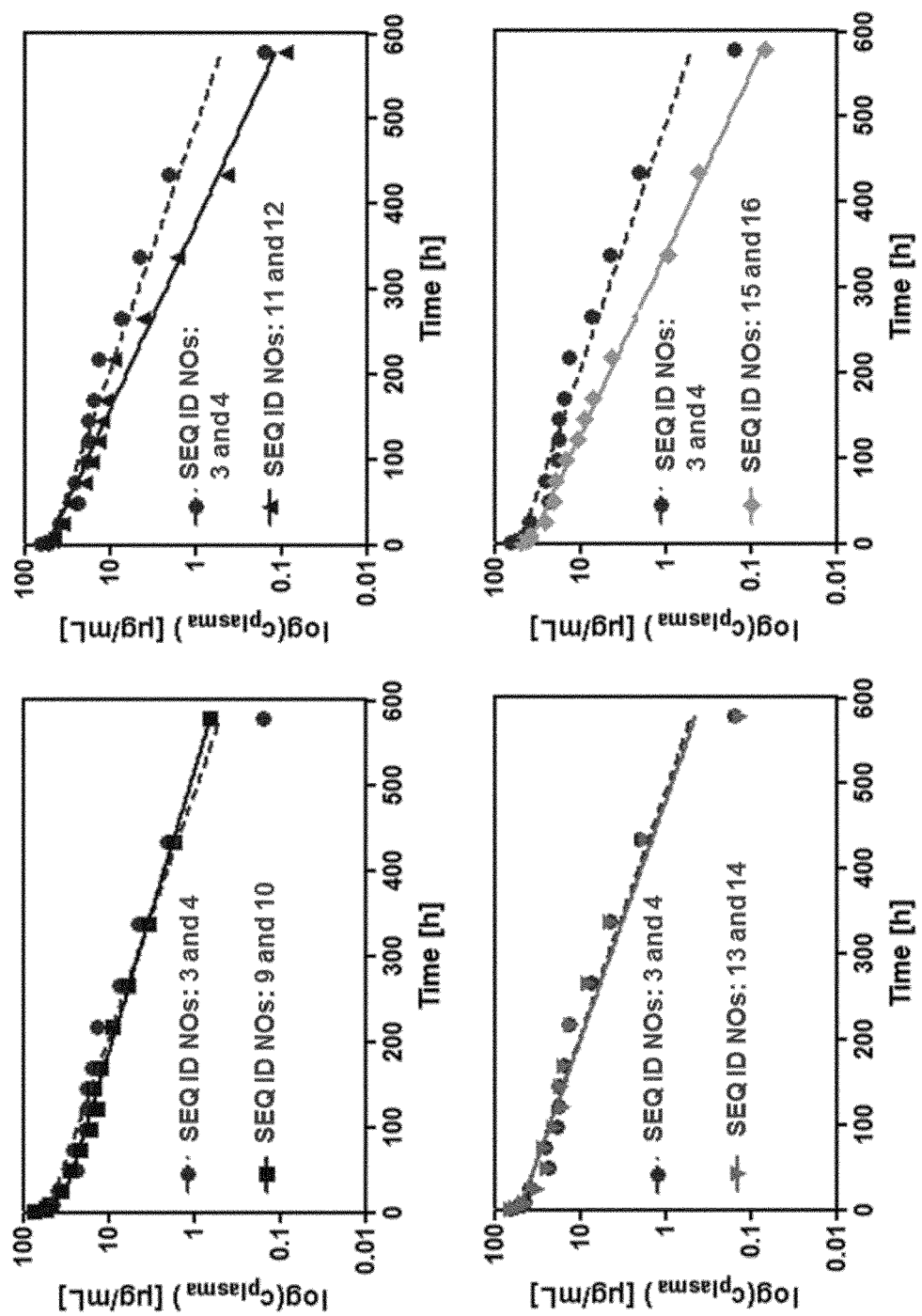

FIG. 14: provides the result of a pharmacokinetic analysis of the bispecific fusion polypeptides and the control antibody of SEQ ID NOs: 3 and 4 in mice. Male, trastuzumab-naïve cynomolgus monkeys received test articles as an intravenous infusion of 60 minutes duration at a dose of 3 mg/kg. Drug levels were detected using a Sandwich ELISA detecting the full bispecific construct via the targets HER2 and CD137. Trastuzumab plasma levels were determined using a Sandwich ELISA with targets HER2 and human Fc. The data were fitted using a two-compartmental model.

Figure 15:
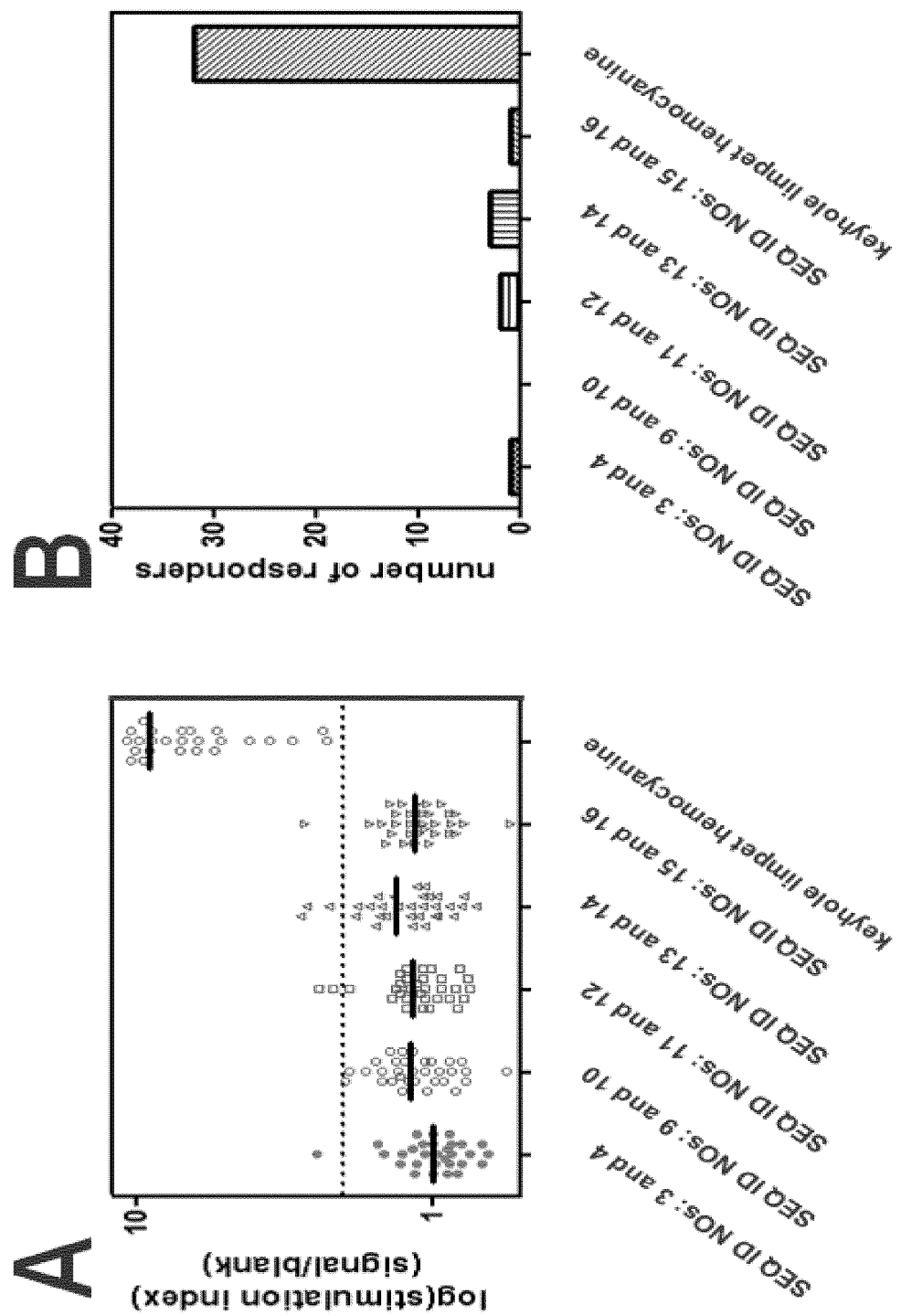

FIG. 15: provides the result of an in vitro T cell immunogenicity assessment of the bispecific fusion polypeptides, the control antibody of SEQ ID NOs: 3 and 4 and the positive control keyhole limpet hemocyanine (KLH). The assay was performed using a PBMC-based format as described in Example 13, with 32 donors and human leukocyte antigen (HLA) allotypes reflective of the distribution in a global population: (A) Stimulation index (proliferation in the presence vs. absence of test article). The average responses are indicated as bars. The threshold that defines a responding donor (stimulation index>2) is indicated as a dotted line. (B) Number of responders FIG. 16: Relative median tumor volume after treatment with CD137/HER2 bispecifics or controls in humanized mouse tumor model. NSG mice were engrafted with s.c. SK-OV-3 tumors which were allowed to grow to an average of 120 mm3. Mice were randomized into treatment groups and received 7×106 fresh human PBMC i.v. and the molecules and doses indicated 1 hour after PBMC injection on day 0, and again on day 7 and day 14. Each group contained 10 mice with the exception of the group studying SEQ ID NOs: 32 and 33 which consisted of 7 mice. Tumor growth was recorded every 3-4 days.

Figure 17:
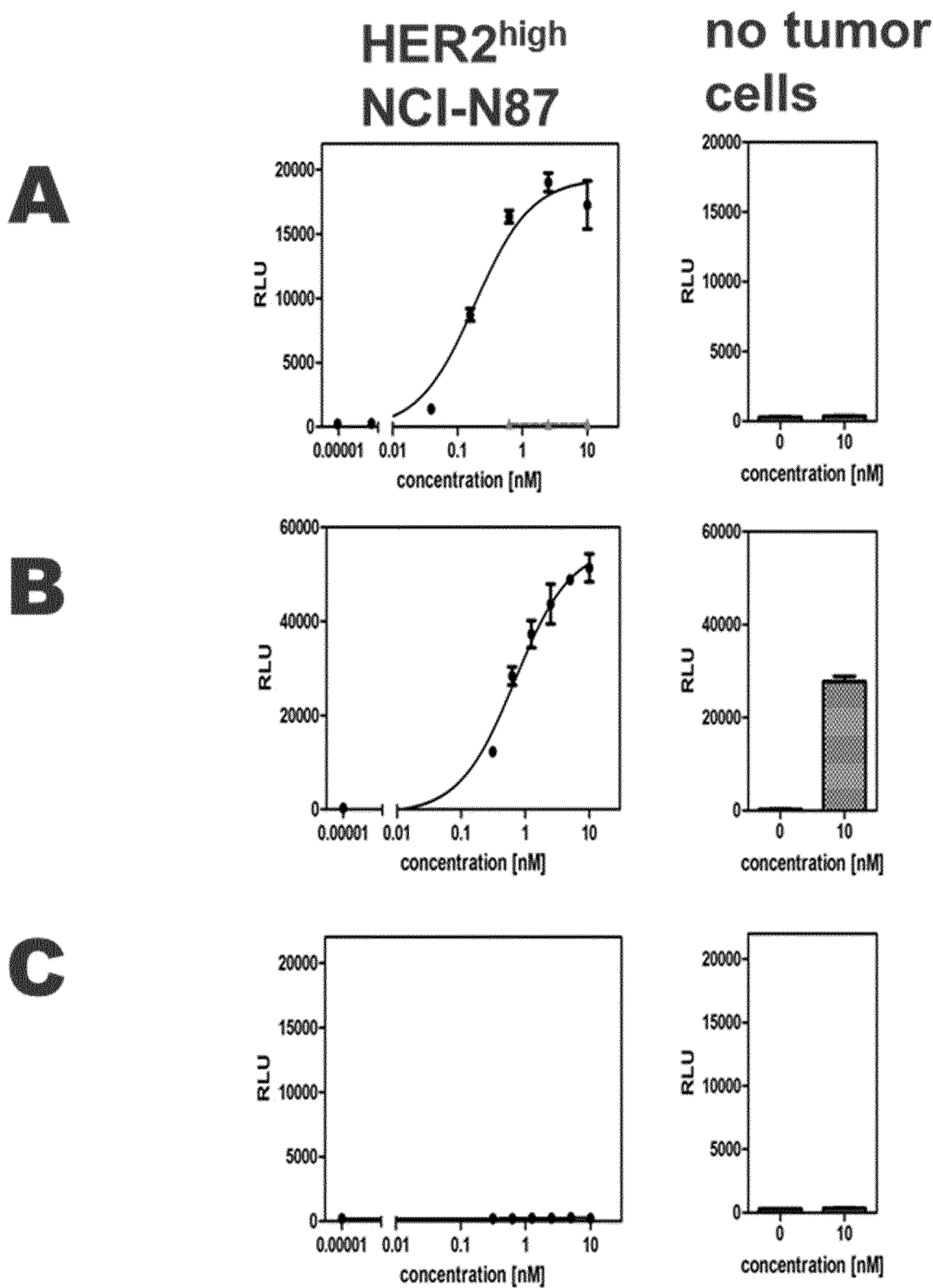

FIG. 17: provides a representative experiment in which the ability of the fusion polypeptides indicated in the Figure to activate the CD137 pathway in dependence of the HER2$^{h19h}$ NCI-N87 target cells was investigated. In the experiment, NCI-N87 tumor target cells were cultured on the dish overnight. The following day, NF-κB-luc2P/4-1BB Jurkat reporter cells were added to the coated target cells in the presence of various concentrations of the bispecific fusion polypeptides as follows: (A) SEQ ID NOs: 9 and 10 (solid lines) or the control antibody of SEQ ID NOs: 3 and 4 (broken line). (B) Anti-CD137 antibody SEQ ID NOs: 32 and 33. (C) Anti-CD137 antibody SEQ ID NOs: 34 and 35. The luminescence signal (RLU) represents a relative measurement of CD137 pathway activation. Four parameter logistic curve analysis was performed with GraphPad Prism software.

Figure 18:
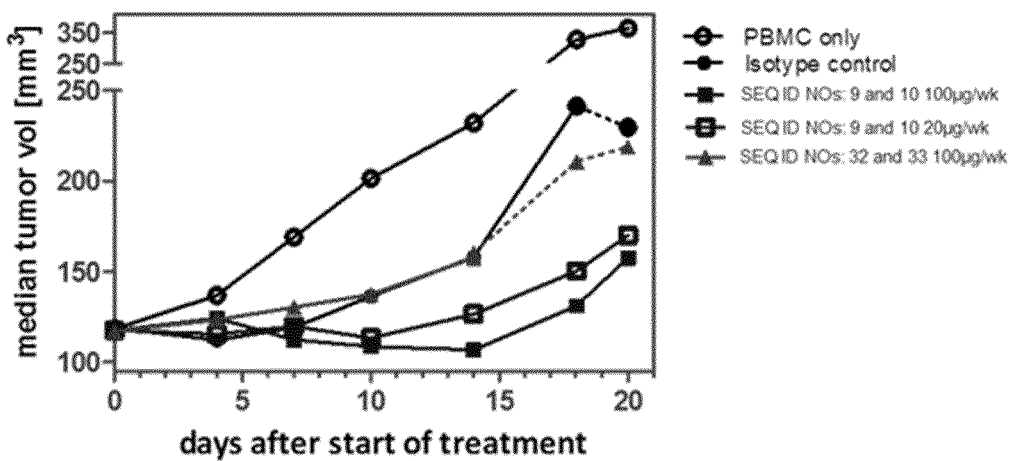
Figure 18:
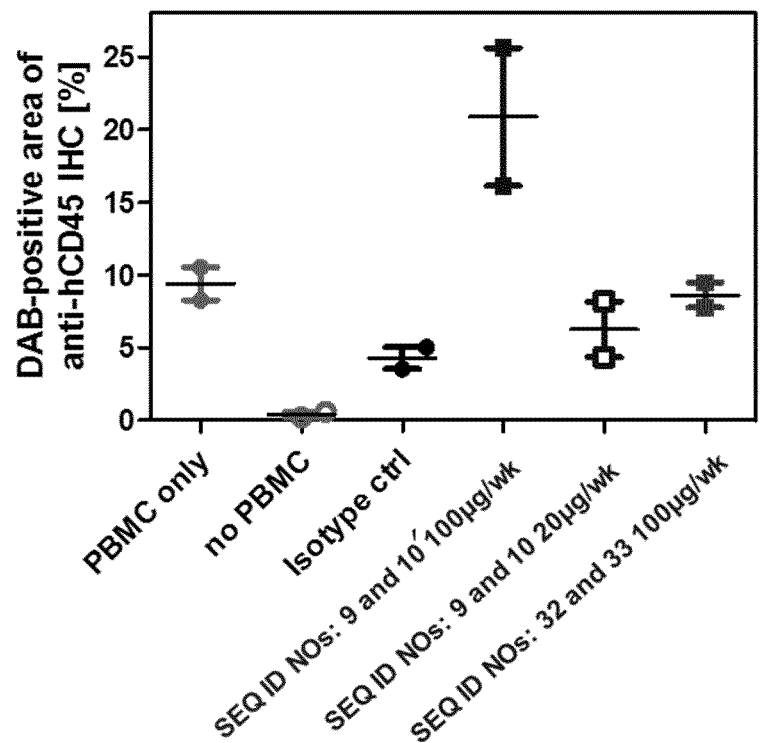

FIG. 18: (A) shows median tumor volume after treatment with CD137/HER2 bispecifics or controls in humanized mouse tumor model. NOG mice were engrafted with s.c. SK-OV-3 tumors which were allowed to grow to an average of 120 mm$^3$. Mice were randomized into treatment groups and received 7×10$^6$ fresh human PBMC i.v. and the molecules and doses indicated 1 hour after PBMC injection on day 0, and again on day 7 and day 14. Each group contained 10 mice. Tumor growth was recorded twice weekly for 20 days. (B) Shows the results of immunohistochemistry for the human lymphocyte marker CD45 as a marker for infiltration of human T cells on tumors from two mice that were harvested on day 20 post treatment.

Figure 19:
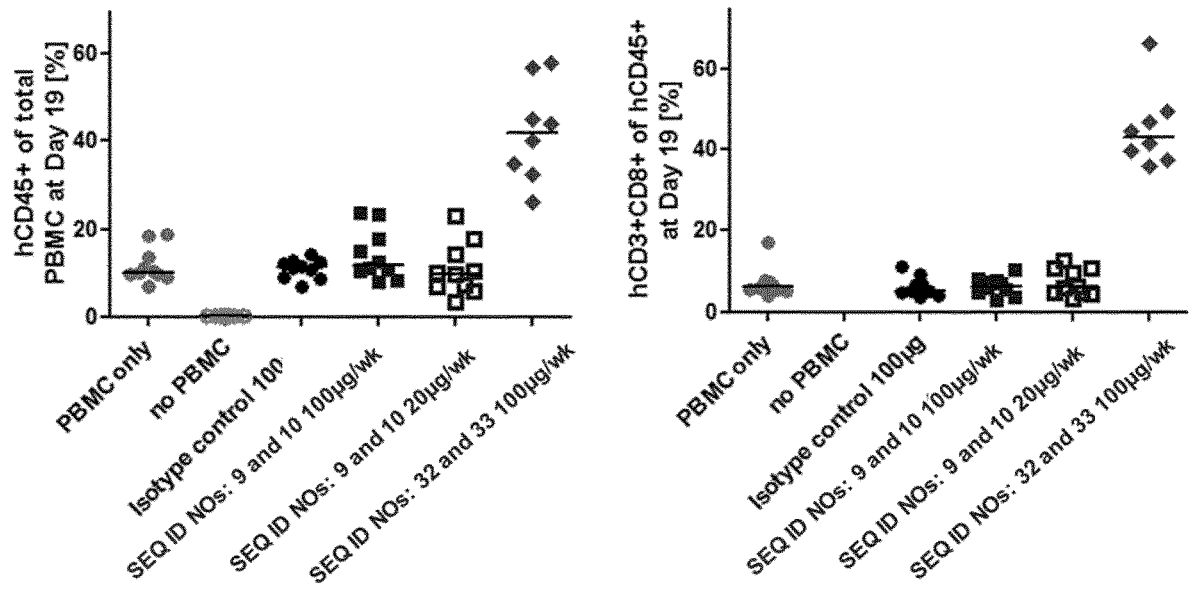
Figure 19:
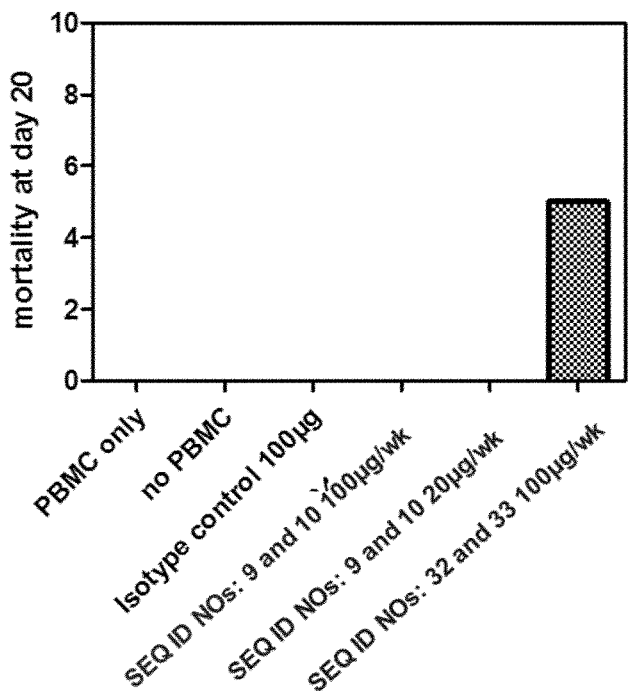

FIG. 19: (A) shows CD45, CD3 and CD8 phenotype of PMBCs of the treatement and control groups of Example 16 taken on day 19 of that study. FIG. 19A on the left shows the percentage of total PMBCs expressing human CD45 while the FIG. 19A on the right shows the percentage of CD45-expressing PMBCs that also express CD3 and CD8. The figure shows increased CD8$^+$ human effector T cell expansion in the anti-CD137 mAb treatment group. (B) shows the mortality of treatment and control groups of Experiment 16. Plotted values of FIG. 19B correspond to number of mice per group of ten that died spontaneously or needed to be sacrificed based on defined general condition criteria.

Figure 20:
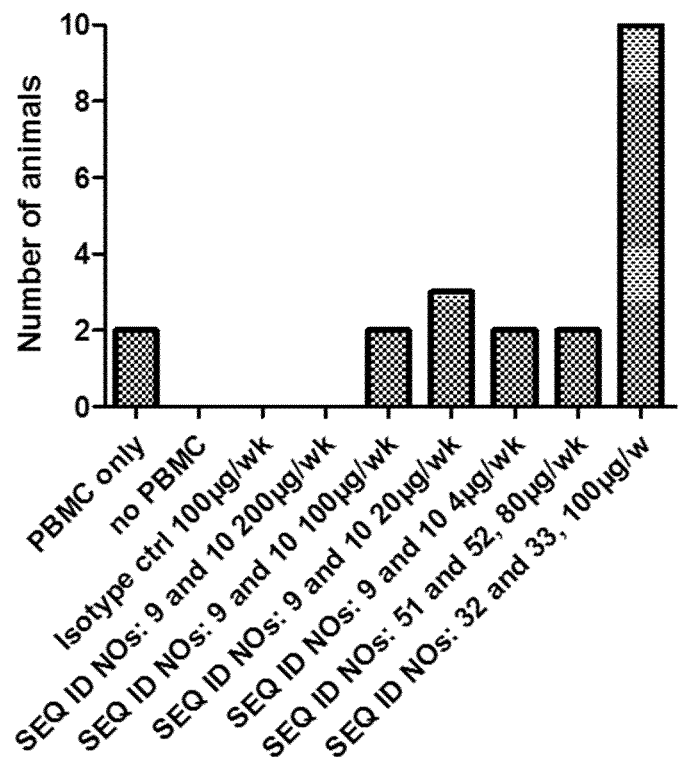

FIG. 20: Mortality of treatment and control groups of Example 18. Plotted values correspond to number of mice per group of ten (SEQ ID Nos: 9 and 10, 4 µg: group of nine) that died spontaneously or needed to be sacrificed based on defined general condition criteria.

Figure 21:
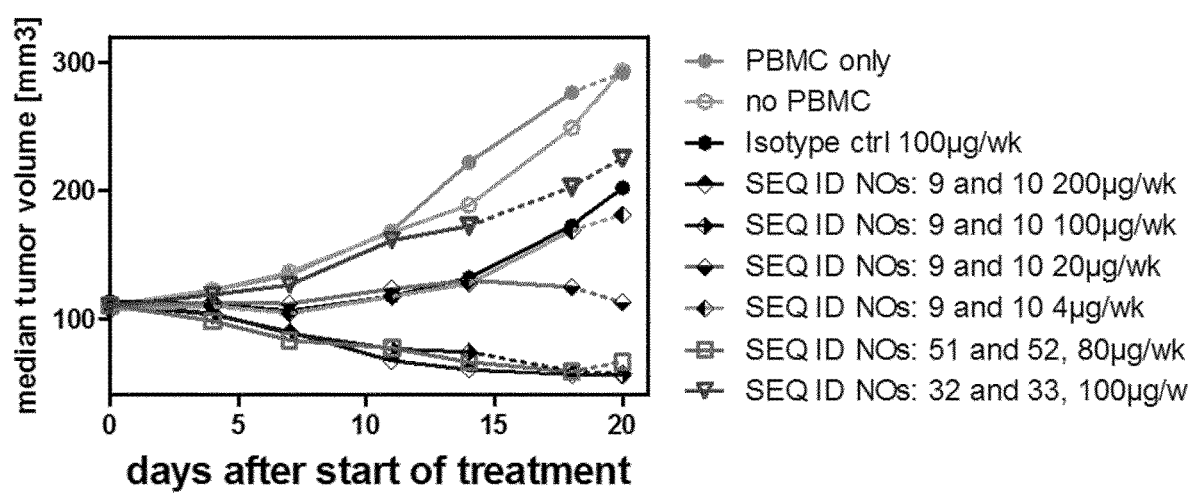

FIG. 21: Relative median tumor volume after treatment with CD137/HER2 bispecifics or controls in humanized mouse tumor model. NSG mice were engrafted with s.c. SK-OV-3 tumors which were allowed to grow to an average of 110 mm$^3$. Mice were randomized into treatment groups and received 7×10$^6$ fresh human PBMC intravenously and intraperitoneal injections of the molecules and doses indicated 1 hour after PBMC injection on day 0, and again on day 7 and day 14. Each group contained 10 mice, except for group 7 (SEQ ID Nos: 9 and 10, 4 µg) which contained only 9 mice. Tumor growth was recorded every 3-4 days.

Figure 22:
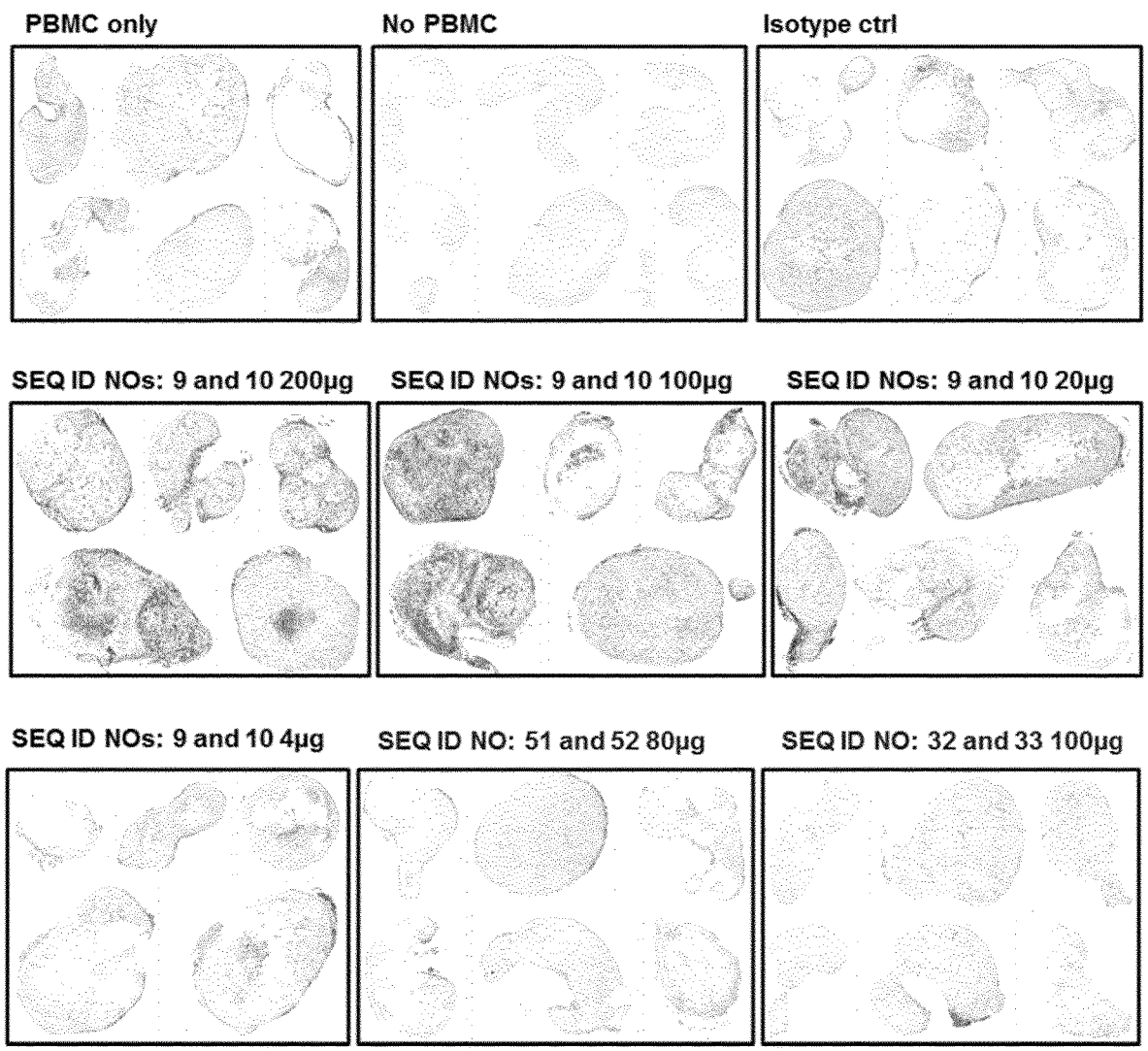

FIG. 22: Immunohistochemistry of human CD45-positive lymphocytes. Tumors were excised from tumor-bearing mice and up to six tumors for each group were formalin-fixed, embedded in paraffin and processed for immunohistochemistry using anti-human CD45 antibodies. CD45-positive cells were identified by 3,3'-diaminobenzidine (DAB) staining. To allow clear visualization of DAB-positivity in a greyscale image, contrast and brightness of the images was digitally adjusted.

Figure 23:
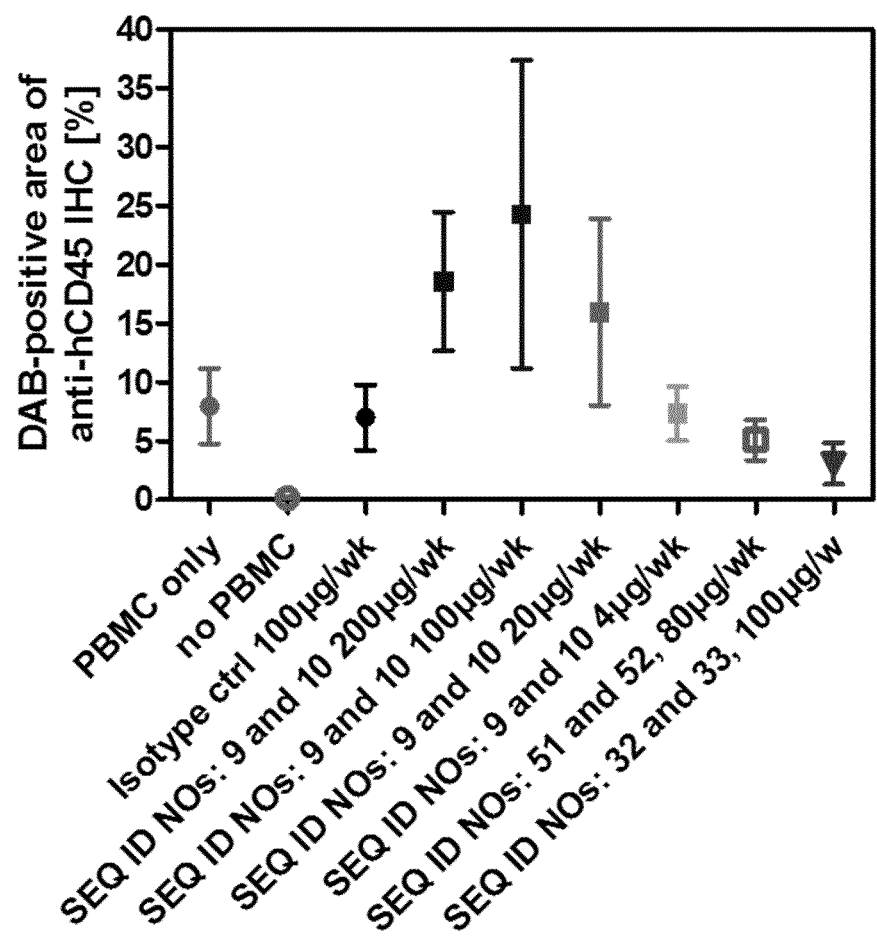

FIG. 23: Digital quantitation of DAB positivity of the images shown in FIG. 22. The Figure illustrates increased frequencies of hCD45-positive human lymphocytes in the groups treated with SEQ ID Nos: 9 and 10 compared to various controls (see Example 17 for details).

Figure 24:
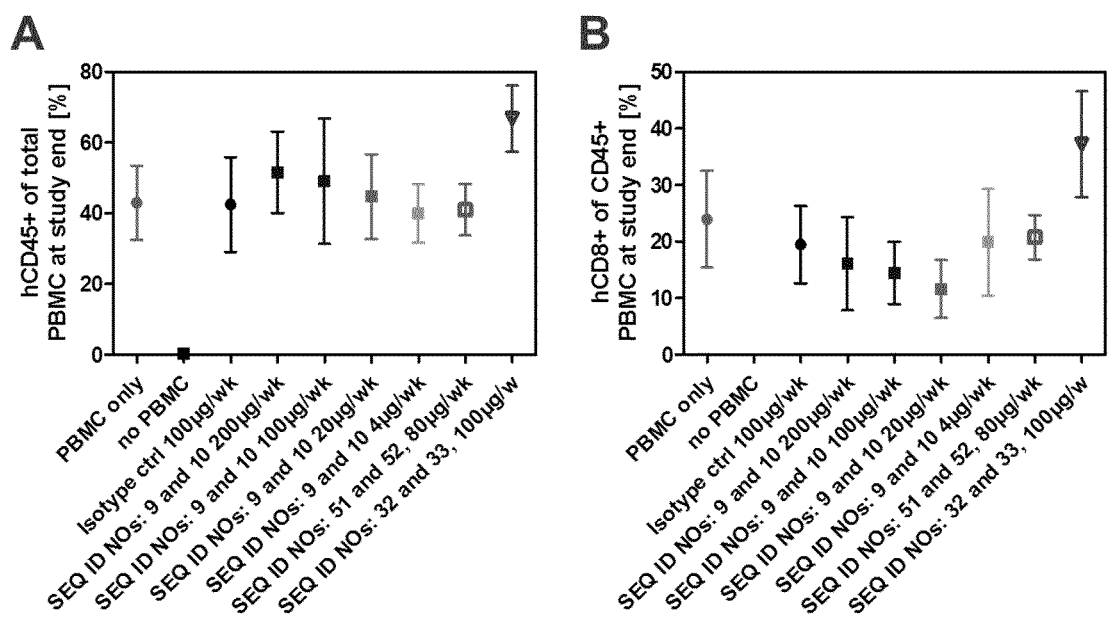

FIG. 24: Phenotype of PMBCs of the treatment and control groups of Example 18 taken on day (19) of that study. (A) Percentage of total PMBCs expressing human CD45. (B) Percentage of CD45-expressing PMBCs that express CD8. The Figure shows increased CD8+ human effector T cell expansion in the anti-CD137 mAb (SEQ ID Nos: 32 and 33) treatment group compared to negative controls and SEQ ID Nos: 9 and 10 treatment groups.

IV. DETAILED DESCRIPTION OF THE DISCLOSURE

In some embodiments, the fusion polypeptide contains at least two subunits in any order: a first subunit that comprises a full-length immunoglobulin or an antigen-binding domain thereof specific for HER2/neu, and a second subunit that comprises a lipocalin mutein specific for CD137.

In some embodiments, the fusion polypeptide also may contain a third subunit. For instance, the polypeptide may contain a subunit specific for CD137. In some embodiments, said third subunit comprises a lipocalin mutein specific for CD137.

In some embodiments, one subunit can be linked to another subunit as essentially described in FIG. 1. For example, one lipocalin mutein can be linked, via a peptide bond, to the C-terminus of the immunoglobulin heavy chain domain (VH), the N-terminus of the VH, the C-terminus of the immunoglobulin light chain (VL), and/or the N-terminus of the VL (cf. FIG. 1). In some particular embodiments, a lipocalin mutein subunit can be fused at its N-terminus and/or its C-terminus to an immunoglobulin subunit. For example, the lipocalin mutein may be linked via a peptide bond between the C-terminus of a heavy chain constant region (CH) or the C-terminus of a light chain constant region (CL) of the immunoglobulin. In some still further embodiments, the peptide bond may be an unstructured (G4S)3 linker, for example, as shown in SEQ ID NO: 19.

In this regard, one subunit may be fused at its N-terminus and/or its C-terminus to another subunit. For example, when one subunit comprises a full-length immunoglobulin, another subunit may be linked via a peptide bond between the N-terminus of the second subunit and the C-terminus of a heavy chain constant region (CH) of said immunoglobulin. In some further embodiments, the third subunit may be linked via a peptide bond between the N-terminus of the third binding domain and the C-terminus of a light chain constant region (CL) of said immunoglobulin. In some still further embodiments, the peptide bond may be a unstructured (G4S)3 linker, for example, as shown in SEQ ID NO: 19.

In some embodiments with respect to a fusion polypeptide of the disclosure, one of whose subunits comprises a full-length immunoglobulin, while the polypeptide is simultaneously engaging HER2/neu and CD137, the Fc function of the Fc region of the full-length immunoglobulin to Fc receptor-positive cell may be preserved at the same time.

In some embodiments, the CD137-specific subunit included in a fusion polypeptide of the disclosure may be a lipocalin mutein that is specific for CD137, such as the lipocalin mutein of SEQ ID NO: 2. In some embodiments, the CD137-specific subunit included in a fusion polypeptide of the disclosure may be a full-length immunoglobulin or an antigen-binding domain thereof that is specific for CD137, such as a monoclonal antibody (e.g. the antibody of SEQ ID NOs: 3 and 4).

In some embodiments, the HER2/neu-specific subunit included in a fusion polypeptide of the disclosure may be a lipocalin mutein that is specific for HER2/neu. In some embodiments, the HER2/neu-specific subunit included in a fusion polypeptide of the disclosure may be a full-length immunoglobulin or an antigen-binding domain thereof that is specific for HER2/neu.

In some embodiments, in a fusion polypeptide of the disclosure, a CD137-specific subunit is fused to a HER2/neu-specific subunit.

In some more specific embodiments, the HER2/neu-specific subunit comprises a full-length immunoglobulin (such as a monoclonal antibody) or an antigen-binding domain thereof and the CD137-specific subunit comprises a lipocalin mutein. In some embodiments, the fusion polypeptide comprises amino acid sequences selected from the group consisting of SEQ ID NOs of 5 and 6, 7 and 8, 9 and 10, 11 and 12, 13 and 14 or 15 and 16.

In some other embodiments with respect to a fusion polypeptide of the disclosure, one of whose subunits comprises a full-length immunoglobulin, while the polypeptide is simultaneously engaging HER2/neu and CD137, the Fc function of the Fc region of the full-length immunoglobulin to Fc receptor-positive cell may be reduced or fully suppressed by protein engineering. This may be achieved, for example, by switching from the IgG1 backbone to IgG4, as IgG4 is known to display reduced Fc-gamma receptor interactions compared to IgG1. To further reduce the residual binding to Fc-gamma receptors, mutations may be introduced into the IgG4 backbone such as F234A and L235A. In addition, a S228P mutation may be introduced into the IgG4 backbone to minimize the exchange of IgG4 half-antibody. In some still further embodiments, an additional N297A mutation may be present in the immunoglobulin heavy chain of the fusion polypeptide in order to remove the natural glycosylation motif; Example 7 provides evidence that modifying the subclass of an isotype or engineering an isotype results in loss of Fc-receptor binding.

In some other embodiments with respect to a fusion polypeptide of the disclosure, one of whose subunits comprises a full-length immunoglobulin, while the polypeptide is simultaneously engaging HER2/neu and CD137, the Fc function of the Fc region of the full-length immunoglobulin to neonatal Fc receptor (FcRn)-positive cells, though the Fc region may be modified, e.g., by switching the isotype or subclass of an isotype or by engineering, e.g. by engineering an isotype as described herein, is retained. Example 8 provides evidence that Fc-modified or Fc-engineered Fc regions of a fusion polypeptide of the disclosure retain binding to FcRn.

In some embodiments, resulting from the simultaneous binding to HER2 on tumor cells and CD137 on the surface of effector cells from the immune system, such as T-cells or NK cells, the fusion polypeptides of the disclosure may exhibit HER2-dependent effector-cell activation, whereby the effector cell of the immune system actively lyses the HER2-expressing tumor cell.

In some additional embodiments, the fusion polypeptide is capable of demonstrating comparable or superior level of HER2-dependent CD137 activation as the immunoglobulin included in such fusion polypeptide, for example, when measured in an assay demonstrating target-dependent tumor-infiltrating lymphocyte expansion ex-vivo as essentially described in Chacon, J. A. et al., PloS one 2013 8(4):e60031. In some additional embodiments, the fusion polypeptide is capable of demonstrating comparable or superior level of HER2-dependent CD137 activation as the immunoglobulin included in such fusion polypeptide, for example, when measured in an in-vivo xenotransplant model of human breast cancer, as essentially described in Kohrt, H. et al, J Clin Invest. 2012 March; 122(3):1066-75.

In some embodiments, the Fc portion of the immunoglobulin included in a fusion polypeptide of the disclosure may contribute to maintaining the serum levels of the fusion polypeptide, critical for its stability and persistence in the body. For example, when the Fc portion binds to Fc receptors on endothelial cells and on phagocytes, the fusion polypeptide may become internalized and recycled back to the blood stream, enhancing its half-life within body.

In some embodiments, a fusion polypeptide of the disclosure may be able to bind CD137 with an EC50 value at least as good as or superior to the EC50 value of the lipocalin mutein specific for CD137 as included in such fusion polypeptide, such as lipocalin muteins of SEQ ID NO: 2, for example, when said lipocalin mutein and the polypeptide are measured in an ELISA assay essentially as described in Example 3.

In some embodiments, the fusion polypeptide may be able to bind CD137 with an EC50 value of at least about 1 nM or even lower, such as about 0.6 nM, about 0.5 nM, about 0.4 nM or about 0.3 nM, for example, when the polypeptide is measured in an ELISA assay essentially as described in Example 3.

In some embodiments, a fusion polypeptide of the disclosure may be able to bind HER2/neu with an EC50 value comparable to the EC50 value of the immunoglobulin specific for HER2/neu as included in such fusion polypeptide, such as the antibody having the heavy and light chains provided by SEQ ID NOs: 3 and 4, for example, when said immunoglobulin and the fusion polypeptide are measured in as ELISA assay essentially as described in Example 2.

In another aspect, the fusion polypeptide may be able to bind HER2/neu to its ligand with an EC50 value of at least about 1 nM or even lower, such as about 0.4 nM, about 0.3 nM or about 0.2 nM, for example, when the polypeptide is measured in an ELISA assay essentially as described in Example 2.

In some embodiments, the fusion polypeptides of the disclosure specific for both CD137 and HER2/neu may be capable of simultaneously binding of CD137 and HER2/neu, for example, when said fusion polypeptide is measured in an ELISA assay essentially described in Example 4.

In some embodiments, the fusion polypeptides of the disclosure may be capable of co-stimulating T-cell responses in a functional T-cell activation assay essentially described in Example 5. In some embodiments, the fusion polypeptides of the disclosure may be able to induce IL-2 and/or IFN gamma secretion and T cell proliferation in a functional T-cell activation assay essentially described in Example 5. In some further embodiments, the fusion polypeptides of the disclosure may lead to successful T-cell activation in a functional T-cell activation assay essentially described in Example 5. In some further embodiments, the fusion polypeptides of the disclosure may lead to local induction of the production of IL-2 and/or IFN gamma by T-cells in the vicinity of HER2/neu-positive tumor cells essentially as described in Example 6. "In the vicinity of HER2/neu-positive cells" when used herein means a distance between a T-cell bound and a HER2/neu-positive tumor cell that are both bound, i.e. "linked" by one and the same fusion polypeptide of the present disclosure.

A. Exemplary Immunoglobulins as Included in the Fusion Polypeptides.

In some embodiments, with respect to the fusion polypeptide, the first binding domain comprises a full-length immunoglobulin or an antigen-binding domain thereof specific for HER2/neu. The immunoglobulin, for example, may be IgG1 or IgG4. In further embodiments, the immunoglobulin is a monoclonal antibody against HER2/neu. A few illustrative examples for such immunoglobulins include: Trastuzumab (trade names Herclon, Herceptin) and Pertuzumab (also called 2C4, trade name Perjeta).

B. Exemplary Lipocalin Muteins as Included in the Fusion Polypeptides.

As used herein, a "lipocalin" is defined as a monomeric protein of approximately 18-20 kDA in weight, having a cylindrical β-pleated sheet supersecondary structural region comprising a plurality of (preferably eight) β-strands connected pair-wise by a plurality of (preferably four) loops at one end to define thereby a binding pocket. It is the diversity of the loops in the otherwise rigid lipocalin scaffold that gives rise to a variety of different binding modes among the lipocalin family members, each capable of accommodating targets of different size, shape, and chemical character (reviewed, e.g., in Flower, D. R. (1996), supra; Flower, D. R. et al. (2000), supra, or Skerra, A. (2000) $Biochim.$ $Biophys. Acta$ 1482, 337-350). Indeed, the lipocalin family of proteins have naturally evolved to bind a wide spectrum of ligands, sharing unusually low levels of overall sequence conservation (often with sequence identities of less than 20%) yet retaining a highly conserved overall folding pattern. The correspondence between positions in various lipocalins is well known to one of skill in the art. See, for example, U.S. Pat. No. 7,250,297.

As noted above, a lipocalin is a polypeptide defined by its supersecondary structure, namely cylindrical β-pleated sheet supersecondary structural region comprising eight β-strands connected pair-wise by four loops at one end to define thereby a binding pocket. The present disclosure is not limited to lipocalin muteins specifically disclosed herein. In this regard, the disclosure relates to a lipocalin mutein having a cylindrical β-pleated sheet supersecondary structural region comprising eight β-strands connected pair-wise by four loops at one end to define thereby a binding pocket, wherein at least one amino acid of each of at least three of said four loops has been mutated and wherein said lipocalin is effective to bind CD137 with detectable affinity.

In one particular embodiment, a lipocalin mutein disclosed herein is a mutein of human tear lipocalin (TLPC or Tlc), also termed lipocalin-1, tear pre-albumin or von Ebner gland protein. The term "human tear lipocalin" or "Tlc" or "lipocalin-1" as used herein refers to the mature human tear lipocalin with the SWISS-PROT/UniProt Data Bank Accession Number P31025 (Isoform 1). The amino acid sequence shown in SWISS-PROT/UniProt Data Bank Accession Number P31025 may be used as a preferred "reference sequence", more preferably the amino acid sequence shown in SEQ ID NO: 17 is used as reference sequence.

In another particular embodiment, a lipocalin mutein disclosed herein is a mutein of human lipocalin 2. The term "human lipocalin 2" or "human Lcn 2" or "human NGAL" as used herein refers to the mature human neutrophil gelatinase-associated lipocalin (NGAL) with the SWISS-PROT/UniProt Data Bank Accession Number P80188. A human lipocalin 2 mutein of the disclosure may also be designated herein as "an hNGAL mutein". The amino acid sequence shown in SWISS-PROT/UniProt Data Bank Accession Number P80188 may be used as a preferred "reference sequence", more preferably the amino acid sequence shown in SEQ ID NO: 18 is used as reference sequence.

In some embodiments, a lipocalin mutein binding CD137 with detectable affinity may include at least one amino acid substitution of a native cysteine residue by another amino acid, for example, a serine residue. In some other embodiments, a lipocalin mutein binding CD137 with detectable affinity may include one or more non-native cysteine residues substituting one or more amino acids of a wild-type lipocalin. In a further particular embodiment, a lipocalin mutein according to the disclosure includes at least two amino acid substitutions of a native amino acid by a cysteine residue, hereby to form one or more cysteine briges. In some embodiments, said cysteine bridge may connect at least two loop regions. The definition of these regions is used herein in accordance with Flower (Flower, 1996, supra, Flower, et al., 2000, supra) and Breustedt et al. (2005, supra). In a related embodiment, the disclosure teaches one or more lipocalin muteins that are capable of activating downstream signaling pathways of CD137 by binding to CD137.

Proteins of the disclosure, which are directed against or specific for CD137, include any number of specific-binding protein muteins that are based on a defined protein scaffold. Preferably, the number of nucleotides or amino acids, respectively, that is exchanged, deleted or inserted is 1, 2, 3, 4, 5, 6, 7, 8, 9, 10, 11, 12, 13, 14, 15, 16, 17, 18, 19, 20 or more such as 25, 30, 35, 40, 45 or 50, with 1, 2, 3, 4, 5, 6, 7, 8, 9, 10, or 11 being preferred and 9, 10 or 11 being even more preferred. However, it is preferred that a lipocalin mutein of the disclosure is still capable of binding CD137.

In one aspect, the present disclosure includes various lipocalin muteins that bind CD137 with at least detectable affinity. In this sense, CD137 can be regarded a non-natural ligand of the reference wild-type lipocalin, where "non-natural ligand" refers to a compound that does not bind to wildtype lipocalins under physiological conditions. By engineering wildtype lipocalins with one or more mutations at certain sequence positions, the present inventors have demonstrated that high affinity and high specificity for the non-natural ligand, CD137, is possible. In some embodiments, at 1, 2, 3, 4, 5, 6, 7, 8, 9, 10, 11, 12 or even more nucleotide triplet(s) encoding certain sequence positions on wildtype lipocalins, a random mutagenesis may be carried out through substitution at these positions by a subset of nucleotide triplets.

Further, the lipocalin muteins of the disclosure may have a mutated amino acid residue at any one or more, including at least at any one, two, three, four, five, six, seven, eight, nine, ten, eleven or twelve, of the sequence positions corresponding to certain sequence positions of the linear polypeptide sequence of the reference lipocalin.

A protein of the disclosure may include the wild-type (natural) amino acid sequence of the "parental" protein scaffold (such as a lipocalin) outside the mutated amino acid sequence positions. In some embodiments, a lipocalin mutein according to the disclosure may also carry one or more amino acid mutations at a sequence position/positions as long as such a mutation does, at least essentially not hamper or not interfere with the binding activity and the folding of the mutein. Such mutations can be accomplished very easily on DNA level using established standard methods (Sambrook, J. et al. (2001) Molecular Cloning: A Laboratory Manual, 3rd Ed., Cold Spring Harbor Laboratory Press, Cold Spring Harbor, N.Y.). Illustrative examples of alterations of the amino acid sequence are insertions or deletions as well as amino acid substitutions. Such substitutions may be conservative, i.e. an amino acid residue is replaced with an amino acid residue of chemically similar properties, in particular with regard to polarity as well as size. Examples of conservative substitutions are the replacements among the members of the following groups: 1) alanine, serine, and threonine; 2) aspartic acid and glutamic acid; 3) asparagine and glutamine; 4) arginine and lysine; 5) isoleucine, leucine, methionine, and valine; and 6) phenylalanine, tyrosine, and tryptophan. On the other hand, it is also possible to introduce non-conservative alterations in the amino acid sequence. In addition, instead of replacing single amino acid residues, it is also possible to either insert or delete one or more continuous amino acids of the primary structure of the human tear lipocalin as long as these deletions or insertion result in a stable folded/functional mutein (for example, Tlc muteins with truncated N- and C-terminus). In such mutein, for instance, one or more amino acid residues are added or deleted at the N- or C-terminus of the polypeptide. Generally such a mutein may have about at least 70%, including at least about 80%, such as at least about 85% amino acid sequence identity, with the amino acid sequence of the mature human tear lipocalin. As an illustrative example, the present disclosure also encompasses Tlc muteins as defined above, in which the first four N-terminal amino acid residues of the sequence of mature human tear lipocalin (His-His-Leu-Leu; positions 1-4) and/or the last two C-terminal amino acid residues (Ser-Asp; positions 157-158) of the linear polypeptide sequence of the mature human tear lipocalin have been deleted (SEQ ID NOs: 32-38). In addition, as another illustrative example, the present disclosure also encompasses NGAL muteins as defined above, in which amino acid residues (Lys-Asp-Pro, positions 46-48) of the linear polypeptide sequence of the mature human lipocalin 2 (hNGAL) have be deleted (SEQ ID NO: 42).

The amino acid sequence of a lipocalin mutein disclosed herein has a high sequence identity to the reference lipocalin when compared to sequence identities with other lipocalins. In this general context, the amino acid sequence of a lipocalin mutein of the disclosure is at least substantially similar to the amino acid sequence of the reference lipocalin, with the proviso that possibly there are gaps (as defined below) in an alignment that are the result of additions or deletions of amino acids. A respective sequence of a lipocalin mutein of the disclosure, being substantially similar to the sequences of the reference lipocalin, has, in some embodiments, at least 70% identity or sequence homology, at least 75% identity or sequence homology, at least 80% identity or sequence homology, at least 82% identity or sequence homology, at least 85% identity or sequence homology, at least 87% identity or sequence homology, or at least 90% identity or sequence homology including at least 95% identity or sequence homology, to the sequence of the reference lipocalin, with the proviso that the altered position or sequence is retained and that one or more gaps are possible.

As used herein, a lipocalin mutein of the disclosure "specifically binds" a target (for example, CD137) if it is able to discriminate between that target and one or more reference targets, since binding specificity is not an absolute, but a relative property. "Specific binding" can be determined, for example, in accordance with Western blots, ELISA-, RIA-, ECL-, IRMA-tests, FACS, IHC and peptide scans.

In one embodiment, the lipocalin muteins of the disclosure are fused at its N-terminus and/or its C-terminus to a fusion partner which is a protein domain that extends the serum half-life of the mutein. In further particular embodiments, the protein domain is a Fc part of an immunoglobulin, a CH3 domain of an immunoglobulin, a CH4 domain of an immunoglobulin, an albumin binding peptide, or an albumin binding protein.

In another embodiment, the lipocalin muteins of the disclosure are conjugated to a compound that extends the serum half-life of the mutein. More preferably, the mutein is conjugated to a compound selected from the group consisting of a polyalkylene glycol molecule, a hydroethylstarch, an Fc part of an immunoglobulin, a CH3 domain of an immoglobulin, a CH4 domain of an immunoglobulin, an albumin binding peptide, and an albumin binding protein.

In yet another embodiment, the current disclosure relates to a nucleic acid molecule comprising a nucleotide sequence encoding a lipocalin mutein disclosed herein. The disclosure encompasses a host cell containing said nucleic acid molecule.

In one aspect, the present disclosure provides human lipocalin muteins that bind CD137 and useful applications therefor. The disclosure also provides methods of making CD137 binding proteins described herein as well as compositions comprising such proteins. CD137 binding proteins of the disclosure as well as compositions thereof may be used in methods of detecting CD137 in a sample or in methods of binding of CD137 in a subject. No such human lipocalin muteins having these features attendant to the uses provided by present disclosure have been previously described.

1. Exemplary Lipocalin Muteins Specific for CD137.

In one aspect, the present disclosure provides CD137-binding human tear lipocalin muteins.

In this regard, the disclosure provides one or more Tlc muteins that are capable of binding CD137 with an affinity measured by a KD of about 300 nM or lower and even about 100 nM or lower.

In some embodiments, such Tlc mutein comprises a mutated amino acid residue at one or more positions corresponding to positions 5, 26-31, 33-34, 42, 46, 52, 56, 58, 60-61, 65, 71, 85, 94, 101, 104-106, 108, 111, 114, 121, 133, 148, 150 and 153 of the linear polypeptide sequence of the mature human tear lipocalin (SEQ ID NO: 17).

In some particular embodiments, such Tlc mutein may contain a mutated amino acid residue at one or more positions corresponding to positions 26-34, 55-58, 60-61, 65, 104-106 and 108 of the linear polypeptide sequence of the mature human tear lipocalin.

In further particular embodiments, such Tlc mutein may further include a mutated amino acid residue at one or more positions corresponding to positions 101, 111, 114 and 153 of the linear polypeptide sequence of the mature human tear lipocalin.

In other particular embodiments, the Tlc may contain a mutated amino acid residue at one or more positions corresponding to positions 5, 26-31, 33-34, 42, 46, 52, 56, 58, 60-61, 65, 71, 85, 94, 101, 104-106, 108, 111, 114, 121, 133, 148, 150 and 153 of the linear polypeptide sequence of the mature human tear lipocalin.

In some further embodiments, the Tlc mutein may comprise at least 1, 2, 3, 4, 5, 6, 7, 8, 9, 10, 11, 12, 13, 14, 15, 16, 17, 18, 19, 20, 21, 22, 23, 24, 25, 26 or even more, mutated amino acid residues at one or more sequence positions corresponding to sequence positions 5, 26-31, 33-34, 42, 46, 52, 56, 58, 60-61, 65, 71, 85, 94, 101, 104-106, 108, 111, 114, 121, 133, 148, 150 and 153 of the linear polypeptide sequence of the mature human tear lipocalin and wherein said polypeptide binds CD137, in particular human CD137.

In some still further embodiments, the disclosure relates to a polypeptide, wherein said polypeptide is a Tlc mutein, in comparison with the linear polypeptide sequence of the mature human tear lipocalin, comprising at least 1, 2, 3, 4, 5, 6, 7, 8, 9, 10, 11, 12 or even more, mutated amino acid residues at the sequence positions 526-34, 55-58, 60-61, 65, 104-106 and 108 and wherein said polypeptide binds CD137, in particular human CD137.

In some embodiments, a lipocalin mutein according to the disclosure may include at least one amino acid substitution of a native cysteine residue by e.g. a serine residue. In some embodiments, a Tlc mutein according to the disclosure includes an amino acid substitution of a native cysteine residue at positions 61 and/or 153 by another amino acid such as a serine residue. In this context it is noted that it has been found that removal of the structural disulfide bond (on the level of a respective nave nucleic acid library) of wild-type tear lipocalin that is formed by the cysteine residues 61 and 153 (cf. Breustedt, et al., 2005, supra) may provide tear lipocalin muteins that are not only stably folded but are also able to bind a given non-natural ligand with high affinity. In some particular embodiments, the Tlc mutein according to the disclosure includes the amino acid substitutions Cys 61→Ala, Phe, Lys, Arg, Thr, Asn, Gly, Gln, Asp, Asn, Leu, Tyr, Met, Ser, Pro or Trp and Cys 153→Ser or Ala. Such a substitution has proven useful to prevent the formation of the naturally occurring disulphide bridge linking Cys 61 and Cys 153, and thus to facilitate handling of the mutein. However, tear lipocalin muteins that binds CD137 and that have the disulphide bridge formed between Cys 61 and Cys 153 are also part of the present disclosure.

In some embodiments, the elimination of the structural disulde bond may provide the further advantage of allowing for the (spontaneous) generation or deliberate introduction of non-natural artificial disulfide bonds into muteins of the disclosure, thereby increasing the stability of the muteins. For example, in some embodiments, either two or all three of the cysteine codons at position 61, 101 and 153 are replaced by a codon of another amino acid. Further, in some embodiments, a Tlc mutein according to the disclosure includes an amino acid substitution of a native cysteine residue at position 101 by a serine residue or a histidine residue.

In some embodiments, a mutein according to the disclosure includes an amino acid substitution of a native amino acid by a cysteine residue at positions 28 or 105 with respect to the amino acid sequence of mature human tear lipocalin.

Further, in some embodiments, a mutein according to the disclosure includes an amino acid substitution of a native arginine residue at positions 111 by a proline residue. Further, in some embodiments, a mutein according to the disclosure includes an amino acid substitution of a native lysine residue at positions 114 by a tryptophan residue or a glutamic acid.

In some embodiments, a CD137-binding Tlc mutein according to the disclosure includes, at one or more positions corresponding to positions 5, 26-31, 33-34, 42, 46, 52, 56, 58, 60-61, 65, 71, 85, 94, 101, 104-106, 108, 111, 114, 121, 133, 148, 150 and 153 of the linear polypeptide sequence of the mature human tear lipocalin (SEQ ID NO: 17), one or more of the following mutated amino acid residues: Ala 5→Val or Thr; Arg 26→Glu; Glu 27→Gly; Phe 28→Cys; Pro 29→Arg; Glu 30→Pro; Met 31→Trp; Leu 33→Ile; Glu 34→Phe; Thr 42→Ser; Gly 46→Asp; Lys 52→Glu; Leu 56→Ala; Ser 58→Asp; Arg 60→Pro; Cys 61→Ala; Lys 65→Arg or Asn; Thr 71→Ala; Val 85→Asp; Lys 94→Arg or Glu; Cys 101→Ser; Glu 104→Val; Leu 105→Cys; His 106→Asp; Lys 108→Ser; Arg 111→Pro; Lys 114→Trp; Lys 121→Glu; Ala 133→Thr; Arg 148→Ser; Ser 150→Ile and Cys 153→Ser. In some embodiments, a Tlc mutein according to the disclosure includes two or more, such as 3, 4, 5, 6, 7, 8, 9, 10, 11, 12, even more such as 13, 14, 15, 16, 17, 18, 19, 20, 21, 22, 23, 24, 25, 26 or all mutated amino acid residues at these sequence positions of the mature human tear lipocalin.

In some additional embodiments, the Tlc mutein binding CD137 includes one of the following sets of amino acid substitutions in comparison with the linear polypeptide sequence of the mature human tear lipocalin:
1. Arg 26→Glu; Glu 27→Gly; Phe 28→Cys; Pro 29→Arg; Glu 30→Pro; Met 31→Trp; Leu 33→Ile; Glu 34→Phe; Leu 56→Ala; Ser 58→Asp; Arg 60→Pro; Cys 61→Ala; Cys 101→Ser; Glu 104→Val; Leu 105→Cys; His 106→Asp; Lys 108→Ser; Arg 111→Pro; Lys 114→Trp; Cys 153→Ser;
2. Ala 5→Thr; Arg 26→Glu; Glu 27→Gly; Phe 28→Cys; Pro 29→Arg; Glu 30→Pro; Met 31→Trp; Leu 33→Ile; Glu 34→Phe; Leu 56→Ala; Ser 58→Asp; Arg 60→Pro; Cys 61→Ala; Lys 65→Arg; Val 85→Asp; Cys 101→Ser; Glu 104→Val; Leu 105→Cys; His 106→Asp; Lys 108→Ser; Arg 111→Pro; Lys 114→Trp; Lys 121→Glu; Ala 133→Thr; Cys 153→Ser; 157→Pro;
3. Arg 26→Glu; Glu 27→Gly; Phe 28→Cys; Pro 29→Arg; Glu 30→Pro; Met 31→Trp; Leu 33→Ile; Glu 34→Phe; Leu 56→Ala; Ser 58→Asp; Arg 60→Pro; Cys 61→Ala; Lys 65→Asn; Lys 94→Arg; Cys 101→Ser; Glu 104→Val; Leu 105→Cys; His 106→Asp; Lys 108→Ser; Arg 111→Pro; Lys 114→Trp; Lys 121→Glu; Ala 133→Thr; Cys 153→Ser;
4. Ala 5→Val; Arg 26→Glu; Glu 27→Gly; Phe 28→Cys; Pro 29→Arg; Glu 30→Pro; Met 31→Trp; Leu 33→Ile; Glu 34→Phe; Leu 56→Ala; Ser 58→Asp; Arg 60→Pro; Cys 61→Ala; Lys 65→Arg; Lys 94→Glu; Cys 101→Ser; Glu 104→Val; Leu 105→Cys; His 106→Asp; Lys 108→Ser; Arg 111→Pro; Lys 114→Trp; Lys 121→Glu; Ala 133→Thr; Cys 153→Ser; 157→Pro;
5. Arg 26→Glu; Glu 27→Gly; Phe 28→Cys; Pro 29→Arg; Glu 30→Pro; Met 31→Trp; Leu 33→Ile; Glu 34→Phe; Thr 42→Ser; Leu 56→Ala; Ser 58→Asp; Arg 60→Pro; Cys 61→Ala; Cys 101→Ser; Glu 104→Val; Leu 105→Cys; His 106→Asp; Lys 108→Ser; Arg 111→Pro; Lys 114→Trp; Ser 150→Ile; Cys 153→Ser; 157→Pro;
6. Arg 26→Glu; Glu 27→Gly; Phe 28→Cys; Pro 29→Arg; Glu 30→Pro; Met 31→Trp; Leu 33→Ile; Glu 34→Phe; Lys 52→Glu; Leu 56→Ala; Ser 58→Asp; Arg 60→Pro; Cys 61→Ala; Thr 71→Ala; Cys 101→Ser; Glu 104→Val; Leu 105→Cys; His 106→Asp; Lys 108→Ser; Arg 111→Pro; Lys 114→Trp; Ala 133→Thr; Arg 148→Ser; Ser 150→Ile; Cys 153→Ser; 157→Pro; or
7. Ala 5→Thr; Arg 26→Glu; Glu 27→Gly; Phe 28→Cys; Pro 29→Arg; Glu 30→Pro; Met 31→Trp; Leu 33→Ile; Glu 34→Phe; Gly 46→Asp; Leu 56→Ala; Ser 58→Asp; Arg 60→Pro; Cys 61→Ala; Thr 71→Ala; Cys 101→Ser; Glu 104→Val; Leu 105→Cys; His 106→Asp; Lys 108→Ser; Arg 111→Pro; Lys 114→Trp; Ser 150→Ile; Cys 153→Ser; 157→Pro.

In the residual region, i.e. the region differing from sequence positions 5, 26-31, 33-34, 42, 46, 52, 56, 58, 60-61, 65, 71, 85, 94, 101, 104-106, 108, 111, 114, 121, 133, 148, 150 and 153, a Tlc mutein of the disclosure may include the wild-type (natural) amino acid sequence outside the mutated amino acid sequence positions.

In still further embodiments, a Tlc mutein according to the current disclosure has at least 70% sequence identity or at least 70% sequence homology to the sequence of the mature human tear lipocalin (SEQ ID NO: 17).

In further particular embodiments, a Tlc mutein of the disclosure comprises an amino acid sequence as set forth in any one of SEQ ID NOs: 32-38 or a fragment or variant thereof.

In further particular embodiments, a Tlc mutein of the disclosure has at least 75%, at least 80%, at least 85% or higher sequence identity to an amino acid sequence selected from the group consisting of SEQ ID NOs: 32-38.

The disclosure also includes structural homologues of a Tlc mutein having an amino acid sequence selected from the group consisting of SEQ ID NOs: 32-38, which structural homologues have an amino acid sequence homology or sequence identity of more than about 60%, preferably more than 65%, more than 70%, more than 75%, more than 80%, more than 85%, more than 90%, more than 92% and most preferably more than 95% in relation to said Tlc mutein.

A Tlc mutein according to the present disclosure can be obtained by means of mutagenesis of a naturally occurring form of human tear lipocalin. In some embodiments of the mutagenesis, a substitution (or replacement) is a conservative substitution. Nevertheless, any substitution—including non-conservative substitution or one or more from the exemplary substitutions below—is envisaged as long as the lipocalin mutein retains its capability to bind to CD137, and/or it has a sequence identity to the then substituted sequence in that it is at least 60%, such as at least 65%, at least 70%, at least 75%, at least 80%, at least 85% or higher sequence identity to the amino acid sequence of the mature human tear lipocalin (SWISS-PROT Data Bank Accession Number P31025).

In some particular embodiments, the present disclosure provides a Tlc mutein that binds CD137 with an affinity measured by a KD of about 200 nM or lower.

In some additional embodiments, a Tlc mutein of the disclosure does not interfere with the binding of CD137L to CD137.

In another aspect, the present disclosure relates to novel, specific-binding human lipocalin 2 (human Lcn2 or hNGAL) muteins directed against or specific for CD137.

In this regard, the disclosure provides one or more hNGAL muteins that are capable of binding CD137 with an affinity measured by a KD of 200 nM or lower, about 140 nM or lower, about 50 nM or lower, and even about 10 nM or lower. More preferably, the hNGAL muteins can have an affinity measured by a KD of about 5 nM or lower.

In some embodiments, an hNGAL mutein of the disclosure includes at one or more positions corresponding to positions 28, 36, 40-41, 49, 52, 65, 68, 70, 72-73, 77, 79, 81, 83, 87, 94, 96, 100, 103, 106, 125, 127, 132 and 134 of the linear polypeptide sequence of the mature hNGAL (SEQ ID NO: 18) a substitution.

In particular embodiments, a lipocalin mutein of the disclosure comprises at least 1, 2, 3, 4, 5, 6, 7, 8, 9, 10, 11, 12, 13, 14, 15, 16, 17, 18, 19, 20, 21, or even more, substitution(s) at a sequence position corresponding to sequence position 28, 36, 40-41, 49, 52, 65, 68, 70, 72-73, 77, 79, 81, 83, 87, 94, 96, 100, 103, 106, 125, 127, 132 and 134 of the linear polypeptide sequence of the mature hNGAL (SWISS-PROT Data Bank Accession Number P80188; SEQ ID NO: 2). Preferably, it is envisaged that the disclosure relates to a lipocalin mutein which comprises, in addition to one or more substitutions at positions corresponding to positions 36, 87 and/or 96 of the linear polypeptide sequence of the mature human NGAL, at one or more positions corresponding to positions 28, 40-41, 49, 52, 65, 68, 70, 72-73, 77, 79, 81, 83, 94, 100, 103, 106, 125, 127, 132 and 134 of the linear polypeptide sequence of the mature hNGAL a substitution.

In some still further embodiments, the disclosure relates to a polypeptide, wherein said polypeptide is an hNGAL mutein, in comparison with the linear polypeptide sequence of the mature hNGAL (SWISS-PROT Data Bank Accession Number P80188; SEQ ID NO: 18), comprising at least 1, 2, 3, 4, 5, 6, 7, 8, 9, 10, 11, 12, 13, 14, 15, 16, 17, 18, 19, 20, 21, or even more, mutated amino acid residues at the sequence positions 28, 36, 40-41, 49, 52, 65, 68, 70, 72-73, 77, 79, 81, 87, 96, 100, 103, 106, 125, 127, 132 and 134, and wherein said polypeptide binds CD137, in particular human CD137.

In some embodiments, a CD137-binding hNGAL mutein of the disclosure includes, at any one or more of the sequence positions 28, 36, 40-41, 49, 52, 65, 68, 70, 72-73, 77, 79, 81, 83, 87, 94, 96, 100, 103, 106, 125, 127, 132 and 134 of the linear polypeptide sequence of the mature hNGAL (SEQ ID NO: 18), one or more of the following mutated amino acid residues: Gln 28→His; Leu 36→Gln; Ala 40→Ile; Ile 41→Arg or Lys; Gln 49→Val, Ile, His, Ser or Asn; Tyr 52→Met; Asn 65→Asp; Ser 68→Met, Ala or Gly; Leu 70→Ala, Lys, Ser or Thr; Arg 72→Asp; Lys 73→Asp; Asp 77→Met, Arg, Thr or Asn; Trp 79→Ala or Asp; Arg 81→Met, Trp or Ser; Phe 83→Leu; Cys 87→Ser; Leu 94→Phe; Asn 96→Lys; Tyr 100→Phe; Leu 103→His; Tyr 106→Ser; Lys 125→Phe; Ser 127→Phe; Tyr 132→Glu and Lys 134→Tyr.

In some embodiments, an hNGAL mutein of the disclosure includes two or more, such as 3, 4, 5, 6, 7, 8, 9, 10, 11, 12, even more such as 13, 14, 15, 16, 17, 18, 19, 20, 21, 22, 23, 24 or all mutated amino acid residues at these sequence positions of the mature hNGAL.

In some additional embodiments, an hNGAL mutein of the disclosure, which binds to CD137 includes the following amino acid replacements in comparison with the linear polypeptide sequence of the mature hNGAL:

(a) Gln 28→His; Leu 36→Gln; Ala 40→Ile; Ile 41→Lys; Gln 49→Asn; Tyr 52→Met; Ser 68→Gly; Leu 70→Thr; Arg 72→Asp; Lys 73→Asp; Asp 77→Thr; Trp 79→Ala; Arg 81→Ser; Cys 87→Ser; Asn 96→Lys; Tyr 100→Phe; Leu 103→His; Tyr 106→Ser; Lys 125→Phe; Ser 127→Phe; Tyr 132→Glu; Lys 134→Tyr;

(b) Gln 28→His; Leu 36→Gln; Ala 40→Ile; Ile 41→Arg; Gln 49→Ile; Tyr 52→Met; Asn 65→Asp; Ser 68→Met; Leu 70→Lys; Arg 72→Asp; Lys 73→Asp; Asp 77→Met; Trp 79→Asp; Arg 81→Trp; Cys 87→Ser; Asn 96→Lys; Tyr 100→Phe; Leu 103→His; Tyr 106→Ser; Lys 125→Phe; Ser 127→Phe; Tyr 132→Glu; Lys 134→Tyr;

(c) Gln 28→His; Leu 36→Gln; Ala 40→Ile; Ile 41→Arg; Gln 49→Asn; Tyr 52→Met; Asn 65→Asp; Ser 68→Ala; Leu 70→Ala; Arg 72→Asp; Lys 73→Asp; Asp 77→Thr; Trp 79→Asp; Arg 81→Trp; Cys 87→Ser; Asn 96→Lys; Tyr 100→Phe; Leu 103→His; Tyr 106→Ser; Lys 125→Phe; Ser 127→Phe; Tyr 132→Glu; Lys 134→Tyr;

(d) Gln 28→His; Leu 36→Gln; Ala 40→Ile; Ile 41→Lys; Gln 49→Asn; Tyr 52→Met; Asn 65→Asp; Ser 68→Ala; Leu 70→Ala; Arg 72→Asp; Lys 73→Asp; Asp 77→Thr; Trp 79→Asp; Arg 81→Trp; Cys 87→Ser; Asn 96→Lys; Tyr 100→Phe; Leu 103→His; Tyr 106→Ser; Lys 125→Phe; Ser 127→Phe; Tyr 132→Glu; Lys 134→Tyr;

(e) Gln 28→His; Leu 36→Gln; Ala 40→Ile; Ile 41→Lys; Gln 49→Ser; Tyr 52→Met; Asn 65→Asp; Ser 68→Gly; Leu 70→Ser; Arg 72→Asp; Lys 73→Asp; Asp 77→Thr; Trp 79→Ala; Arg 81→Met; Cys 87→Ser; Asn 96→Lys; Tyr 100→Phe; Leu 103→His; Tyr 106→Ser; Lys 125→Phe; Ser 127→Phe; Tyr 132→Glu; Lys 134→Tyr;

(f) Gln 28→His; Leu 36→Gln; Ala 40→Ile; Ile 41→Lys; Gln 49→Val; Tyr 52→Met; Asn 65→Asp; Ser 68→Gly; Leu 70→Thr; Arg 72→Asp; Lys 73→Asp; Asp 77→Arg; Trp 79→Asp; Arg 81→Ser; Cys 87→Ser; Leu 94→Phe; Asn 96→Lys; Tyr 100→Phe; Leu 103→His; Tyr 106→Ser; Lys 125→Phe; Ser 127→Phe; Tyr 132→Glu; Lys 134→Tyr;

(g) Gln 28→His; Leu 36→Gln; Ala 40→Ile; Ile 41→Arg; Gln 49→His; Tyr 52→Met; Asn 65→Asp; Ser 68→Gly; Leu 70→Thr; Arg 72→Asp; Lys 73→Asp; Asp 77→Thr; Trp 79→Ala; Arg 81→Ser; Cys 87→Ser; Asn 96→Lys; Tyr 100→Phe; Leu 103→His; Tyr 106→Ser; Lys 125→Phe; Ser 127→Phe; Tyr 132→Glu; Lys 134→Tyr;

(h) Gln 28→His; Leu 36→Gln; Ala 40→Ile; Ile 41→Lys; Gln 49→Asn; Tyr 52→Met; Asn 65→Asp; Ser 68→Gly; Leu 70→Thr; Arg 72→Asp; Lys 73→Asp; Asp 77→Thr; Trp 79→Ala; Arg 81→Ser; Phe 83→Leu; Cys 87→Ser; Leu 94→Phe; Asn 96→Lys; Tyr 100→Phe; Leu 103→His; Tyr 106→Ser; Lys 125→Phe; Ser 127→Phe; Tyr 132→Glu; Lys 134→Tyr; or (i) Gln 28→His; Leu 36→Gln; Ala 40→Ile; Ile 41→Arg; Gln 49→Ser; Tyr 52→Met; Asn 65→Asp; Ser 68→Ala; Leu 70→Thr; Arg 72→Asp; Lys 73→Asp; Asp 77→Asn; Trp 79→Ala; Arg 81→Ser; Cys 87→Ser; Asn 96→Lys; Tyr 100→Phe; Leu 103→His; Tyr 106→Ser; Lys 125→Phe; Ser 127→Phe; Tyr 132→Glu; Lys 134→Tyr.

In the residual region, i.e. the region differing from sequence positions 28, 36, 40-41, 49, 52, 65, 68, 70, 72-73, 77, 79, 81, 83, 87, 94, 96, 100, 103, 106, 125, 127, 132 and 134, an hNGAL mutein of the disclosure may include the wild-type (natural) amino acid sequence outside the mutated amino acid sequence positions.

In another embodiment, the hNGAL mutein has at least 70% or even higher sequence identity to the amino acid sequence of the mature human lipocalin 2 (SWISS-PROT Data Bank Accession Number P80188).

In further particular embodiments, a lipocalin mutein according to the current disclosure comprises an amino acid sequence selected from the group consisting of SEQ ID NOs: 2 and 39-46 or a fragment or variant thereof.

The amino acid sequence of a CD137-binding hNGAL mutein of the disclosure may have a high sequence identity, such as at least 70%, at least 75%, at least 80%, at least 82%, at least 85%, at least 87%, at least 90% identity, including at least 95% identity, to a sequnce selected from the group consisting of SEQ ID NOs: 2 and 39-46.

The disclosure also includes structural homologues of an hNGAL mutein having an amino acid sequence selected from the group consisting of SEQ ID NOs: 2 and 39-46, which structural homologues have an amino acid sequence homology or sequence identity of more than about 60%, preferably more than 65%, more than 70%, more than 75%, more than 80%, more than 85%, more than 90%, more than 92% and most preferably more than 95% in relation to said hNGAL mutein.

An hNGAL mutein according to the present disclosure can be obtained by means of mutagenesis of a naturally occurring form of human lipocalin 2. In some embodiments of the mutagenesis, a substitution (or replacement) is a conservative substitution. Nevertheless, any substitution— including non-conservative substitution or one or more from the exemplary substitutions below—is envisaged as long as the lipocalin mutein retains its capability to bind to CD137, and/or it has an identity to the then substituted sequence in that it is at least 60%, such as at least 65%, at least 70%, at least 75%, at least 80%, at least 85% or higher identity to the amino acid sequence of the mature human lipocalin 2 (SWISS-PROT Data Bank Accession Number P80188).

In some particular embodiments, the present disclosure provides an hNGAL mutein that binds CD137 with an affinity measured by a KD of about 5 nM or lower.

C. Exemplary Uses, Applications and Production of the Fusion Polypeptides.

In some embodiments, fusion polypeptides of the disclosure may produce synergistic effect through dual-targeting CD137 and HER2. For example, as demonstrated in ex-vivo assays and mouse models, CD137 stimulation of NK-cells boosts the activity of Trastuzumab (Kohrt, H. et al, J Clin Invest. 2012 March; 122(3):1066-75) by enhancing NK-cell function and activity.

Numerous possible applications for the fusion polypeptides of the disclosure, therefore, exist in medicine.

In one aspect, the disclosure relates to the use of the fusion polypeptides disclosed herein for detecting CD137 and HER2 in a sample as well as a respective method of diagnosis.

In another aspect, the disclosure features the use of one or more fusion polypeptides disclosed herein or of one or more compositions comprising such polypeptides for simultaneously binding of CD137 and HER2/neu.

The present disclosure also involves the use of one or more fusion polypeptides as described for complex formation with CD137 and HER2.

Therefore, in a still further aspect of the disclosure, the disclosed one or more fusion polypeptides are used for the detection of CD137 and HER2. Such use may include the steps of contacting one or more said fusion polypeptides, under suitable conditions, with a sample suspected of containing CD137 and HER2, thereby allowing formation of a complex between the fusion polypeptides and CD137 and HER2, and detecting the complex by a suitable signal. The detectable signal can be caused by a label, as explained above, or by a change of physical properties due to the binding, i.e. the complex formation, itself. One example is surface plasmon resonance, the value of which is changed during binding of binding partners from which one is immobilized on a surface such as a gold foil.

The fusion polypeptides disclosed herein may also be used for the separation of CD137 and HER2. Such use may include the steps of contacting one or more said fusion polypeptides, under suitable conditions, with a sample supposed to contain CD137 and HER2, thereby allowing formation of a complex between the fusion polypeptides and CD137 and HER2, and separating the complex from the sample.

In still another aspect, the present disclosure features a diagnostic or analytical kit comprising a fusion polypeptide according to the disclosure.

In addition to their use in diagnostics, in yet another aspect, the disclosure contemplates a pharmaceutical composition comprising a fusion polypeptide of the disclosure and a pharmaceutically acceptable excipient.

Furthermore, the present disclosure provides fusion polypeptides that simultaneously bind CD137 and HER2 for use as anti-cancer agents and immune modulators. As such the fusion polypeptides of the present disclosure are envisaged to be used in a method of treatment or prevention of human diseases such as a variety of tumors including certain aggressive types of breast cancer. Accordingly, also provided are methods of treatment or prevention of human diseases such as a variety of tumors including certain aggressive types of breast cancer in a subject in need thereof, comprising administering to said subject a therapeutically effective amount of one or more fusion polypeptides of the disclosure.

By simultaneously targeting tumor cells where HER2/neu is expressed and activating natural killer (NK) cells in the host innate immune system adjacent to such tumor cells, the fusion polypeptide of the disclosure may increase targeted anti-tumor T cells activity, enhance anti-tumor immunity and, at the same time, have a direct inhibiting effect on tumor growth, thereby produce synergistic anti-tumor results. In addition, via locally inhibiting oncogene activity and inducing cell-mediated cytotoxicity by NK cells, the fusion polypeptide of the disclosure may reduce side effects of effector lymphocytes towards healthy cells, i.e. off-target toxicity.

In T cells CD137-mediated signaling leads to the recruitment of TRAF family members and activation of several kinases, including ASK-1, MKK, MAPK3/MAPK4, p38, and JNK/SAPK. Kinase activation is then followed by the activation and nuclear translocation of several transcription factors, including ATF-2, Jun, and NF-κB. In addition to augmenting suboptimal T cell receptor (TCR)-induced proliferation, CD137-mediated signaling protects T cells, and in particular, CD8+ T cells from activation-induced cell death (AICD).

The present disclosure encompasses the use of a fusion polypeptide of the disclosure or a composition comprising such fusion polypeptide for costimulating T-cells, and/or activating downstream signaling pathways of CD137 when engaging tumor cells where HER2/neu is expressed.

The present disclosure also features a method of costimulating T-cells and/or activating downstream signaling pathways of CD137 when engaging tumor cells where HER2/neu is expressed, comprising applying one or more fusion polypeptide s of the disclosure or of one or more compositions comprising such fusion polypeptides.

Furthermore, the present disclosure involves a method of activating downstream signaling pathways of CD137 when engaging tumor cells where HER2/neu is expressed, comprising applying one or more fusion polypeptides of the disclosure or of one or more compositions comprising such fusion polypeptides.

The present disclosure also contemplates a method of inducing T lymphocyte proliferation when engaging tumor cells where HER2/neu is expressed, comprising applying one or more fusion polypeptides of the disclosure or of one or more compositions comprising such fusion polypeptides.

The present disclosure encompasses the use of a fusion polypeptide of the disclosure or a composition comprising such fusion polypeptide for directing CD137 clustering and activation on T-cells to tumor cells where HER2/neu is expressed.

The present disclosure further provides a method of inducing a local T-cell response in the vicinity of HER2/neu-positive tumor cells, comprising applying such fusion polypeptides. "Local" means that upon binding T-cells via CD137 and engaging HER2/neu-positive tumor cells, T-cells produce cytokines, particularly IL-2 and/or IFN gamma in vicinity of the HER2/neu-positive cell. Such cytokines reflect activation of T-cells which may then be able to kill HER2/neu-positive tumor cells, either directly or indirectly by attracting other killer cells, such as T-cells or NK cells.

In another embodiment, the present disclosure also relates to nucleic acid molecules (DNA and RNA) that include nucleotide sequences encoding the fusion polypeptides disclosed herein. In yet another embodiment, the disclosure encompasses a host cell containing said nucleic acid molecule. Since the degeneracy of the genetic code permits substitutions of certain codons by other codons specifying the same amino acid, the disclosure is not limited to a specific nucleic acid molecule encoding a fusion polypeptide as described herein but encompasses all nucleic acid molecules that include nucleotide sequences encoding a functional polypeptide. In this regard, the present disclosure also relates to nucleotide sequences encoding the the fusion polypeptides of the disclosure.

In some embodiments, a nucleic acid molecule encoding a lipocalin mutein disclosed in this application, such as DNA, may be "operably linked" to another nucleic acid molecule encoding an immunoglobulin of the disclosure to allow expression of a fusion polypeptide disclosed herein. In this regard, an operable linkage is a linkage in which the sequence elements of one nucleic acid molecule and the sequence elements of another nucleic acid molecule are connected in a way that enables expression of the fusion polypeptide as a single polypeptide.

The disclosure also relates to a method for the production of a or a fusion polypeptide of the disclosure is produced starting from the nucleic acid coding for the polypeptide or any subunit therein by means of genetic engineering methods. In some embodiments, the method can be carried out in vivo, the polypeptide can, for example, be produced in a bacterial or eucaryotic host organism and then isolated from this host organism or its culture. It is also possible to produce a fusion polypeptide of the disclosure in vitro, for example by use of an in vitro translation system.

When producing the fusion polypeptide in vivo, a nucleic acid encoding such polypeptide is introduced into a suitable bacterial or eukaryotic host organism by means of recombinant DNA technology (as already outlined above). For this purpose, the host cell is first transformed with a cloning vector that includes a nucleic acid molecule encoding a fusion polypeptide as described herein using established standard methods. The host cell is then cultured under conditions, which allow expression of the heterologous DNA and thus the synthesis of the corresponding polypeptide. Subsequently, the polypeptide is recovered either from the cell or from the cultivation medium.

In one embodiment of the disclosure, the method includes subjecting at least one nucleic acid molecule encoding hNGAL to mutagenesis at nucleotide triplets coding for at least one, sometimes even more, of the sequence positions corresponding to the sequence positions 28, 40-52, 60, 68, 65, 70, 71-81, 87, 89, 96, 98, 100-106, 114, 118, 120, 125-137 and 145 of the linear polypeptide sequence of hNGAL (SEQ ID NO: 18).

In addition, in some embodiments, the naturally occurring disulphide bond between Cys 76 and Cys 175 may be removed in hNGAL muteins of the disclosure. Accordingly, such muteins can be produced in a cell compartment having a reducing redox milieu, for example, in the cytoplasma of Gram-negative bacteria.

The disclosure also includes nucleic acid molecules encoding the lipocalin muteins of the disclosure, which include additional mutations outside the indicated sequence positions of experimental mutagenesis. Such mutations are often tolerated or can even prove to be advantageous, for example if they contribute to an improved folding efficiency, serum stability, thermal stability or ligand binding affinity of the lipocalin muteins.

A nucleic acid molecule disclosed in this application may be "operably linked" to a regulatory sequence (or regulatory sequences) to allow expression of this nucleic acid molecule.

A nucleic acid molecule, such as DNA, is referred to as "capable of expressing a nucleic acid molecule" or capable "to allow expression of a nucleotide sequence" if it includes sequence elements which contain information regarding to transcriptional and/or translational regulation, and such sequences are "operably linked" to the nucleotide sequence encoding the polypeptide. An operable linkage is a linkage in which the regulatory sequence elements and the sequence to be expressed are connected in a way that enables gene expression. The precise nature of the regulatory regions necessary for gene expression may vary among species, but in general these regions include a promoter which, in prokaryotes, contains both the promoter per se, i.e. DNA elements directing the initiation of transcription, as well as DNA elements which, when transcribed into RNA, will signal the initiation of translation. Such promoter regions normally include 5' non-coding sequences involved in initiation of transcription and translation, such as the −35/−10 boxes and the Shine-Dalgarno element in prokaryotes or the TATA box, CAAT sequences, and 5'-capping elements in eukaryotes. These regions can also include enhancer or repressor elements as well as translated signal and leader sequences for targeting the native polypeptide to a specific compartment of a host cell.

In addition, the 3' non-coding sequences may contain regulatory elements involved in transcriptional termination, polyadenylation or the like. If, however, these termination sequences are not satisfactory functional in a particular host cell, then they may be substituted with signals functional in that cell.

Therefore, a nucleic acid molecule of the disclosure can include a regulatory sequence, such as a promoter sequence. In some embodiments a nucleic acid molecule of the disclosure includes a promoter sequence and a transcriptional termination sequence. Suitable prokaryotic promoters are, for example, the tet promoter, the/acUV5 promoter or the T7 promoter. Examples of promoters useful for expression in eukaryotic cells are the SV40 promoter or the CMV promoter.

The nucleic acid molecules of the disclosure can also be part of a vector or any other kind of cloning vehicle, such as a plasmid, a phagemid, a phage, a baculovirus, a cosmid or an artificial chromosome.

In one embodiment, the nucleic acid molecule is included in a phasmid. A phasmid vector denotes a vector encoding the intergenic region of a temperent phage, such as M13 or f1, or a functional part thereof fused to the cDNA of interest. After superinfection of the bacterial host cells with such an phagemid vector and an appropriate helper phage (e.g. M13K07, VCS-M13 or R408) intact phage particles are produced, thereby enabling physical coupling of the encoded heterologous cDNA to its corresponding polypeptide displayed on the phage surface (see e.g. Lowman, H. B. (1997) *Annu. Rev. Biophys. Biomol. Struct.* 26, 401-424, or Rodi, D. J., and Makowski, L. (1999) *Curr. Opin. Biotechnol.* 10, 87-93).

Such cloning vehicles can include, aside from the regulatory sequences described above and a nucleic acid sequence encoding a fusion polypeptide as described herein, replication and control sequences derived from a species compatible with the host cell that is used for expression as well as selection markers conferring a selectable phenotype on transformed or transfected cells. Large numbers of suitable cloning vectors are known in the art, and are commercially available.

The DNA molecule encoding a fusion polypeptide as described herein (for example, SEQ ID NOs: 20 and 31), and in particular a cloning vector containing the coding sequence of such a polypeptide can be transformed into a host cell capable of expressing the gene. Transformation can be performed using standard techniques. Thus, the disclosure is also directed to a host cell containing a nucleic acid molecule as disclosed herein.

The transformed host cells are cultured under conditions suitable for expression of the nucleotide sequence encoding a fusion polypeptide of the disclosure. Suitable host cells can be prokaryotic, such as *Escherichia coli* (*E. coli*) or *Bacillus subtilis*, or eukaryotic, such as *Saccharomyces cerevisiae*, *Pichia pastoris*, SF9 or High5 insect cells, immortalized mammalian cell lines (e.g., HeLa cells or CHO cells) or primary mammalian cells.

In some embodiments where a lipocalin mutein of the disclosure, including as comprised in in a fusion polypeptide disclosed herein, includes intramolecular disulphide bonds, it may be preferred to direct the nascent polypeptide to a cell compartment having an oxidizing redox milieu using an appropriate signal sequence. Such an oxidizing environment may be provided by the periplasm of Gram-negative bacteria such as *E. coli*, in the extracellular milieu of Gram-positive bacteria or in the lumen of the endoplasmatic reticulum of eukaryotic cells and usually favours the formation of structural disulphide bonds.

In some embodiments, it is also possible to produce a fusion polypeptide of the disclosure in the cytosol of a host cell, preferably *E. coli*. In this case, the polypeptide can either be directly obtained in a soluble and folded state or recovered in form of inclusion bodies, followed by renaturation in vitro. A further option is the use of specific host strains having an oxidizing intracellular milieu, which may thus allow the formation of disulfide bonds in the cytosol (Venturi et al. (2002) *J. Mol. Biol.* 315, 1-8.).

In some embodiments, a fusion polypeptide of the disclosure as described herein may be not necessarily generated or produced only by use of genetic engineering. Rather, such polypeptide can also be obtained by chemical synthesis such as Merrifield solid phase polypeptide synthesis or by in vitro transcription and translation. It is, for example, possible that promising mutations are identified using molecular modeling and then to synthesize the wanted (designed) mutein or polypeptide in vitro and investigate the binding activity for a target of interest. Methods for the solid phase and/or solution phase synthesis of proteins are well known in the art (see e.g. Bruckdorfer, T. et al. (2004) *Curr. Pharm. Biotechnol.* 5, 29-43).

In another embodiment, a fusion polypeptide of the disclosure may be produced by in vitro transcription/translation employing well-established methods known to those skilled in the art.

The skilled worker will appreciate methods useful to prepare fusion polypeptides contemplated by the present disclosure but whose protein or nucleic acid sequences are not explicitly disclosed herein. As an overview, such modifications of the amino acid sequence include, e.g., directed mutagenesis of single amino acid positions in order to simplify sub-cloning of a polypeptide gene or its parts by incorporating cleavage sites for certain restriction enzymes. In addition, these mutations can also be incorporated to further improve the affinity of a fusion polypeptide for its targets (e.g. CD137 and HER2). Furthermore, mutations can be introduced to modulate certain characteristics of the polypeptide such as to improve folding stability, serum stability, protein resistance or water solubility or to reduce aggregation tendency, if necessary. For example, naturally occurring cysteine residues may be mutated to other amino acids to prevent disulphide bridge formation.

Additional objects, advantages, and features of this disclosure will become apparent to those skilled in the art upon examination of the following Examples and the attached Figures thereof, which are not intended to be limiting. Thus, it should be understood that although the present disclosure is specifically disclosed by exemplary embodiments and optional features, modification and variation of the disclosures embodied therein herein disclosed may be resorted to by those skilled in the art, and that such modifications and variations are considered to be within the scope of this disclosure.

V. EXAMPLES

Example 1: Expression and Analysis of Fusion Polypeptides

To engage HER2 and CD137 at the same time, we generated several representative antibody-lipocalin mutein fusion polypeptides, fusing together the antibody having the heavy and light chains provided by SEQ ID NOs: 3 and 4, and the lipocalin mutein of SEQ ID NO: 2 via an unstructured (G4S)3 linker (SEQ ID NO: 19). The different formats that were designed are depicted in FIG. 1. Such fusion polypeptides (SEQ ID NOs: 9 and 10. SEQ ID NOs: 11 and 12, SEQ ID NOs: 13 and 14, SEQ ID NOs: 15 and 16) were generated via fusion of the lipocalin mutein of SEQ ID NO: 2 to either one of the four termini of a mutated variant of the antibody having an engineered IgG4 backbone, which contains a S228P mutation to minimize IgG4 half-antibody exchange in-vitro and in-vivo (cf. Silva 2015) as well as F234A and L235A mutations to reduce Fc-gamma receptor interactions (Alegre 1992). Furthermore, we generated the fusion polypeptide of SEQ ID NOs: 7 and 8, which, in comparison with the fusion polypeptide of SEQ ID NOs: 9 and 10 has an additional N297A mutation in the antibody heavy chain (cf. Bolt 1993) in order to remove the natural glycosylation motif. This removal could potentially further reduce the interaction with Fc-gamma receptors. In addition, we generated the fusion polypeptide of SEQ ID NOs: 5 and 6, which is a direct fusion of lipocalin mutein of SEQ ID NO: 2 to C-terminal heavy chain of the antibody of SEQ ID NOs: 3 and 4 with an IgG1 background and therefore the fusion polypeptide retains the original Fc-gamma interaction of the IgG1 antibody.

The constructs were generated by gene synthesis and cloned into a mammalian expression vector. They were then transiently expressed in CHO cells. The concentration of fusion polypeptides in the cell culture medium was measured using a ForteBio Protein A sensor (Pall Corp.) and quantified using a human IgG1 standard. The titers of the constructs were as described in Table 1 below.

TABLE 1

Expression titers

| Clone Name | Expression titer [mg/L] |
| --- | --- |
| SEQ ID NOs: 5 and 6 | 262 |
| SEQ ID NOs: 9 and 10 | 156 |
| SEQ ID NOs: 13 and 14 | 191 |
| SEQ ID NOs: 7 and 8 | 181 |
| SEQ ID NOs: 11 and 12 | 204 |
| SEQ ID NOs: 15 and 16 | 161 |

The fusion polypeptides were purified using Protein A chromatography followed by size-exclusion chromatography (SEC) in phosphate-buffered saline (PBS). After SEC purification the fractions containing monomeric protein were pooled and analyzed again using analytical SEC. According to this analysis, the fusion polypeptides were fully monomeric without detectable multimeric species or aggregates.

Example 2: Specificity of Fusion Polypeptides Towards HER2

We employed an ELISA assay to determine the affinity of the fusion proteins to recombinant HER2 (Sino Biological). The target was dissolved in PBS (5 µg/mL) and coated overnight on microtiter plates at 4° C. The plate was washed after each incubation step with 80 µL PBS supplemented with 0.05% (v/v) Tween 20 (PBS-T) five times. The plates were blocked with 2% BSA (w/v) in PBS for 1 h at room temperature and subsequently washed. Different concentrations of the benchmark antibody (SEQ ID NOs: 3 and 4, Trastuzumab or Herceptin®, Roche Diagnostics) or the fusion polypeptides were added to the wells and incubated for 1 h at room temperature, followed by a wash step. Bound agents under study were detected after incubation with 1:5000 diluted anti-human IgG Fc-HRP (#109-035-098, Jackson Laboratory) in PBS-T. After an additional wash step, fluorogenic HRP substrate (QuantaBlu, Thermo) was added to each well and the fluorescence intensity was detected using a fluorescence microplate reader.

The result of the experiment was plotted in FIG. 2, together with the fit curves resulting from a 1:1 binding sigmoidal fit, where the EC50 value and the maximum signal were free parameters, and the slope was fixed to unity. The resulting EC50 values are provided in Table 2 below, including the errors of the sigmoidal fit of the data. The observed EC50 values were in a similar range for all tested fusion polypeptides (0.22-0.31 nM), and in the same range as the EC50 value for the benchmark antibody (SEQ ID NOs: 3 and 4), which was at 0.16 nM.

TABLE 2

ELISA data for HER2 binding

| Agent Name | EC50 HER2 [nM] |
| --- | --- |
| SEQ ID NOs: 7 and 8 | 0.24 ± 0.02 |
| SEQ ID NOs: 13 and 14 | 0.23 ± 0.01 |
| SEQ ID NOs: 15 and 16 | 0.31 ± 0.01 |
| SEQ ID NOs: 5 and 6 | 0.22 ± 0.01 |
| SEQ ID NOs: 9 and 10 | 0.28 ± 0.01 |
| SEQ ID NOs: 11 and 12 | 0.23 ± 0.01 |
| SEQ ID NOs: 3 and 4 | 0.16 0.01 |

Example 3: Specificity of Fusion Polypeptides Towards CD137

We employed an ELISA assay to determine the affinity of the fusion polypeptides and the positive control lipocalin mutein of SEQ ID NO: 2 to a recombinant CD137-Fc fusion (#838-4B-100, R&D Systems). The target was dissolved in PBS (5 µg/mL) and coated overnight on microtiter plates at 4° C. The plate was washed after each incubation step with 80 µL PBS-T five times. The plates were blocked with 2% BSA (w/v) in PBS for 1 h at room temperature and subsequently washed. Different concentrations of the CD137-specific lipocalin mutein in monomeric form (SEQ ID NO: 2) or the fusion polypeptides were added to the wells and incubated for 1 h at room temperature, followed by a wash step. Bound agents under study were detected after incubation for 1 h at room temperature with 1:1000 diluted anti-hNGAL antibody conjugated to HRP in PBS-T. After an additional wash step, fluorogenic HRP substrate (QuantaBlu, Thermo) was added to each well and the fluorescence intensity was detected using a fluorescence microplate reader.

The result of the experiment is plotted was FIG. 3, together with the fit curves resulting from a 1:1 binding sigmoidal fit, where the EC50 value and the maximum signal were free parameters, and the slope was fixed to unity. The resulting EC50 values are provided in Table 3, including the errors of the sigmoidal fit of the data. The observed EC50 values for all tested fusion polypeptides were nearly identical within the experimental error and ranged from 0.30 nM to 0.47 nM, slightly superior to the value obtained for the positive control lipocalin mutein of SEQ ID NO: 2, which was 0.49 nM.

TABLE 3

ELISA data for CD137 binding

| Agent Name | EC50 CD137 [nM] |
| --- | --- |
| SEQ ID NOs: 7 and 8 | 0.30 ± 0.02 |
| SEQ ID NOs: 13 and 14 | 0.33 ± 0.05 |
| SEQ ID NOs: 15 and 16 | 0.35 ± 0.03 |
| SEQ ID NOs: 5 and 6 | 0.41 ± 0.04 |
| SEQ ID NOs: 9 and 10 | 0.37 ± 0.06 |
| SEQ ID NOs: 11 and 12 | 0.47 ± 0.06 |
| SEQ ID NO: 2 | 0.49 ± 0.09 |

Example 4: Demonstration of Simultaneous Target Binding in an ELISA-Based Setting In order to demonstrate the simultaneous binding of the fusion polypeptides to HER2 and CD137, a dual-binding ELISA format was used. Recombinant HER2 (Sino Biological) in PBS (5 µg/mL) was coated overnight on microtiter plates at 4° C. The plate was washed five times after each incubation step with 80 µL PBS supplemented with 0.05% (v/v) Tween 20 (PBS-T) using a Biotek ELx405 select CW washer. The plates were blocked with 2% BSA (w/v) in PBS for 1 h at room temperature and subsequently washed again. Different concentrations of the fusion polypeptides were added to the wells and incubated for 1 h at room temperature, followed by a wash step. Subsequently, biotinylated human CD137-Fc was added at a constant concentration of 1 µg/mL in PBS-T for 1 h. After washing, Extravidin-HRP (Sigma-Adrich, 1:5000 in PBS-T) was added to the wells for 1 h. After an additional wash step, fluorogenic HRP substrate (QuantaBlu, Thermo) was added to each well and the fluorescence intensity was detected using a fluorescence microplate reader.

The respective experimental data was plotted in FIG. 4. All tested fusion polypeptides showed clear binding signals with EC50 values ranging from 1-4 nM, demonstrating that these fusion polypeptides are able to engage HER2 and CD137 simultaneously.

Example 5: Functional T-Cell Activation Assay Using Coated Fusion Polypeptides

We employed a T-cell activation assay to assess the ability of the fusion polypeptide of SEQ ID NOs: 15 and 16 to co-stimulate T-cell responses. For this purpose, the fusion polypeptide of SEQ ID NOs: 15 and 16 at different concentrations was coated onto a plastic dish together with an anti-human CD3 antibody (OKT3, eBioscience) and purified T-cells were subsequently incubated on the coated surface. As readouts, we assessed continued proliferation of the T-cells after three days incubation using a 4 h BrdU pulse, and measured supernatant interleukin 2 (IL-2)) levels. In the following, we provide a detailed description of the experiment.

Human peripheral blood mononuclear cells (PBMC) from healthy volunteer donors were isolated from buffy coats by centrifugation through a Polysucrose density gradient (Biocoll 1.077 g/mL from Biochrom), following Biochrom's protocols. The T lymphocytes were isolated from the resulting PBMC using a Pan T-cell purification Kit (Miltenyi Biotec GmbH) and the manufacturer's protocols. Purified T-cells were resuspended in a buffer consisting of 90% FCS and 10% DMSO, immediately frozen down using liquid nitrogen and stored in liquid nitrogen until further use. For the assay, T cells were thawed for 16 h and cultivated in culture media (RPMI 1640, Life Technologies) supplemented with 10% FCS and 1% Penicillin-Streptomycin (Life Technologies).

The following procedure was performed using triplicates for each experimental condition. Flat-bottom tissue culture plates were coated overnight at 4° C. using 200 μL of a mixture of 0.5 μg/mL anti-CD3 antibody and the fusion polypeptide of SEQ ID NOs: 15 and 16 at a concentration of 3 μg/mL, 10 μg/mL and 30 μg/mL. As a negative control, the anti-CD3 antibody was captured alone, i.e. without the addition of the fusion polypeptide of SEQ ID NOs: 15 and 16. The following day, wells were washed twice with PBS, and 100 μL of the T-cell suspension (corresponding to 5×10$^4$ T cells) in culture media was added to each well. Plates were covered with a gas permeable seal (4titude) and incubated at 37° C. in a humidified 5% $CO_2$ atmosphere for 3 days. Subsequently, the IL-2 concentration in the supernatant, as well as cell proliferation, were assessed.

In order to quantify T-cell proliferation, the chemiluminescent cell proliferation ELISA kit based on BrdU incorporation (Roche) was used according to the manufacturer's instructions. Briefly, on day 3, 10 μL of BrdU labeling solution were added to each well and proliferation was allowed to proceed for a further 4 h at 37° C. under a humidified 5% $CO_2$ atmosphere. Plates were centrifuged at 300 g for 10 min and supernatants of the triplicates were pooled and immediately stored at −20° C. for later IL-2 quantification. Plates were subsequently dried at 60° C. for 1 hour. 200 μL of "FixDenat" solution were added to each well and the plates were incubated at room temperature for 30 min. Incorporated BRDU was labeled with a peroxidase-labelled anti-BrdU antibody by 2 h incubation at room temperature. BrdU levels were assessed by quantifying a chemiluminescent peroxidase-catalysed reaction in a PheraStar FS reader.

Human IL-2 levels in the cell culture supernatants were quantified using the IL-2 DuoSet DuoSet kit from R&D Systems. The procedure is carried out and described in the following. In the first step, a 384 well plate was coated at room temperature for 2 h with 1 μg/mL "Human IL-2 Capture Antibody" (R&D System) diluted in PBS. Subsequently, wells were washed 5 times with 80 μl PBS-T (PBS containing 0.05% Tween20) using a Biotek EL405 select CW washer (Biotek). After 1 h blocking in PBS-T additionally containing 1% casein (w/w), pooled supernatant and a concentration series of an IL-2 standard diluted in culture medium were incubated in the 384-well plate overnight at 4° C. To allow for detection and quantitation of captured IL-2, a mixture of 100 ng/mL biotinylated goat anti-hIL-2-Bio detection antibody (R&D System) and 1 μg/mL Sulfotag-labelled streptavidin (Mesoscale Discovery) were added in PBS-T containing 0.5% casein and incubated at room temperature for 1 h. After washing, 25 μL reading buffer was added to each well and the electrochemiluminescence (ECL) signal of every well was read using a Mesoscale Discovery reader. Analysis and quantification were performed using Mesoscale Discovery software.

The result for the assessment of T-cell proliferation is shown in FIG. 5. There is a significant increase in continued proliferation after 3 d incubation in the wells that were coated with 10 μg/mL and 30 μg/mL of the fusion polypeptide of SEQ ID NOs: 15 and 16, compared to the negative control which did not contain the fusion polypeptide of SEQ ID NOs: 15 and 16 and where the anti-CD3 antibody was captured alone.

The result of the IL-2 measurement shows that the fusion polypeptide of SEQ ID NOs: 15 and 16 can lead to successful T-cell activation (data not shown).

Example 6: Functional T-Cell Activation Assay Using Tumor Cell Bound Fusions Polypeptides We employed a target-cell dependent T-cell activation assay to assess the ability of the fusion polypeptides of SEQ ID NOs: 9 and 10, SEQ ID NOs: 11 and 12, SEQ ID NOs: 13 and 14, and SEQ ID NOs: 15 and 16 capable of binding CD137 and HER2 at the same time—to co-stimulate T-cell responses when immobilized on a HER2-positive cell line. As a negative control, we employed the monospecific, HER2-binding antibody of SEQ ID NOs: 3 and 4. As a further control, the experiment was performed in the presence of an excess of the monospecific, HER2-binding antibody of SEQ ID NOs: 3 and 4 in order to displace the bispecific constructs SEQ ID NOs: 9 and 10, SEQ ID NOs: 11 and 12, SEQ ID NOs: 13 and 14, and SEQ ID NOs: 15 and 16 from binding to HER2-positive cells. In the experiment, an anti-human CD3 antibody (OKT3, eBioscience) was coated on a plastic culture dish, and subsequently HER2-positive SKBR3 cells were cultured on the dish overnight. The next day, purified T-cells were incubated on the coated surface in the presence of various concentrations of the fusion polypeptides of SEQ ID NOs: 9 and 10, SEQ ID NOs: 11 and 12, SEQ ID NOs: 13 and 14, and SEQ ID NOs: 15 and 16 or the control antibody of SEQ ID NOs: 3 and 4. As readout, we measured supernatant interleukin 2 (IL-2) and interferon-γ (IFN-γ) levels. In the following, the experiment is described in detail.

Human peripheral blood mononuclear cells (PBMC) from healthy volunteer donors were isolated from buffy coats by centrifugation through a Polysucrose density gradient (Biocoll 1.077 g/mL from Biochrom), following Biochrom's protocols. The T lymphocytes were isolated from the resulting PBMC using a Pan T-cell purification Kit (Miltenyi Biotec GmbH) and the manufacturer's protocols. Purified T-cells were resuspended in a buffer consisting of 90% FCS and 10% DMSO, immediately frozen down using liquid nitrogen and stored in liquid nitrogen until further use. For the assay, T cells were thawed for 16 h and cultivated in culture media (RPMI 1640, Life Technologies) supplemented with 10% FCS and 1% Penicillin-Streptomycin (Life Technologies).

The following procedure was performed using triplicates for each experimental condition. Flat-bottom tissue culture plates were pre-coated or not for 1 h at 37° C. using 200 μL of 0.25 μg/mL anti-CD3 antibody. The plates were subsequently washed twice with PBS. $5 \times 10^4$ SKBR3 tumor cells per well were plated and allowed to adhere overnight at 37° C. in a humidified 5% $CO_2$ atmosphere. The SKBR3 cells had before been grown in culture under standard conditions, detached using Accutase and resuspended in culture media.

On the next days, tumor cells were treated 2 hours at 37° C. with mitomycin C (Sigma Aldrich) at a concentration of 30 μg/ml in order to block their proliferation. Plates were washed twice with PBS, and 100 μL of the T-cell suspension (corresponding to $5 \times 10^4$ T cells) and each of the four fusion polypeptides, at eleven different concentrations ranging from 25 μg/mL to 0.4 ng/mL, or the negative control at concentrations of 25 μg/mL, 0.1 μg/mL and 0.4 ng/mL, were added to each well. The same setup was performed in parallel, but with the addition of a final concentration of 50 μg/mL of the monospecific, HER2-binding antibody SEQ ID NOs: 3 and 4. Plates were covered with a gas permeable seal (4titude) and incubated at 37° C. in a humidified 5% $CO_2$ atmosphere for 3 days. Subsequently, IL-2 and IFN-γ concentration in the supernatant were assessed as described below.

Human IL-2 levels in the cell culture supernatants were quantified using the IL-2 DuoSet kit and the IFN-γ DuoSet kit from R&D Systems, respectively. The procedure is carried out analogously for both cytokines and described in the following for IL-2 only. In the first step, a 384 well plate was coated at room temperature for 2 h with 1 μg/mL "Human IL-2 Capture Antibody" (R&D System) diluted in PBS. Subsequently, wells were washed 5 times with 80 μl PBS-T (PBS containing 0.05% Tween20) using a Biotek EL405 select CW washer (Biotek). After 1 h blocking in PBS-T additionally containing 1% casein (w/w), pooled supernatant and a concentration series of an IL-2 standard diluted in culture medium were incubated in the 384-well plate overnight at 4° C. To allow for detection and quantitation of captured IL-2, a mixture of 100 ng/mL biotinylated goat anti-hIL-2-Bio detection antibody (R&D System) and 1 μg/mL Sulfotag-labelled streptavidin (Mesoscale Discovery) were added in PBS-T containing 0.5% casein and incubated at room temperature for 1 h. After washing, 25 μL reading buffer was added to each well and the electrochemiluminescence (ECL) signal of every well was read using a Mesoscale Discovery reader. Analysis and quantification were performed using Mesoscale Discovery software. The data was fitted with a 1:1 binding model with EC50 value, background level and plateau level as free parameters, and a slope that was fixed to unity. The induction factor was calculated from the fitted values as the quotient of plateau level and background level.

The result of a representative experiment for the bispecific fusion polypeptide SEQ ID NOs: 9 and 10 is depicted in FIG. 6. The data demonstrates a clear increase of supernatant levels for both IL-2 (FIG. 6A) and IFN-γ (FIG. 6C) with rising concentrations of the bispecific fusion polypeptide. At low concentrations of the bispecific fusion polypeptide, the IL-2 and IFN-γ concentration measured in the supernatant corresponds to the background level measured for the negative control SEQ ID NOs: 3 and 4. In the presence of an excess of the HER2-binder SEQ ID NOs: 3 and 4, the concentrations of both IL-2 (FIG. 6B) and IFN-γ (FIG. 6D) no longer show a SEQ ID NOs: 9 and 10-concentration-dependent increase, but remain invariant at the background level.

While the plateau levels reached in the experiment are lower for SEQ ID NOs: 11 and 12 (FIG. 7) and SEQ ID NOs: 15 and 16 (FIG. 9), overall results regarding concentration dependent induction of IL-2 and IFN-γ and blockade by an excess of SEQ ID NOs: 3 and 4 are similar. In contrast, there is no discernible increase in IL-2 or IFN-γ concentration with increasing concentration of the polypeptide fusion SEQ ID NOs: 13 and 14 (FIG. 8).

The EC50 values and induction factors resulting from a sigmoidal fit of the data are provided in Table 4, including data for an independent repeat of the experiment using a different PBMC donor. The data indicates that the EC50 values are comparable for SEQ ID NOs: 9 and 10, SEQ ID NOs: 11 and 12 and SEQ ID NOs: 15 and 16. However, the induction factor decreases in the order SEQ ID NOs: 9 and 10>SEQ ID NOs: 11 and 12>SEQ ID NOs: 15 and 16.

The experiment clearly demonstrates a potent functional activity of SEQ ID NOs: 9 and 10, SEQ ID NOs: 11 and 12 and SEQ ID NOs: 15 and 16, while SEQ ID NOs: 13 and 14 has no activity. In light of the nearly identical affinities for all constructs demonstrated in the Examples 4 and 5, this highlights the important role of construct geometry.

TABLE 4

| | Potency IL-2 [EC50] | Potency IFN-g [EC50] | Efficacy IL-2 (max/min) | Efficacy IFN-g (max/min) |
| --- | --- | --- | --- | --- |
| SEQ ID NOs: 9 and 10 | 0.49 nM (0.33/0.65) | 0.29 nM (0.25/0.33) | 7.1 (7.5/6.7) | 2.7 (2.5/2.8) |
| SEQ ID NOs: 11 and 12 | 0.65 nM (0.72/0.57) | 0.55 nM (0.45/0.64) | 5.5 (6.5/4.4) | 2.8 (2.9/2.7) |
| SEQ ID NOs: 13 and 14 | — | — | — | — |
| SEQ ID NOs: 15 and 16 | 0.53 nM (0.55/0.50) | 0.38 nM (0.45/0.30) | 3.9 (4.1/3.7) | 2 (2.1/1.8) |

Example 7: Affinity to Fc-Gamma Receptors hFcγ RI/CD64 and hFcγ RIIIA/CD16a

To measure the binding affinities of polypeptide fusions with an engineered, IgG4-based backbone (SEQ ID NOs: 9 and 10, SEQ ID NOs: 11 and 12, SEQ ID NOs: 13 and 14, and SEQ ID NOs: 15 and 16) to Fc-gamma receptors hFcγ RI/CD64 (R&D Systems) and hFcγ RIIIA/CD16a (R&D Systems), a Surface Plasmon Resonance (SPR) based assay was employed. SEQ ID NOs: 3 and 4 served as a control of a monospecific antibody with an IgG1 backbone. SEQ ID NOs: 5 and 6 served as a control of a polypeptide fusion that was IgG1-based. In the SPR affinity assay, polypeptide fusions were biotinylated and captured on a sensor chip CAP using the Biotin CAPture Kit (GE Healthcare). The sensor Chip CAP was pre-immobilized with an ssDNA oligo. Undiluted Biotin CAPture Reagent (streptavidin conjugated with the complementary ss-DNA oligo) was applied at a flow rate of 2 µL/min for 300 s. Subsequently, 10 µg/mL of biotinylated polypeptide fusion was applied for 300 s at a flow rate of 5 µL/min. SEQ ID NOs: 3 and 4 and the polypeptide fusions were biotinylated by incubation with EZ-Link® NHS-PEG4-Biotin (Thermo Scientific) for two hours at room temperature. The excess of non-reacted biotin reagent was removed by loading the reaction mixture onto a Zeba™ Spin Desalting Plate (Thermo Scientific). The reference channel was loaded with Biotin CAPture Reagent only.

To determine the affinity, three dilutions of hFcγ RI/CD64 (at 40, 8 and 1.6 or at 100, 25 and 6 nM) or four to five dilutions of hFcγ RIIIA/CD16a (at 200, 40, 8 and 1.6 nM or at 1000, 333, 111, 37 and 12 nM) were prepared in running buffer (10 mM HEPES, 150 mM NaCl, 0.05% v/v Surfactant P20, 3 mM EDTA, pH 7.4 (GE Healthcare)) and applied to the chip surface. Applying a flow rate of 30 µL/min, the sample contact time was 180 s and dissociation time was 1800/2700 s for hFcγ RI/CD64 or 300 s hFcγ RIIIA/CD16a. All measurements were performed at 25° C. Regeneration of the Sensor Chip CAP surface was achieved with an injection of 6 M Gua-HCl with 0.25 M NaOH followed by an extra wash with running buffer and a stabilization period of 120 s. Prior to the protein measurements three regeneration cycles were performed for conditioning purposes. Data were evaluated with Biacore T200 Evaluation software (V 2.0). Double referencing was used. For hFcγ RI/CD64 the 1:1 binding model was used to fit the raw data. For hFcγ RIIIA/CD16a the Steady State Affinity model was used to fit the raw data.

Table 5 shows the results of the fit of the data for hFcγ RI/CD64. The IgG1-based test articles SEQ ID NOs: 3 and 4 and SEQ ID NOs: 5 and 6 were both at 0.3 nM, demonstrating that hFcγ RI/CD64 binding was not affected by fusion of SEQ ID NOs: 3 and 4 to an Anticalin protein. The polypeptide fusions SEQ ID NOs: 9 and 10, SEQ ID NOs: 11 and 12, SEQ ID NOs: 13 and 14, and SEQ ID NOs: 15 and 16 showed no detectable binding to hFcγ RI/CD64. These data demonstrate that binding to hFcγ RI/CD64 can be reduced below detection limit by switching the isotype from IgG1 to engineered IgG4.

TABLE 5

| Clone name | KD [nM] |
|---|---|
| SEQ ID NOs: 3 and 4 | 0.3 |
| SEQ ID NOs: 5 and 6 | 0.3 |
| SEQ ID NOs: 9 and 10 | not determinable |
| SEQ ID NOs: 11 and 12 | not determinable |
| SEQ ID NOs: 13 and 14 | not determinable |
| SEQ ID NOs: 15 and 16 | not determinable |

Table 6 shows the results of the fit of the data for hFcγ RIIIA/CD16a. The resulting binding affinities to hFcγ RIIIA/CD16a of the IgG1-based test articles SEQ ID NOs: 3 and 4 and SEQ ID NOs: 5 and 6 were comparable to each other and around 350 nM whereas the polypeptide fusions SEQ ID NOs: 9 and 10, SEQ ID NOs: 11 and 12, SEQ ID NOs: 13 and 14, and SEQ ID NOs: 15 and 16 showed no detectable binding to hFcγ RIIIA/CD16a. These data demonstrate that binding to hFcγ RIIIA/CD16a can be reduced below detection limit by switching the isotype from IgG1 to engineered IgG4.

TABLE 6

| Name | KD [nM] |
|---|---|
| SEQ ID NOs: 3 and 4 | 335 ± 64 |
| SEQ ID NOs: 5 and 6 | 369 ± 76 |
| SEQ ID NOs: 9 and 10 | not determinable |
| SEQ ID NOs: 11 and 12 | not determinable |
| SEQ ID NOs: 13 and 14 | not determinable |
| SEQ ID NOs: 15 and 16 | not determinable |

Example 8: Affinity to Neonatal Fc Receptor

To measure the binding affinities of polypeptide fusions with an engineered, IgG4-based backbone (SEQ ID NOs: 9 and 10, SEQ ID NOs: 11 and 12, SEQ ID NOs: 13 and 14, and SEQ ID NOs: 15 and 16) to the neonatal Fc receptor (FcRn, Sino Biologicals, #CT009-H08H), a Surface Plasmon Resonance (SPR) based assay was employed. SEQ ID NOs: 3 and 4 served as a control of a monospecific antibody with an IgG1 backbone. SEQ ID NOs: 5 and 6 served as a control of a polypeptide fusion that was IgG1-based. In the SPR affinity assay, FcRn was covalently immobilized on a CM5 sensor chip (GE Healthcare) according to the manufacturer's instructions. Briefly, after activating the carboxyl groups of the dextran matrix with 1-ethyl-3-(3-dimethylaminopropyl)-carbodiimide (EDC) and N-hydroxysuccinimide (NHS), the primary amines of the FcRn protein were allowed to react with the NHS ester on the surface until a signal of ~200 RU was reached. Finally, non-reacted NHS-esters were blocked by passing a solution of 1M ethanolamine across the surface. The flow rate throughout the immobilization procedure was 10 µl/min.

To determine their affinity, six dilutions (1000 nM, 333 nM, 111 nM, 37 nM, 12 nM and 4 nM) of all constructs were prepared in running buffer (10 mM HEPES, 150 mM NaCl, 0.05% v/v Surfactant P20, 3 mM EDTA, pH 6.0) and applied to the chip surface. Applying a flow rate of 30 µL/min, the sample contact time was 180 s and dissociation time was 30 s. All measurements were performed at 25° C. Regeneration of the Sensor Chip CAP surface was achieved with an injection of 10 mM glycine pH 3.0. Prior to the protein measurements three regeneration cycles are performed for conditioning purposes. Data were evaluated with Biacore T200 Evaluation software (V 2.0) with double referencing. The Steady State Affinity model was used to fit the raw data.

The resulting binding affinities of all polypeptide fusions to FcRn were in the range of 1-2 µM which demonstrates that switching the isotype from IgG1 to IgG4 has no detectable impact on FcRn binding.

TABLE 7

| Name | KD [µM] |
|---|---|
| SEQ ID Nos: 3 and 4 | 2.0 ± 0.2 |
| SEQ ID Nos: 5 and 6 | 1.1 ± 0.03 |
| SEQ ID Nos: 11 and 12 | 1.3 ± 0.07 |
| SEQ ID Nos: 13 and 14 | 1.8 ± 0.04 |

TABLE 7-continued

| Name | KD [µM] |
|---|---|
| SEQ ID Nos: 9 and 10 | 1.7 ± 0.05 |
| SEQ ID Nos: 13 and 14 | 1.8 ± 0.01 |

Example 9: Functional T-Cell Activation Assay Using Tumor Cells with High and Low HER2 Levels We employed a target-cell dependent T-cell activation assay to assess the ability of the fusion polypeptide of SEQ ID NOs: 9 and 10 to co-stimulate T-cell responses as a function of HER2 expression levels of the target cell. For that purpose, we employed HER2-high expressing SKBR3 and BT474 cells, as well as cells expressing HER2 at a level similar to healthy, HER2-expressing cells, HepG2 and MCF7. For comparison, we investigated the behavior of reference anti-CD137 monoclonal antibodies of SEQ ID NOs: 47 and 48 and SEQ ID NOs: 49 and 50. As a negative control, we employed the monospecific, HER2-binding antibody of SEQ ID NOs: 3 and 4. As a further negative control, the experiment was carried out without the addition of a test article ("vehicle control"). In the experiment, an anti-human CD3 antibody (OKT3, eBioscience) was coated on plastic culture dishes, and subsequently SKBR3, BT474, HepG2 or MCF7 cells were separately cultured on the dishes overnight. The next day, purified T cells were incubated on the coated surface in the presence of various concentrations of the fusion polypeptide of SEQ ID NOs: 9 and 10, reference antibodies SEQ ID NOs: 47 and 48 and SEQ ID NOs: 49 and 50, the control antibody of SEQ ID NOs: 3 and 4, or in the absence of added test article. As readout, we measured supernatant interleukin 2 (IL-2) levels. In the following, the experiment is described in detail.

Human peripheral blood mononuclear cells (PBMC) from healthy volunteer donors were isolated from buffy coats by centrifugation through a Polysucrose density gradient (Biocoll 1.077 g/mL from Biochrom), following Biochrom's protocols. The T lymphocytes were isolated from the resulting PBMC using a Pan T cell purification Kit (Miltenyi Biotec GmbH) and the manufacturer's protocols. Purified T cells were re-suspended in a buffer consisting of 90% FCS and 10% DMSO, immediately frozen down using liquid nitrogen and stored in liquid nitrogen until further use. For the assay, T cells were thawed for 16 h and cultivated in culture media (RPMI 1640, Life Technologies) supplemented with 10% FCS and 1% Penicillin-Streptomycin (Life Technologies).

The following procedure was performed using triplicates for each experimental condition. Flat-bottom tissue culture plates were pre-coated or not for 1 h at 37° C. using 200 µL of 0.25 µg/mL anti-CD3 antibody. The plates were subsequently washed twice with PBS. $5 \times 10^4$ target tumor cells per well were plated and allowed to adhere overnight at 37° C. in a humidified 5% $CO_2$ atmosphere. The target cells had before been grown in culture under standard conditions, detached using Accutase and re-suspended in culture media. On the next days, tumor cells were treated for 2 hours at 37° C. with mitomycin C (Sigma Aldrich) at a concentration of 30 µg/ml in order to block their proliferation. Plates were washed twice with PBS, and 100 µL of the T-cell suspension (corresponding to $5 \times 10^4$ T cells) and SEQ ID NOs: 9 and 10, reference antibodies SEQ ID NOs: 47 and 48 and SEQ ID NOs: 49 and 50 or the negative control SEQ ID NOs: 3 and 4 or vehicle, at concentrations ranging from 0.05 nM to 5 nM (with the exception of BT474, were concentrations ranged from 0.1 µM to 50 nM), were added to each well. Plates were covered with a gas permeable seal (4titude) and incubated at 37° C. in a humidified 5% $CO_2$ atmosphere for 3 days. Subsequently, the IL-2 concentration in the supernatant was assessed as described below.

Human IL-2 levels in the cell culture supernatants were quantified using the IL-2 DuoSet kit from R&D Systems. In the first step, a 384 well plate was coated at room temperature for 2 h with 1 µg/mL "Human IL-2 Capture Antibody" (R&D System) diluted in PBS. Subsequently, wells were washed 5 times with 80 µl PBS-T (PBS containing 0.05% Tween20) using a Biotek EL405 select CW washer (Biotek). After 1 h blocking in PBS-T additionally containing 1% casein (w/w), pooled supernatant and a concentration series of an IL-2 standard diluted in culture medium were incubated in the 384-well plate overnight at 4° C. To allow for detection and quantitation of captured IL-2, a mixture of 100 ng/mL biotinylated goat anti-hIL-2-Bio detection antibody (R&D System) and 1 µg/mL Sulfotag-labelled streptavidin (Mesoscale Discovery) were added in PBS-T containing 0.5% casein and incubated at room temperature for 1 h. After washing, 25 µL reading buffer was added to each well and the electrochemiluminescence (ECL) signal of every well was read using a Mesoscale Discovery reader. Analysis and quantification were performed using Mesoscale Discovery software.

The result of a representative experiment is depicted in FIG. 11. In this Figure, values are plotted relative to the background IL-2 production in the absence of test article, and therefore represent the fold change compared to background. While the negative control of SEQ ID NOs: 3 and 4 (FIG. 11A) does not lead to IL-2 induction on T-cells with any of the four cell lines, rising concentrations of the bispecific fusion polypeptide SEQ ID NOs: 9 and 10 (FIG. 11A) induce T-cells to produce IL-2 in the presence of the highly HER2-expressing SKBR3 and BT474 cells. However, no IL-2 increase due to SEQ ID NOs: 9 and 10 is apparent for HepG2 and MCF7 cells. This behavior is markedly different from both the first anti-CD137 antibody SEQ ID NOs: 47 and 48, which induces IL-2 on T-cells in the presence of all four cell lines (FIG. 11B), and the second anti-CD137 antibody SEQ ID NOs: 49 and 50, which does not lead to induction of IL-2 on any of the four cell lines (FIG. 11C).

The experiment demonstrates that the fusion protein defined by SEQ ID NOs: 9 and 10 activates T-cells in a manner that is dependent on the HER2 density of the target cells. While the highly HER2-expressing SKBR3 and BT474 cells show a clear T-cell activation as measured by IL-2 production, this effect does not occur with HepG2 and MCF7 cells, which express HER2 at a considerably lower level. That this effect is attributable to the HER2 density and not to a potential inhibition or lack of costimulation brought about by the cell under study which renders CD137 signaling ineffective becomes apparent by the fact that the anti-CD137 antibody SEQ ID NOs: 47 and 48 is capable of activating T cells via CD137 signaling with all four cell types.

Example 10: 4-Week Stability Study of Fusion Polypeptides in Buffer at Neutral pH and Elevated Temperature To investigate the stability of fusion polypeptide defined by SEQ ID NOs: 9 and 10, SEQ ID NOs: 11 and 12, SEQ ID NOs: 13 and 14 and SEQ ID NOs: 15 and 16, we employed an experiment where samples where incubated for 4 weeks at 40° C. in PBS, pH7.4 at a concentration of approximately 20 mg/mL (range 21-23 mg/mL). For comparison, we investigated the behavior of the polypeptide defined by SEQ ID NOs: 3 and 4 under identical conditions. Samples were concentrated from a concentration of around 5 mg/mL to around 20 mg/mL using centrifugal filters (Ultracef-3K, Amicon), and a part of this concentrated sample was stored at −20° C. as reference material. 0.1 mL of the concentrated sample in 0.5 mL tubes (PCR-PT, Sarstedt) were then stored in an incubator (Memmert) for 4 weeks at 40° C. To investigate the integrity and monomeric content of the sample, it was then subjected to analytical size exclusion chromatography (SEC) using a Superdex200 Increase column on an Agilent 1200 Series GPC2 System at a flow rate of 0.150 mL/min. 20 µg of sample were applied to the column. Relative protein concentration in the continuous flow-through was detected by absorption at a wavelength of 280 nm.

FIG. 12 provides the results of the SEC analysis for all fusion polypeptides and the control SEQ ID NOs: 3 and 4 as indicated. The respective bottom and top SEC traces for each fusion polypeptide correspond to the reference material and the material incubated for 4 weeks at 40° C., respectively. Comparing reference material and incubated material reveals that the SEC trace does not change significantly for either the bispecific fusion polypeptides or the control SEQ ID NOs: 3 and 4, demonstrating the stability of the fusion polypeptides against aggregation.

Example 11: Pharmacokinetics of Fusion Polypeptides in Mice

An analysis of the pharmacokinetics of fusion polypeptides defined by SEQ ID NOs: 9 and 10, SEQ ID NOs: 11 and 12, SEQ ID NOs: 13 and 14 and SEQ ID NOs: 15 and 16, as well as of SEQ ID NOs: 3 and 4 for reference, was performed in mice. Male CD-1 mice approximately 5 weeks of age (3 mice per timepoint; Charles River Laboratories, Research Models and Services, Germany GmbH) were injected into a tail vein with a fusion polypeptide at a dose of 10 mg/kg. The test articles were administered as a bolus using a volume of 5 mL/kg. Plasma samples from the mice were obtained at the timepoints of 5 min, 1 h, 2 h, 4 h, 8 h, 24 h, 48 h, 4 d, 8 d, 14 d and 20 d. Sufficient whole blood—taken under isoflurane anaesthesia—was collected to obtain at least 100 µL Li-Heparin plasma per animal and time. Drug levels were detected using a Sandwich ELISA detecting the full bispecific construct via the targets HER2 and CD137. Trastuzumab plasma levels were determined using a Sandwich ELISA with targets HER2 and human Fc. The data were fitted using a two-compartmental model using Prism GraphPad 5 software.

FIG. 13 shows plots of the plasma concentration over time for the constructs SEQ ID NOs: 9 and 10, SEQ ID NOs: 11 and 12, SEQ ID NOs: 13 and 14 and SEQ ID NOs: 15 and 16, in all cases plotted together with the values obtained for SEQ ID NOs: 3 and 4 for reference. The pharmacokinetics looked similar in all cases. Starting from a plasma concentration of around 200 µg/mL, plasma levels fell to a level of around 50 µg/mL within 48 hours, and then further decrease at a much slower rate to a level of around 25 µg/mL at the end of the experiment after 20 days. The bi-exponential decay of a two-compartmental model was successfully applied to accurately describe the data, and a fit of the data (FIG. 13, Table 8) using this model resulted in terminal half-lives of 15-21 days for the bispecific fusion polypeptides, compared to 13 days for SEQ ID NOs: 3 and 4.

The data demonstrate that the bispecific fusions have long, antibody-like terminal half-lives in mice. Because the assay employed to determine fusion polypeptide plasma concentrations requires a retained activity both towards HER2 and CD137, the result also demonstrates that the bispecific molecules remain intact and active over the time course of 20 days.

TABLE 8

Terminal half-lives in mice obtained using a data fit based on a two-compartmental model

| Construct | Terminal half-life [days ± std error of fit] |
|---|---|
| SEQ ID NOs: 3 and 4 | 13.3 ± 1.2 |
| SEQ ID NOs: 9 and 10 | 20.9 ± 3.8 |
| SEQ ID NOs: 11 and 12 | 19.1 ± 2.5 |
| SEQ ID NOs: 13 and 14 | 14.8 ± 1.5 |
| SEQ ID NOs: 15 and 16 | 15.6 ± 1.9 |

Example 12: Pharmacokinetics of Fusion Polypeptides in Cynomolgus Monkey

An analysis of the pharmacokinetics of fusion polypeptides defined by SEQ ID NOs: 9 and 10, SEQ ID NOs: 11 and 12, SEQ ID NOs: 13 and 14 and SEQ ID NOs: 15 and 16, as well as of SEQ ID NOs: 3 and 4 for reference, was performed in cynomolgus monkeys. Male cynomolgus monkeys received an intravenous infusion over 60 minutes, with a dose of 3 mg/kg test article. Plasma samples from the cynomolgus monkeys were obtained at the timepoints of 15 min, 2 h, 4 h, 8 h, 24 h, 48 h, 3 d, 4 d, 5 d, 6 d, 7 d, 9 d, 11 d, 14 d, 18 d, and 24 d. Drug levels were detected using a Sandwich ELISA detecting the full bispecific construct via the targets HER2 and CD137. Trastuzumab plasma levels were determined using a Sandwich ELISA with targets HER2 and human Fc. The data were fitted using a two-compartmental model using Prism GraphPad 5 software.

FIG. 14 shows semi-logarithmic plots of the plasma concentration over time for the constructs SEQ ID NOs: 9 and 10, SEQ ID NOs: 11 and 12, SEQ ID NOs: 13 and 14 and SEQ ID NOs: 15 and 16, in all cases plotted together with the values obtained for SEQ ID NOs: 3 and 4 for reference. The pharmacokinetics looked similar in all cases. Starting from a plasma concentration of around 70 µg/mL, plasma levels fall to levels close to zero over the timecourse of 24 days. The bi-exponential decay of a two-compartmental model was successfully applied to accurately describe the data, and a fit of the data (FIG. 14, Table 9) using this model resulted in terminal half-lives of ranging from approximately 64 to 99 hours for the bispecific fusion polypeptides, compared to eighty-six hours for SEQ ID NOs: 3 and 4.

The data therefore demonstrate that the bispecific fusions have terminal half-lives in cynomolgus monkeys that are very similar to the half-life of the reference polypeptide SEQ ID NOs: 3 and 4.

TABLE 9

Terminal half-lives in male cynomolgus monkeys obtained using a data fit based on a two-compartmental model:

| Construct | Terminal half-life [hours ± std error of fit] |
|---|---|
| SEQ ID NOs: 3 and 4 | 86.0 ± 3.1 |
| SEQ ID NOs: 9 and 10 | 98.7 ± 1.5 |

TABLE 9-continued

Terminal half-lives in male cynomolgus monkeys obtained using a data fit based on a two-compartmental model:

| Construct | Terminal half-life [hours ± std error of fit] |
|---|---|
| SEQ ID NOs: 11 and 12 | 65.2 ± 1.4 |
| SEQ ID NOs: 13 and 14 | 83.9 ± 3.0 |
| SEQ ID NOs: 15 and 16 | 63.7 ± 0.7 |

Example 13: Ex Vivo T Cell Immunogenicity Assessment of Fusion Polypeptides

To investigate the risk of the formation of anti-drug antibodies in man, an in vitro T cell immunogenicity assessment of the bispecific fusion polypeptides SEQ ID NOs: 9 and 10, SEQ ID NOs: 11 and 12, SEQ ID NOs: 13 and 14 and SEQ ID NOs: 15 and 16, as well as of SEQ ID NOs: 3 and 4 for reference, the control antibody of SEQ ID NOs: 3 and 4 and the positive control keyhole limpet hemocyanine (KLH) was performed. To perform the experiment, PBMC from 32 donors selected to cover HLA allotypes reflective of the distribution in a global population were thawed, washed and seeded onto 96-well plates at a density of $3\times10^5$ cells per well. Test articles, diluted in assay media, were added to the cells at a concentration of 30 μg/mL. Assay medium alone was used as a blank, and keyhole limpet hemocyanine (KLH) was used as a nave positive control. PBMC were incubated for 7 days in a humidified atmosphere at 37° C. and 5% $CO_2$. On day 7, PBMCs were labelled for surface phenotypic CD3+ and CD4+ markers and for DNA-incorporated EdU (5-ethynyl-2'deoxyuridine), used as a cell proliferation marker. The percentage of $CD3^+CD4^+EdU^+$ proliferating cells was measured using a Guava easyCyte 8HT flow cytometer and analysed using GuavaSoft InCyte software.

FIG. 15 provides the results of this assay for all 32 donors and all test molecules under study. In FIG. 15A, the stimulation index was plotted, which was obtained by the ratio of proliferation in the presence vs. absence of test article. The threshold that defines a responding donor (stimulation index>2) is indicated as a dotted line. In FIG. 15B, the number of responding donors as defined by this threshold was plotted. Evidently, the number of donors responding to the reference SEQ ID NOs: 3 and 4 lies at one and is therefore small, while all 32 donors respond to the positive control KLH with strong proliferation above the threshold. For the bispecific fusion polypeptides, the number of responding donors ranges from zero (SEQ ID NOs: 9 and 10) via one (SEQ ID NOs: 15 and 16) and two (SEQ ID NOs: 13 and 14) to three (SEQ ID NOs: 11 and 12).

The experiment therefore demonstrates that the bispecific fusion polypeptides, in particular SEQ ID NOs: 9 and 10 and SEQ ID NOs: 15 and 16, induce little reponse in the in vitro T cell immunogenicity assessment, which indicates that the risk of inducing immunogenic responses is low.

Example 14: Tumor Growth Inhibition by CD137/HER2 Bispecifics in Humanized Mouse Tumor Model In order to investigate the activity of SEQ ID NOs: 9 and 10, SEQ ID NOs: 11 and 12, SEQ ID NOs: 13 and 14 and SEQ ID NOs: 32 and 33 in an in-vivo mouse model, we employed immune deficient NOG mice (Taconic, NOD/Shi-scid/IL-2Rynull) engrafted with human SK-OV-3 tumors and human PBMC. 4-6 week old NSG mice were subcutaneously (s.c.) injected with $5\times10^6$ SK-OV-3 cells in a matrigel/PBS (1:1) solution. Tumors were allowed to grow to an average of 120 $mm^3$ and on day 0 of the experiment mice were randomized into treatment groups according to tumor size and animal weight. Mice were given $7\times10^6$ fresh human PBMC intravenously (i.v.) into a tail vein. Mice received 20 μg or 100 μg of treatment or control into the intraperitoneal cavity 1 hour after PBMC injection on day 0, and again on day 7 and day 14. The molecules under study were IgG4 isotype control (Cat# DDXCHO4P, Acris Antibodies GmbH), HER2/CD137 bispecifics SEQ ID NOs: 9 and 10 (100 μg or 20 μg), SEQ ID NOs: 11 and 12 (100 μg or 20 μg) and SEQ ID NOs: 13 and 14 (100 μg), or the CD137-binding benchmark antibody of SEQ ID NOs: 32 and 33 (100 μg). Each group contained 10 mice with the exception of the group studying SEQ ID NOs: 32 and 33 which consisted of 7 mice. Tumor growth was recorded every 3-4 days.

Figure 16:
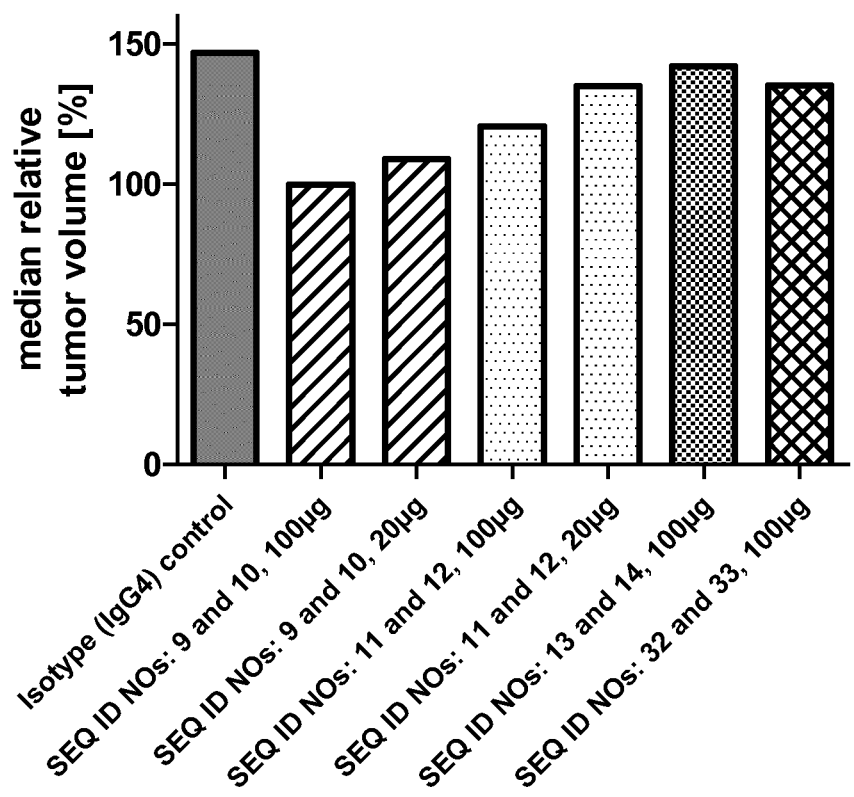

FIG. 16 shows the median tumor sizes relative to the starting volume at day 14 of the study. The best responses, ordered by strength of tumor growth inhibition, were achieved by SEQ ID NOs: 9 and 10 (100 μg), SEQ ID NOs: 9 and 10 (20 μg) and SEQ ID NOs: 11 and 12 (100 μg), while SEQ ID NOs: 11 and 12 at the lower dose of 20 μg, SEQ ID NOs: 13 and 14 (100 μg) as well as the CD137-binding benchmark antibody of SEQ ID NOs: 32 and 33 has a median response that was similar to that of the isotype control.

Example 15: Investigating CD137 Pathway Activation Using NF-κB-luc2P/4-1BB Jurkat Reporter Cells We employed a target-cell based reporter assay to assess the ability of the fusion polypeptide of SEQ ID NOs: 9 and 10 capable of binding CD137 and HER2 at the same time—to activate the CD137 pathway in dependence of the HER2 status of the target cell. For that purpose, we employed highly HER2-expressing NCI-N87 gastric cancer cells that were mixed with NF-κB-luc2P/4-1BB Jurkat cells (Promega, CS196002) engineered to overexpress CD137 and carrying a NF-κB Luciferase reporter gene. For comparison, we investigated the behavior of reference anti-CD137 monoclonal antibodies of SEQ ID NOs: 32 and 33 and SEQ ID NOs: 34 and 35. As a negative control, we employed the monospecific, HER2-binding antibody of SEQ ID NOs: 3 and 4. As further control, we also assessed the CD137 pathway activation in the absence of NCI-N87 cells for the fusion polypeptide of SEQ ID NOs: 9 and 10 and for anti-CD137 monoclonal antibodies of SEQ ID NOs: 32 and 33 and SEQ ID NOs: 34 and 35 as well as for the monospecific, HER2-binding antibody of SEQ ID NOs: 3 and 4. Finally, the experiment was also carried out without the addition of a test article ("vehicle control"). The background signal measured in the presence of NCI-N87 cells alone was assessed in wells where no NF-κB-luc2P/4-1BB Jurkat cells had been added. In the experiment, NCI-N87 cells were cultured on the dishes overnight. The next day, freshly thawed out NF-κB-luc2P/4-1BB Jurkat cells (Promega, CS196002) were incubated for six hours on the coated surface in the presence of various concentrations of the fusion polypeptide of SEQ ID NOs: 9 and 10, the reference antibodies SEQ ID NOs: 32 and 33 and SEQ ID NOs: 34 and 35, the control antibody of SEQ ID NOs: 3 and 4, or in the absence of added test article. As readout, we measured the luminescence induced by the addition of Bio-Glo™ buffer (Promega, G7940) on the Jurkat reporter cells. In the following, the experiment is described in detail.

The following procedure was performed using triplicates for each experimental condition. Flat-bottom tissue culture plates were used to coat $5 \times 10^4$ target NCI-N87 tumor cells per well, with some wells remaining without target cancer cells as control wells. The cells were allowed to adhere overnight at 37° C. in a humidified 5% $CO_2$ atmosphere. The target cells had before been grown in culture under standard conditions, detached using Accutase and resuspended in culture media.

On the next day, plates were washed twice with PBS, and 50 μL of the NF-κB-luc2P/4-1BB Jurkat cells suspension (corresponding to $1.5 \times 10^5$ cells) and 25 μL of SEQ ID NOs: 9 and 10 at concentrations ranging from 0.04 nM to 10 nM, reference antibodies SEQ ID NOs: 32 and 33 and SEQ ID NOs: 34 and 35 at concentrations ranging from 0.4 nM to 10 nM, the negative control SEQ ID NOs: 3 and 4 at a concentration of 10 nM, or vehicle were added to each well. Plates were covered with a gas permeable seal (4titude) and incubated at 37° C. in a humidified 5% $CO_2$ atmosphere for 6 hours. Subsequently, 75 μL of Bio-Glo™ buffer (Promega, G7940) was added to each well containing cells (1:1 v/v) and luminescence was measured using a luminescence plate reader (Pherastar). Analysis, quantification and curve fitting were performed using Graphpad Prism software.

The result of a representative experiment is depicted in FIG. 17. In this Figure, plotted values are provided in relative luminescence units (RLU). Rising concentrations of the bispecific fusion polypeptide SEQ ID NOs: 9 and 10 (FIG. 17A) induce CD137 pathway activation in reporter Jurkat cells in the presence of the highly HER2-expressing NCI-N87 cells, in contrast to the negative control of SEQ ID NOs: 3 and 4 (FIG. 16A). Furthermore, no increase luminescence is observed when the target NCI-N87 cells are missing. This behavior is markedly different to both the first anti-CD137 antibody SEQ ID NOs: 32 and 33, which induces CD137 pathway activation in the Jurkat reporter cells both in the presence and absence of NCI-N87 cells (FIG. 17B), and the second anti-CD137 antibody SEQ ID NOs: 34 and 35, which does not lead to CD137 pathway activation in the Jurkat reporter cells at all (FIG. 17C).

The experiment demonstrates that SEQ ID NOs: 9 and 10 activates the CD137 pathway in a manner that depends upon the presence of target cells expressing HER2, as no activation occurred in the absence of NCI-N87 cells. These data validate that the mode of action of SEQ ID NOs: 9 and 10 in T cell activation is the activation of the CD137 pathway by crosslinking the CD137 receptor via engagement of HER2 on cancer cells. The HER2-positive cell-specific mode of action is further highlighted by comparison to the data of the anti-CD137 antibody SEQ ID NOs: 32 and 33, which activates T cells via CD137 signaling whether target cells are present or not.

Example 16: Tumor Growth Inhibition by CD137/HER2 Bispecifics in Humanized Mouse Tumor Model In a protocol similar to Example 14, immuno-compromised mice engrafted with HER2-positive tumor cells (SKOV-3) were injected with human PBMC and treated over 3 weeks with SEQ ID NOs: 9 and 10 at a 100 μg/week or 20 μg/week, anti-CD137 antibody SEQ ID NOs: 32 and 33, or controls, which were vehicle with PBMC ("PBMC only"), vehicle without PBMC ("no PBMC") or isotype control with PBMC. Specifically, NOG mice were subcutaneously (s.c.) injected with SK-OV-3 cells and tumors were allowed to grow to an average of 120 $mm^3$ prior to randomization into treatment groups. There were 10 animals per treatment group. Mice were engrafted with fresh human PBMC intravenously (i.v.) into a tail vein and treatment commenced 1 hour later. Mice received 3 weekly intraperitoneal (i.p.) doses of treatment (20 μg or 100 μg) of SEQ ID NOs: 9 and 10 or SEQ ID NOs: 32 and 33 or control. Tumor growth was recorded twice weekly. Tumors from two mice were harvested on day 20 post treatment and assessed for infiltration of human T cells by immunohistochemistry via staining for the human lymphocyte marker CD45.

The results of the experiement are reported in FIG. 18. FIG. 18A shows median tumor growth over time. Data points that no longer represent the full group size of 10 mice are connected by dotted lines. The best responses, ordered by strength of tumor growth inhibition, were achieved by SEQ ID NOs: 9 and 10 (100 μg), followed by the lower dose (20 μg) of the same antibody, while the CD137-binding benchmark antibody of SEQ ID NOs: 32 and 33 has a median response that was similar to that of the isotype control. FIG. 18B shows Immunohistochemistry of tumors after study end. Sections of formalin-fixed and paraffin-embedded tumors (2 per group) were stained for the human lymphocyte marker CD45; the frequency of CD45-positive cells was quantified by dedicated software as reflected in FIG. 18B. The figure shows that SEQ ID NOs: 9 and 10 (100 μg) resulted in increased frequency of human tumor infiltrating lymphocytes (TILs) while SEQ ID NOs: 9 and 10 (20 μg) and controls did not.

The results reflect that SEQ ID NOs: 9 and 10 treatment at high dose (100 μg/wk) and low dose (20 μg/wk) resulted in stronger tumor growth inhibition (TGI) compared to isotype control or anti-CD137 benchmark. IHC staining for the human lymphocyte marker CD45 shows increased frequency of human TIL for high dose (100 μg) SEQ ID NOs: 9 and 10 while low dose (20 μg) SEQ ID NOs: 9 and 10 does not show this effect. Taken together these data are consistent with a dual functionality of SEQ ID NOs: 9 and 10: On the one hand, the tumor-localized targeting of CD137 leads to expansion of TIL's in the tumor microenvironment and suggests tumor-localized costimulatory T cell activation by SEQ ID NOs: 9 and 10 while tumor growth inhibition is observed with 20 ug SEQ ID NOs: 9 and 10 in the absence of TIL expansion, suggesting this activity may be driven by HER2 antagonism.

Example 17: PBMC Phenotyping and Mortality in Humanized NOG Mouse SKOV-3 Tumor Model In order to assess the safety of SEQ ID Nos: 9 and 10, PBMCs were isolated from mouse blood samples of the mice of Experiment 16. These samples were taken on day 19 after PBMC engraftment and analysed by multicolor FACS for human surface markers CD45, CD3 and CD8. Peripheral blood was resuspended in 10 ml 1× erythrocyte lysis buffer (0.15M $NH_4Cl$, 10 mM $KHCO_3$, 0.1 mM EDTA) and lysed for 1-3 minutes at room temperature in a 15-ml tube. Cells were centrifuged at 300×g for 10 minutes at 4° C., washed 1× with 10 ml FC-buffer (2% fetal calf serum in PBS, pH7.4) and resuspended in 200 μl of FC-buffer. Cells were transferred to a 96-well plate at a density of $5 \times 10^5$ cells/well. Cells were pelleted by centrifugation of the plates at 400×g for 3 minutes at 4° C. and the supernatant was removed. Fc-block antibody (10 μl/well of a 1:100 dilution in buffer of 2.4G2 antibody, 0.5 mg/ml, #553142 BD Bioscience) was added to each well and plates were incubated for 15 minutes at room temperature. Then specific antibodies against human targets hCD45 (Life Technologies), hCD3 and hCD8 (both BD Bioscience) were added (0.5-1 µg/sample) and plates were incubated at 4° C. for 30 minutes protected from light. Following another washing step (centrifugation of the plates at 400×g for 3 min. at 4° C.), cells were resuspended in 200 µl FC Buffer for analysis with an Attune Focusing Cytometer (blue (488 nm)/violet (405 nm) laser configuration). Flow cytometry data were analyzed with the FlowJo Data Analysis Software.

FIG. 19A shows the CD45, CD3 and CD8 phenotype of PMBCs from the treatement and control groups of Example 16 taken on day 19 of that study. FIG. 19A on the left shows the percentage of total PMBCs expressing CD45 while the FIG. 19A on the right shows the fraction of CD3+CD8+T effector cells in the CD45-positive cell population. Clearly, the results demonstrate that the anti-CD137 antibody SEQ ID NOs: 32 and 33 treatment leads to stronger expansion of human lymphocytes in the mouse peripheral blood compared to the control group or SEQ ID NOs: 9 and 10, and that this expansion correlates with a strong increase in the CD8+ human effector T cells. FIG. 19B shows the mortality of treatment and control groups of Experiment 16. Plotted values of FIG. 19B correspond to number of mice per group of ten that died spontaneously or needed to be sacrificed based on defined general condition criteria. The results reflect that Anti-CD137 mAb treatment led to accelerated graft-versus-host disease with significant mortality compared to control and SEQ ID NOs: 9 and 10 by the end of the study. Combined with the PBMC phenotyping data, the results indicate that the accelerated xenograft versus host disease (xGvHD) induced by anti-CD137 mAb treatment is caused by strongly increased expansion of CD8+ human effector T cells in anti-CD137 group compared to the control or SEQ ID NOs: 9 and 10 groups.

Example 18: Tumor Growth Inhibition by CD137/HER2 Bispecifics in Humanized Mouse Tumor Model In order to investigate the activity of SEQ ID NOs: 9 and 10 in an in-vivo mouse model, we employed immune deficient NOG mice (Taconic, NOD/Shi-scid/IL-2Rynull) engrafted with human SK-OV-3 tumors and human PBMC. The monospecific CD137-targeting antibody SEQ ID NOs: 32 and 33 and the monospecific HER2-targeting construct (IgG4 backbone) SEQ ID Nos: 51 and 52 were investigated in paralell to assess the effect of monospecific vs. bispecific targeting of the receptors HER2 and CD137.

4-6 week old NSG mice were subcutaneously (s.c.) injected with 5×10$^6$ SK-OV-3 cells in a matrigel/PBS (1:1) solution. Tumors were allowed to grow to an average of 110 mm$^3$ and on day 0 of the experiment mice were randomized into treatment groups according to tumor size and animal weight. Mice were given 7×10$^6$ fresh human PBMC intravenously (i.v.) into a tail vein. Mice received the HER2/CD137 bispecific SEQ ID NOs: 9 and 10 at four different concentrations (200 µg, 100 µg, 20 µg or 4 µg), isotype control (100 µg, Cat# C0004, Crown Bioscience Inc., CA), monospecific CD137-targeting antibody SEQ ID NOs: 32 and 33 (100 µg) and monospecific HER2-targeting antibody SEQ ID Nos: 51 and 52 (80 µg) into the intraperitoneal cavity 1 hour after PBMC injection on day 0, and again on day 7 and day 14. Note that the dose of SEQ ID Nos: 51 and 52 (80 µg) was chosen to be equimolar to that of the 100 µg SEQ ID NOs: 9 and 10 group. As negative controls, groups receiving vehicle and PBMC, or vehicle only ("no PBMC") were also included. Each group contained 10 mice with the exception of the group SEQ ID NOs: 9 and 10, which consisted of 9 mice as one mouse succumbed on day 4 of the study due to treatment-unrelated causes. Tumor growth was recorded every 3-4 days. Statistical significance of tumor growth inhibition responses was determined by a two-sided student's T-test.

FIG. 20 shows the mortality across study groups at day 20 after PBMC engraftment. Mortality caused by PBMC xenograft-vs-host-disease (xGvHD) either led to spontaneous death or to ethical sacrifice based on predefined critera. Strikingly, the monospecific CD137-targeting antibody SEQ ID NOs: 32 and 33 led to strongly accelerated xGvHD compared to all other groups, with no mouse surviving to study end. Most other groups also showed mortality before study end, with up to three mortalities at day 20. There was no apparent dose-dependency for the four treatment groups of SEQ ID NOs: 9 and 10, and mortality was similar to the SEQ ID NOs: 51 and 52 group and the "PBMC only" group, indicating no impact of SEQ ID NOs: 9 and 10 on onset of xGvHD.

FIG. 21 shows the absolute median tumor sizes over time. Note that values are combined by dotted lines for groups that are no longer complete due to mortality (see above). Strikingly, the isotype control group led to significant tumor growth inhibition compared to the vehicle control groups with and without PBMC; in the following discussion, the relevant control group for the treatment groups was therefore chosen to be the isotype control group. Compard to this group, there was strong tumor growth inhibition for SEQ ID NOs: 9 and 10 at the weekly 200 µg and 100 µg dose as well as for SEQ ID Nos: 51 and 52 at the 80 µg dose, with all responses being similar and highly statistically significant (p<0.001). SEQ ID NOs: 9 and 10 at a dose of 20 µg weekly showed a trend towards tumor growth inhibition compared to the isotype control group, but statistical significance was borderline (p=0.07). There was no statistically significant difference at day 20 between the tumor growth of the isotype control group and that of either the CD137-binding benchmark antibody of SEQ ID NOs: 32 and 33 or of the lowest dose of the CD137/HER2 bispecific SEQ ID NOs: 9 and 10 (4 µg). Taken together, the median tumor growth curves indicate a strong dose-dependent anti-tumor activity of SEQ ID NOs: 9 and 10, which, taking the result for SEQ ID NOs: 51 and 52 into account, appear to be mainly driven by the anti-HER2 activity of SEQ ID NOs: 9 and 10.

Example 19: Phenotyping of Tumor-Infiltrating Lymphocytes by Immunohistochemistry in Humanized Mouse Tumor Model In a follow-up analysis of the in-vivo study described in Example 18, tumors from five or six tumor-bearing mice from each of the nine study groups were excised on study end or ethical sacrifice and assessed for infiltration of human T cells by immunohistochemistry via staining for the human lymphocyte marker CD45. For that purpose, tumors were formalin-fixed, embedded in paraffin and processed for immunohistochemistry using anti-human CD45 antibodies. CD45-positive cells were identified by 3,3'-diaminobenzidine (DAB) staining. To allow clear visualization of DAB-positivity in a greyscale image, contrast and brightness of the images was digitally adjusted.

An overview over all stained tumor sections is provided in FIG. 22, while FIG. 23 provides the result of a digital quantitation of the frequency of CD45-positive cells by dedicated software. FIG. 22 illustrates an evident qualitative difference between the SEQ ID NOs: 9 and 10-treated groups at the weekly dosings of 200 µg, 100 µg or 20 µg compared to all other groups: Clearly, the DAB-positivity in the correponding tumor slices is much stronger. The total absence of staining in the "no PBMC" group confirms the selectivity of the staining procedure. The digital quantitation (FIG. 23) confirms this qualitative finding: With the exception of the 4 µg dosing group, the tumors from SEQ ID NOs: 9 and 10-treated animals display a strong hCD45-positivity, indicative of a high frequency of human lymphocytes in the slides. The hCD45-positivity is statistically significantly higher ($p<0.01$) than in the control groups ("PBMC only" or isotype control) or in the groups treated with the HER2-monospecific SEQ ID NOs: 51 and 52 or the CD137-monospecific benchmark antibody SEQ ID NOs: 32 and 33. Notably, the latter group even displays a statistically significant lower human lymphocyte presence than that of the control groups, for example compared to the isotype control ($p=0.02$). However, this effect may be biased by the earlier sampling that took place with the mice from this group due to required ethical sacrifice.

Taken together, this data illustrates the tumor-localized costimulatory mode of action of SEQ ID NOs: 9 and 10, leading to an increased frequency of human lymphocytes in the tumor at weekly doses of 20 µg or higher. Importantly, this activity is strictly driven by the bispecific activity of SEQ ID NOs: 9 and 10, because the monospecific HER2-targeting antibody SEQ ID NOs: 51 and 52 and the monospecific CD137-targeting antibody SEQ ID NOs: 32 and 33 do not display this activity. On the contrary, the monospecific CD137-targeting antibody SEQ ID NOs: 32 and 33 even leads to a decreased frequency of human lymphocytes compared to the negative controls.

Example 20: PBMC Phenotyping in Humanized Mouse Tumor Model

In order to further elucidate the mode of action and assess the safety of SEQ ID Nos: 9 and 10, PBMCs were isolated from mouse blood samples of the mice of Experiment 18. These samples were taken from the final bleeding after sacrifice of the mice at study end or after ethical sacrifice and analysed by multicolor FACS for human surface markers CD45 and CD8. Peripheral blood was resuspended in 10 ml 1× erythrocyte lysis buffer (0.15M $NH_4Cl$, 10 mM $KHCO_3$, 0.1 mM EDTA) and lysed for 1-3 minutes at room temperature in a 15-ml tube. Cells were centrifuged at 300×g for 10 minutes at 4° C., washed 1× with 10 ml FC-buffer (2% fetal calf serum in PBS, pH7.4) and resuspended in 200 µl of FC-buffer. Cells were transferred to a 96-well plate at a density of $5\times10^5$ cells/well. Cells were pelleted by centrifugation of the plates at 400×g for 3 minutes at 4° C. and the supernatant was removed. Fc-block antibody (10 µl/well of a 1:100 dilution in buffer of 2.4G2 antibody, 0.5 mg/ml, #553142 BD Bioscience) was added to each well and plates were incubated for 15 minutes at room temperature. Then specific antibodies against human targets hCD45 (Life Technologies) and hCD8 (BD Bioscience) were added (0.5-1 µg/sample) and plates were incubated at 4° C. for 30 minutes protected from light. Following another washing step (centrifugation of the plates at 400×g for 3 minutes at 4° C.), cells were resuspended in 200 µl FC Buffer for analysis with an Attune Focusing Cytometer (blue (488 nm)/violet (405 nm) laser configuration). Flow cytometry data were analyzed with the FlowJo Data Analysis Software.

FIG. 24 shows the CD45 and CD8 phenotype of PMBCs from the treatment and control groups of Example 20 after study end. FIG. 24A shows the percentage of total PMBCs expressing CD45 while FIG. 24B shows the fraction of $CD45^+CD8^+$ T effector cells in the CD45-positive cell population. Clearly, the results demonstrate that the anti-CD137 antibody SEQ ID NOs: 32 and 33 treatment leads to stronger expansion of human lymphocytes in the mouse peripheral blood compared to the control group or all doses of SEQ ID NOs: 9 and 10, and that this expansion correlates with a stronger increase in the $CD8^+$ human effector T cells. Combined with the mortality data shown in FIG. 20, the results indicate that the accelerated xGvHD induced by anti-CD137 mAb treatment is caused by an increased expansion of $CD8^+$ human effector T cells in the anti-CD137 group compared to the control or SEQ ID NOs: 9 and 10 groups.

Combining the evidence of Examples 18, 19 and 20, the following conclusions can be drawn:

(i) SEQ ID NOs: 9 and 10 has a dual functionality: It leads to direct tumor regression due to an anti-HER2 effect, and a tumor-localized increase in the density of human lymphocytes by HER2-tumor-target localized CD137 targeting.

(ii) Suprisingly, the direct anti-HER2 effect is not dependent on any Fc-gamma receptor mediated effector functionality, as both the CD137/HER2 bispecific SEQ ID NOs: 9 and 10 and the HER2 monospecific antibody SEQ ID NOs: 51 and 52 should not elicit any effector functions: Both possess an IgG4 antibody backbone with additional mutations that essentially eliminates Fc-gamma receptor interactions.

(iii) The benefit of bispecific, tumor-localized CD137 targeting regarding both efficacy and safety becomes evident by comparison with the monospecifically CD137-targeting benchmark antibody: While the CD137/HER2 bispecific leads to a strong increase of human lymphocytes in the tumor compared to controls, the monospecific CD137-targeting antibody even leads to a decrease compared to controls. On the other hand, the monospecific CD137-targeting antibody leads to an expansion of human CD8-positive T cells in the peripheral blood of the mice in the study, an effect which is not apparent for SEQ ID NOs: 9 and 10. The peripheral expansion of $CD8^+$ effector cells correlates with an accelerated mortality of mice via xGvHD. Such toxicity brought about by systemic activation of CD137 may also be relevant for the clinical application of anti-CD137 antibodies such as SEQ ID NOs: 32 and 33. These observations strongly vouch for both an improved efficacy and safety of SEQ ID NOs: 9 and 10 compared to monospecific anti-CD137 benchmarks such as SEQ ID NOs: 32 and 33.

It is obvious to those skilled in the art that variants of the in vivo model described in this application can be applied to show various aspects of the in vivo efficacy of SEQ ID NOs: 9 and 10. Generally, such models will be based on an engraftment with tumor cells that are positive for the human HER2 receptor or variants thereof, which is enabled by tumor cells that are either naturally HER2-receptor positive or made HER2-receptor positive by methods such as transfection or viral transduction with HER2. Such cells can be either derived from immortal cancer cell lines or patient tumors. In addition, the models may rely on alloreactive or HLA-matched and tumor-reactive T cells of human or murine origin, for example:

(I) Humanized models based on HER2-positive tumors and alloreactive PBMC. Typically, mice employed in such models will be immunocompromised to a lesser or larger degree. Examples of a model based on an immortal cell line are provided in this application, and for example in Sanmamed et al., Cancer Res. 2015 Sep. 1; 75(17):3466-78. The latter publication also provides an example for a typical model based on a patient-derived tumor cell xenograft.

(II) Humanized models based on HER2-positive tumors and monoclonal or polyclonal T cells that recognize one or more antigens on the tumor cell line. Typically, mice employed in such models will be immunocompromised to a lesser or larger degree. Various combinations of tumor cell specific T cells and tumor cells are possible. Tumor cell specific T cells may be obtained by generating partly or fully HLA-matched monoclonal or polyclonal tumor-reactive T cells via different protocols, for example as described in Erskine et al., J Vis Exp. 2012 Aug. 8; (66):e3683, or by transducing T cells with a natural T cell receptor, for example as described in Wang et al., Cancer Immunol Res. 2016 March; 4(3):204-14, or Hirschhorn-Cymerman et al., J Exp Med. 2012 Oct. 22; 209(11):2113-26. An artificial chimeric antigen receptor may also be employed to replace the natural TCR.

(III) Patient-derived tumor cells and autologous patient-derived PBMC or (expanded) TIL. Typically, mice employed in such models will be immunocompromised to a lesser or larger degree.

(IV) A transgenic mouse model, where the CD137 receptor is partially or fully humanized, and thus made capable of binding to SEQ ID NOs: 9 and 10. Transgenic mice will be engrafted with mouse tumors that were made to express human HER2 by cell biological methods. To increase the physiological relevance of the model, the mouse can be additionally made transgenic for the CD137 ligand and/or human HER2.

The models described in the above or variants thereof are expected to be capable of showing one or more of the following pharmacodynamics effects: an increase in TIL frequency via direct or indirect enhancement of local proliferation, an increase in TIL frequency via direct or indirect suppression of lymphocyte cell death, an increase in TIL activity different from proliferation or persistence such as the production of proinflammatory cytokines including but not limited to IL-2, IFN-γ or TNF-α or an improved capacity to kill tumor cells as evidenced by a strong impact on tumor growth that is not due to the anti-HER2 activity of SEQ ID NOs: 9 and 10 alone. Lymphocytes affected include, but are not limited to CD4- and CD8-positive T cells, NK cells or NKT cells. Other cell types may show specific pharmacodynamics effects, including but not limited to endothelial cells, for example endothelial cells of the tumor vessels. In the case of tumor endothelial cells, CD137 targeting by SEQ ID NOs: 9 and 10 may to an enhancement of trafficking into the tumor (cf. Palazon et al., Cancer Res. 2011 Feb. 1; 71(3):801-11) via expression of targeting receptors or soluble factors enhancing the targeting.

The models may be straightforwardly employed to study additional effects such as specific targeting of lymphocyte subsets, dose dependency of pharmacodynamic and toxic effects, or treatment schedules.

Embodiments illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present embodiments have been specifically disclosed by preferred embodiments and optional features, modification and variations thereof may be resorted to by those skilled in the art, and that such modifications and variations are considered to be within the scope of this invention. All patents, patent applications, textbooks and peer-reviewed publications described herein are hereby incorporated by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply. Each of the narrower species and sub-generic groupings falling within the generic disclosure also forms part of the invention. This includes the generic description of the invention with a proviso or negative limitation removing any subject matter from the genus, regardless of whether or not the excised material is specifically recited herein. In addition, where features are described in terms of Markush groups, those skilled in the art will recognize that the disclosure is also thereby described in terms of any individual member or subgroup of members of the Markush group. Further embodiments will become apparent from the following claims.

EQUIVALENTS

Those skilled in the art will recognize, or be able to ascertain using no more than routine experimentation, many equivalents to the specific embodiments of the invention described herein. Such equivalents are intended to be encompassed by the following claims. All publications, patents and patent applications mentioned in this specification are herein incorporated by reference into the specification to the same extent as if each individual publication, patent or patent application was specifically and individually indicated to be incorporated herein by reference.

The invention claimed is:

1. A fusion polypeptide that is capable of simultaneously binding both CD137 and HER2/neu, wherein the fusion polypeptide comprises at least two subunits, wherein the first subunit comprises an immunoglobulin, which first binding domain has binding specificity for HER2/neu, and wherein the second subunit comprises a lipocalin mutein having binding specificity for CD137, wherein the fusion polypeptide comprises the amino acid sequences shown in SEQ ID NOs: 9 and 10.

2. The fusion polypeptide of claim 1, wherein the fusion polypeptide is capable of binding CD137 with an $EC_{50}$ value comparable to or lower than the $EC_{50}$ value of the lipocalin mutein specific for CD137 included in the fusion polypeptide.

3. The fusion polypeptide of claim 1, wherein the fusion polypeptide is capable of binding CD137 with an $EC_{50}$ value of about 1 nM or lower.

4. The fusion polypeptide of claim 1, wherein the fusion polypeptide is capable of binding HER2/neu with an $EC_{50}$ value comparable to or lower than the $EC_{50}$ value of the immunoglobulin specific for HER2/neu included in such fusion polypeptide.

5. The fusion polypeptide of claim 1, wherein the fusion polypeptide is capable of binding HER2/neu with an $EC_{50}$ value of about 1 nM.

6. The fusion polypeptide of claim 1, wherein the fusion polypeptide is capable of simultaneously binding CD137 and HER2/neu with $EC_{50}$ values of about 4 nM or lower.

7. The fusion polypeptide of claim 1, wherein the fusion polypeptide is capable of co-stimulating T-cell responses.

8. The fusion polypeptide of claim 1, wherein the fusion polypeptide is capable of inducing IL-2 secretion and T cell proliferation.

* * * * *

UNITED STATES PATENT AND TRADEMARK OFFICE
CERTIFICATE OF CORRECTION

| | |
|---|---|
| PATENT NO. | : 10,865,250 B2 |
| APPLICATION NO. | : 15/571561 |
| DATED | : December 15, 2020 |
| INVENTOR(S) | : Hinner et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 229 days.

Signed and Sealed this
Tenth Day of January, 2023

Katherine Kelly Vidal
*Director of the United States Patent and Trademark Office*